(12) United States Patent
Russell et al.

(10) Patent No.: US 12,053,529 B2
(45) Date of Patent: Aug. 6, 2024

(54) AMINO-REACTIVE POSITIVELY CHARGED ATRP INITIATORS THAT MAINTAIN THEIR POSITIVE CHARGE DURING SYNTHESIS OF BIOMACRO-INITIATORS

(71) Applicant: Carnegie Mellon University, Pittsburgh, PA (US)

(72) Inventors: Alan J. Russell, Gibsonia, PA (US); Hironobu Murata, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 517 days.

(21) Appl. No.: 17/264,455

(22) PCT Filed: Aug. 1, 2019

(86) PCT No.: PCT/US2019/044743
§ 371 (c)(1),
(2) Date: Jan. 29, 2021

(87) PCT Pub. No.: WO2020/028715
PCT Pub. Date: Feb. 6, 2020

(65) Prior Publication Data
US 2021/0316001 A1 Oct. 14, 2021

Related U.S. Application Data

(60) Provisional application No. 62/764,395, filed on Aug. 1, 2018.

(51) Int. Cl.
*A61K 47/58* (2017.01)
*A61K 38/17* (2006.01)
(Continued)

(52) U.S. Cl.
CPC .......... *A61K 47/58* (2017.08); *A61K 38/1703* (2013.01); *A61K 38/47* (2013.01);
(Continued)

(58) Field of Classification Search
CPC ..................................................... A61K 47/58
See application file for complete search history.

(56) References Cited

U.S. PATENT DOCUMENTS

| 3,424,839 A | 1/1969 | Montandraud et al. |
| 4,350,801 A | 9/1982 | Grasshoff |
| 5,639,633 A | 6/1997 | Callstrom et al. |
| 5,763,546 A | 6/1998 | Jung et al. |

(Continued)

FOREIGN PATENT DOCUMENTS

| CN | 103451174 | 12/2013 |
| EP | 0136728 | 4/1985 |

(Continued)

OTHER PUBLICATIONS

Ridgewell et al. "Stereochemical aspects of the glutathione S-transferase-catalyzed conjugations of alkyl halides." Drug metabolism and disposition 15.1 (1987): 82-90. (Year: 1987).*

Averick et al., "Solid-Phase Incorporation of an ATRP Initiator for Polymer-DNA Biohybrids," Angewandte Chemie Int. Ed., 2014, 53: 2739-2744.

(Continued)

*Primary Examiner* — Benjamin J Packard
(74) *Attorney, Agent, or Firm* — Fish & Richardson P.C.

(57) ABSTRACT

Provided herein are materials and methods that include utilizing atom transfer radical polymerization (ATRP) initiator molecules that maintain a positive charge during biomacro-initiator synthesis.

23 Claims, 23 Drawing Sheets
Specification includes a Sequence Listing.

(51) Int. Cl.
*A61K 38/47* (2006.01)
*A61K 38/48* (2006.01)
*A61K 47/54* (2017.01)

(52) U.S. Cl.
CPC .......... *A61K 38/4826* (2013.01); *A61K 47/54* (2017.08); *C12Y 302/01017* (2013.01); *C12Y 304/21001* (2013.01)

(56) References Cited

U.S. PATENT DOCUMENTS

| | | | |
|---|---|---|---|
| 5,789,487 | A | 8/1998 | Matyjaszewski et al. |
| 5,807,937 | A | 9/1998 | Matyjaszewski et al. |
| 5,998,588 | A | 2/1999 | Hoffman et al. |
| 5,945,491 | A | 8/1999 | Matyjaszewski et al. |
| 6,111,022 | A | 8/2000 | Matyjaszewski et al. |
| 6,121,371 | A | 9/2000 | Matyjaszewski et al. |
| 6,124,411 | A | 9/2000 | Matyjaszewski et al. |
| 6,162,882 | A | 12/2000 | Matyjaszewski et al. |
| 6,291,200 | B1 | 9/2001 | LeJeune et al. |
| 6,407,187 | B1 | 6/2002 | Matyjaszewski et al. |
| 6,512,060 | B1 | 1/2003 | Matyjaszewski et al. |
| 6,538,091 | B1 | 3/2003 | Matyjaszewski et al. |
| 6,541,580 | B1 | 4/2003 | Matyjaszewski et al. |
| 6,624,262 | B2 | 9/2003 | Matyjaszewski et al. |
| 6,624,263 | B2 | 9/2003 | Matyjaszewski et al. |
| 6,627,314 | B2 | 9/2003 | Matyjaszewski et al. |
| 6,642,037 | B2 | 11/2003 | Gordon et al. |
| 6,759,220 | B1 | 7/2004 | LeJeune et al. |
| 6,759,491 | B2 | 7/2004 | Matyjaszewski et al. |
| 6,790,919 | B2 | 9/2004 | Matyjaszewski et al. |
| 6,887,962 | B2 | 5/2005 | Matyjaszewski et al. |
| 6,969,749 | B2 | 11/2005 | Lewandowski et al. |
| 7,019,082 | B2 | 3/2006 | Matyjaszewski et al. |
| 7,049,373 | B2 | 5/2006 | Matyjaszewski et al. |
| 7,064,166 | B2 | 6/2006 | Matyjaszewski et al. |
| 7,125,938 | B2 | 10/2006 | Matyjaszewski et al. |
| 7,157,530 | B2 | 1/2007 | Matyjaszewski et al. |
| 7,332,550 | B2 | 2/2008 | Matyjaszewski et al. |
| 7,407,995 | B2 | 8/2008 | Ok et al. |
| 7,572,764 | B2 | 8/2009 | Cohen et al. |
| 7,572,874 | B2 | 8/2009 | Matyjaszewski et al. |
| 7,678,869 | B2 | 3/2010 | Matyjaszewski et al. |
| 7,722,838 | B2 | 5/2010 | Hyacinthe |
| 7,795,355 | B2 | 9/2010 | Matyjaszewski et al. |
| 7,825,199 | B1 | 11/2010 | Matyjaszewski et al. |
| 7,893,173 | B2 | 2/2011 | Matyjaszewski et al. |
| 7,893,174 | B2 | 2/2011 | Matyjaszewski et al. |
| 8,252,880 | B2 | 8/2012 | Matyjaszewski et al. |
| 8,273,823 | B2 | 9/2012 | Matyjaszewski et al. |
| 8,349,410 | B2 | 1/2013 | Huang et al. |
| 8,367,051 | B2 | 2/2013 | Matyjaszewski et al. |
| 8,404,788 | B2 | 3/2013 | Matyjaszewski et al. |
| 8,445,610 | B2 | 5/2013 | Matyjaszewski et al. |
| 8,816,001 | B2 | 8/2014 | Mehl et al. |
| 8,865,795 | B1 | 10/2014 | Xin et al. |
| 8,865,797 | B2 | 10/2014 | Matyjaszewski et al. |
| 8,871,831 | B2 | 10/2014 | Huang et al. |
| 8,962,764 | B2 | 5/2015 | Matyjaszewski et al. |
| 9,243,274 | B2 | 1/2016 | Mehl et al. |
| 9,410,020 | B2 | 8/2016 | Matyjaszewski et al. |
| 9,447,042 | B2 | 9/2016 | Kita et al. |
| 9,533,297 | B2 | 1/2017 | Matyjaszewski et al. |
| 9,539,338 | B2 | 1/2017 | Russell et al. |
| 9,644,042 | B2 | 5/2017 | Matyjaszewski et al. |
| 10,400,232 | B2 | 9/2019 | Russell et al. |
| 11,472,894 | B2 | 10/2022 | Matyjaszewski et al. |
| 11,919,991 | B2 | 3/2024 | Matyjaszewski et al. |
| 2004/0152880 | A1 | 8/2004 | Minden |
| 2005/0065300 | A1 | 3/2005 | Lewandowski et al. |
| 2005/0107277 | A1 | 5/2005 | Lin et al. |
| 2007/0123646 | A1 | 5/2007 | Lele et al. |
| 2007/0219330 | A1 | 9/2007 | Haddleton et al. |
| 2007/0276088 | A1 | 11/2007 | Maynard et al. |
| 2007/0287828 | A1 | 12/2007 | Minden |
| 2008/0206182 | A1 | 8/2008 | Sommermeyer et al. |
| 2009/0095668 | A1 | 4/2009 | Busson |
| 2009/0171024 | A1 | 7/2009 | Jakubowski et al. |
| 2010/0130721 | A1 | 5/2010 | Iwakura et al. |
| 2011/0091957 | A1 | 4/2011 | Lele et al. |
| 2012/0213986 | A1 | 8/2012 | Kowalewski |
| 2013/0058910 | A1 | 3/2013 | Koepsel et al. |
| 2013/0071394 | A1 | 3/2013 | Troyer et al. |
| 2013/0131278 | A1 | 5/2013 | Huang et al. |
| 2014/0183055 | A1 | 7/2014 | Matyjaszewski et al. |
| 2014/0275420 | A1 | 9/2014 | Matyjaszewski et al. |
| 2015/0087795 | A1 | 3/2015 | Matyjaszewski et al. |
| 2016/0101190 | A1 | 4/2016 | Russell et al. |
| 2016/0200840 | A1 | 7/2016 | Matyjaszewski et al. |
| 2016/0244741 | A1 | 8/2016 | Russell et al. |
| 2017/0113934 | A1 | 4/2017 | Kowalewski |
| 2018/0051271 | A1 | 2/2018 | Russell et al. |
| 2019/0358335 | A1 | 11/2019 | Russell et al. |
| 2020/0024372 | A1 | 1/2020 | Matyjaszewski et al. |
| 2020/0369716 | A1 | 11/2020 | Murata et al. |
| 2021/0290769 | A1 | 9/2021 | Russell et al. |
| 2021/0388337 | A1 | 12/2021 | Murata et al. |
| 2023/0079313 | A1 | 3/2023 | Matyjaszewski et al. |

FOREIGN PATENT DOCUMENTS

| | | |
|---|---|---|
| GB | 2215335 | 9/1989 |
| WO | WO 1998/015620 | 4/1998 |
| WO | WO 2002/083708 | 10/2002 |
| WO | WO 2013/028756 | 2/2013 |
| WO | WO 2014/176279 | 10/2014 |
| WO | WO 2015/051326 | 4/2015 |
| WO | WO 2016/130677 | 8/2015 |
| WO | WO 2019/028168 | 2/2019 |
| WO | WO 2020/123023 | 6/2020 |

OTHER PUBLICATIONS

Hucknall et al., "In Pursuit of Zero: Polymer Brushes that Resist the Adsorption of Proteins," Advanced Materials, 2009, 21(23):2441-2446.

Zavada et al., "Radical-Mediated Enzymatic Polymerizations," International Journal of Molecular Sciences, 2016, 17(195): 1-27.

Enciso et al., "A Breathing Atom-Transfer Radical Polymerization: Fully Oxygen-Tolerant Polymerization Inspired by Aerobic Respiration of Cells," Angewandte Chemie, 2018, 57:933-936.

Fu et al., "Synthesis of Polymer Bioconjugates via Photoinduced Atom Transfer Radical Polymerization under Blue Light Irradiation," ACS Macro Letters, 2018, 7:1248-1253.

Ahmed et al., "Surface Plasmon Resonance (SPR) Spectrometry as a Tool to Analyze Nucleic Acid-Protein Interactions in Crude Cellular Extracts," Cancer Genomics & Proteomics, Nov. 2010, 7(6):303-309.

Bi et al., "Introducing Biobased Ionic Liquids as the Nonaqueous Media for Enzymatic Synthesis of Phosphatidylserine," Journal of Agricultural and Food Chemistry, Jan. 2015, 63(5):1558-1561.

Burczak et al., "Protein permeation through poly(vinyl alcohol) hydrogel membranes," Biomaterials, Feb. 1994, 15(3):231-238.

Carmali et al., "Tailoring Site Specificity of Bioconjugation Using Step-Wise Atom-Transfer Radical Polymerization on Proteins," Biomacromolecules, Sep. 2018, 19(10):4044-4051.

Chen et al., "Surface hydration: Principles and applications toward low-fouling/nonfouling biomaterials," Polymer, Oct. 2010, 51(23):5283-5293.

Chien et al., "Surface conjugation of zwitterionic polymers to inhibit cell adhesion and protein adsorption," Colloids and Surfaces B: Biointerfaces, Jul. 2013, 107:152-159.

Ghisaidoobe et al., "Intrinsic Tryptophan Fluorescence in the Detection and Analysis of Proteins: A Focus on Förster Resonance Energy Transfer Techniques," International Journal of Molecular Sciences, Dec. 2014, 15:22518-22538.

Green et al., "Surface plasmon resonance for real time in situ analysis of protein adsorption to polymer surfaces," Biomaterials, Mar. 1997, 18(5):405-413.

(56) References Cited

OTHER PUBLICATIONS

Green et al., "Surface plasmon resonance analysis of dynamic biological interactions with biomaterials," Biomaterials, Sep. 2000, 21(18):1823-1835.
Grewer et al., "Mechanism of the Triplet-State Quenching by Molecular Oxygen in Solution," Journal of Physical Chemistry, Apr. 1994, 98(16):4230-4235.
Grover et al., "Protein-polymer conjugates: synthetic approaches by controlled radical polymerizations and interesting applications," Current Opinion in Chemical Biology, Dec. 2010, 14(6): 818-827.
Hook et al., "Variations in Coupled Water, Viscoelastic Properties, and Film Thickness of a Mefp-1 Protein Film during Adsorption and Cross-Linking: A Quartz Crystal Microbalance with Dissipation Monitoring, Ellipsometry, and Surface Plasmon Resonance Study," Analytical Chemistry, Nov. 2001, 73(24):5796-5804.
Hucknall et al., "In Pursuit of Zero: Polymer Brushes that Resist the Adsorption of Proteins," Advanced Materials, 21(23):2441-2446.
Jeon et al., "Protein—surface interactions in the presence of polyethylene oxide: I. Simplified theory," Journal of Colloid and Interface Science, Mar. 1991, 142(1): 149-158.
Jevsevar et al., "PEGylation of therapeutic proteins," Biotechnology Journal, Jan. 2010, 5(1):113-128.
Kurzban et al., "Shielding of tryptophan residues of avidin by the binding of biotin," Biochemistry, Oct. 1989, 28(21):8537-8542.
Kurzban et al., "Biotin binding changes the conformation and decreases tryptophan accessibility of streptavidin," Journal of Protein Chemistry, Dec. 1990, 9:673-682.
Leigh et al., "Photopolymerizable Zwitterionic Polymer Patterns Control Cell Adhesion and Guide Neural Growth," Biomacromolecules, Jul. 2017, 18(8):2389-2401.
Lin et al., "Different in vitro and in vivo behaviors between Poly(carboxybetaine methacrylate) and poly(sulfobetaine methacrylate)," Colloids and Surfaces B: Biointerfaces, Oct. 2016, 146:888-894.
Liu et al., "Molecular Sieving on the Surface of a Protein Provides Protection Without Loss of Activity," Advanced Functional Materials, Nov. 2012, 23(16):2007-2015.
Luan et al., ""Hearing Loss" in QCM Measurement of Protein Adsorption to Protein Resistant Polymer Brush Layers," Analytical Chemistry, Mar. 2017, 89(7):4184-4191.
MacBeath et al., "Printing Small Molecules as Microarrays and Detecting Protein-Ligand Interactions en Masse," Journal of the American Chemical Society, Aug. 1999, 121(34):7967-7968.
Muegge et al., "A General and Fast Scoring Function for Protein-Ligand Interactions: A Simplified Potential Approach," Journal of Medicinal Chemistry, Feb. 1999, 42(5):791-804.
PCT International Preliminary Report on Patentability in International Application No. PCT/US2019/055977, dated Apr. 8, 2021, 5 pages.
PCT International Search Report and Written Opinion in International Application No. PCT/US2019/055977, dated Jun. 17, 2020, 10 pages.
Sarker et al., "Excited States of Bromine-Substituted Distyrylbenzenes: Models for Conjugated Polymer Emission," The Journal of Physical Chemistry A, Aug. 2003, 107(34):6533-6537.
Schlenoff, "Zwitteration: Coating Surfaces with Zwitterionic Functionality to Reduce Nonspecific Adsorption," Langmuir, Apr. 2014, 30(32):9625-9636.
Skelly et al., "Conformational effects of nucleotide exchange in ras p21 proteins as studied by fluorescence spectroscopy," FEBS Letters, Mar. 1990, 262(1): 127-130.
Sofia et al., "Poly(ethylene oxide) Grafted to Silicon Surfaces: Grafting Density and Protein Adsorption," Macromolecules, Jul. 1998, 31(15):5059-5070.
Szleifer, "Protein adsorption on surfaces with grafted polymers: a theoretical approach," Biophysical Journal, Feb. 1997, 72(2):595-612.
Treethammathurot et al., "Effect of PEG molecular weight and linking chemistry on the biological activity and thermal stability of PEGylated trypsin," International Journal of Pharmaceutics, Jun. 2008, 357(1-2):252-259.

Vivian et al., "Mechanisms of Tryptophan Fluorescence Shifts in Proteins," Biophysical Journal, May 2001, 80(5):2093-2109.
Wilchek et al., "Essentials of biorecognition: The (strept)avidin-biotin system as a model for protein-protein and protein-ligand interaction," Immunology Letters, Feb. 2006, 103(1):27-32.
Wu et al., "Protein-polymer therapeutics: a macromolecular perspective," Biomaterials Science, Oct. 2014, 3(2):214-230.
Yee et al., "NMR and X-ray Crystallography, Complementary Tools in Structural Proteomics of Small Proteins," Journal of the American Chemical Society, Nov. 2005, 127(47): 16512-16517.
Abian et al., "Stabilization of penicillin G acylase from *Escherichia coli*: site-directed mutagenesis of the protein surface to increase multipoint covalent attachment," J. M. Appl. Environ. Microbiol., 2004, 70(2):1249-51.
Abuchowski et al., "Alteration of Immunological Properties of Bovine Serum Albumin by Covalent Attachment of Polyethylene Glycol," J. Control. Rel., 1997, 252(11):3578-3581.
Abuchowski et al., "Effect of Covalent Attachment of Polyethylene Glycol on Immunogenicity and Circulating Life of Bovine," J Bio. Chem., 1976, 252(11):3582-3586.
Abzalimov et al., "Structural characterization of protein-polymer conjugates. I. Assessing heterogeneity of a small PEGylated protein and mapping conjugation sites using ion exchange chromatography and top-down tandem mass spectrometry," International Journal of Mass Spectrometry, 2012, 312: 135-143.
Advances in Polymer Science; Springer Berlin / Heidelberg: 2002, vol. 159 (Table of Contents).
Affleck et al., "Enzymatic catalysis and dynamics in low-water environments," Proceedings of the National Academy of Sciences of the United States of America, 1992, 89(3):1100-1104.
Al-Ajlan et al., "Purification and partial characterization of camel anionic chymotrypsin," Arch. Biochem. Biophys., 1997, 348(2):363-8.
Alconcel et al., "FDA-approved poly(ethylene glycol)-protein conjugate drugs," Polymer Chem., 2011, 2:1442-1448.
Amitai et al., "Decontamination of chemical and biological warfare agents with a single multi-functional material," Biomaterials, May 2010, 31(15):4417-4425.
Arotcarena et al., "Switching the Inside and the Outside of Aggregates of Water-Soluble Block Copolymers with Double Thermoresponsivity," J. Am. Chem. Soc., 2002, 124(14):3787-3793.
Asgeirsson et al., "Structural and kinetic properties of chymotrypsin from Atlantic cod (*Gadus morhua*). Comparison with bovine chymotrypsin," Comp. Biochem. Physiol B., 1991, 99(2):327-35.
Ashani et al., "Estimation of the Upper Limit of Human Butyrylcholinesterase Dose Required for Protection against Organophosphates Toxicity: a Mathematically Based Toxicokinetic Model," Toxicological Sciences, 2004, 77(2):358-367.
Asmus et al., "Low-temperature NMR characterization of reaction of sodium pyruvate with hydrogen peroxide," J. Phys. Chem. A., 2015, 119(6):966-977.
Averick et al., "ATRP under Biologically Relevant Conditions: Grafting from a Protein," ACS Macro Letters, 2012, 1(1):6-10.
Averick et al., "Preparation of Cationic Nanogels for Nucleic Acid Delivery," Biomacromolecules, 2012, 13(11):3445-3449.
Averick et al., "Well-defined biohybrids using reversible-deactivation radical polymerization procedures," J. Control. Release, 2015, 205:45-57.
Axelsen et al., "Structure and dynamics of the active site gorge of acetylcholinesterase: Synergistic use of molecular dynamics simulation and X-ray crystallography," Protein Science, 1994, 3(2): 188-197.
Bahulekar et al., "Polyethyleneimine in Immobilization of Biocatalysts," Enzyme Microb. Technol., 1991, 13(11):858-868.
Baldassarre et al., "Detection of endoplasmic reticulum stress markers and production enhancement treatments in transgenic goats expressing recombinant human butyrylcholinesterase," Transgenic Res, Dec. 2011, 20(6):1265-1272.
Baldwin, "How Hofmeister Ion Interactions Affect Protein Stability," Biophys J., 1996, 71(4):2056-2063.

(56) References Cited

OTHER PUBLICATIONS

Barbosa et al., "Strategies for the One-Step Immobilization-Purification of Enzymes as Industrial Biocatalysts," Biotechnol. Adv., 2015, 33(5):435-456.
Bas et al., "Very Fast Prediction and Rationalization of pKa Values for Protein-ligand Complexes," Proteins: Struct., Funct., Bioinf., 2008, 73: 765-783.
Bennion et al., "Counteraction of urea-induced protein denaturation by trimethylamine N-oxide: a chemical chaperone at atomic resolution," Natl. Acad. Sci. U.S.A., 2004, 101(17):6433-8.
Benns et al., "pH-Sensitive Cationic Polymer Gene Delivery Vehicle: N-Ac-poly(L-histidine)-graft-poly(L-lysine) Comb Shaped Polymer," Bioconjugate Chem, 2000, 11(5):637-645.
Benschop et al., "Nerve agent stereoisomers: analysis, isolation and toxicology," Acc. Chem. Res., 1988, 21(10):368-374.
Berberich et al., "Use of Salt Hydrate Pairs to Control Water Activity for Enzyme Catalysis in Ionic Liquids," Biotechnology Progress, 2003, 19(3):1029-1032.
Bhattacharjee et al., "Site-Specific Zwitterionic Polymer Conjugates of a Protein Have Long Plasma Circulation," ChemBioChem, 2015, 16(17):2451-2455.
Bigley et al., "Enzymatic Neutralization of the Chemical Warfare Agent VX: Evolution of Phosphotriesterase for Phosphorothiolate Hydrolysis," J. Am. Chem. Soc., 2013, 135(28):10426-10432.
Blencowe et al., "Core cross-linked star polymers via controlled radical polymerisation," Polymer, 2009, 50(1):5-32.
Blow "The study of alpha-chymotrypsin by x-ray diffraction. The Third CIBA Medal Lecture," Biochem. J., 1969, 112(3):261-268.
Boal et al., "Structural biology of copper trafficking," Chemical Reviews, 2009, 109(10):4760-4779.
Bonet et al., "Glucose oxidase effect on dough rheology and bread quality: A study from macroscopic to molecular level," Food Chemistry, 2006, 99(2):408-415.
Bordusa, "Proteases in Organic Synthesis," Chemical Reviews, 2002, 102(12):4817-4868.
Borowitz et al., "Study of a novel pancreatic enzyme replacement therapy in pancreatic insufficient subjects with cystic fibrosis," J. Pediatr., 2006, 149(5):658-662.
Bovara et al., "Activity, stability and conformation of methoxypoly(ethylene glycol)-subtilisin at different concentrations of water in dioxane," Biotechnol Bioeng, 1997, 54(1):50-57.
Bowers et al., "Scalable Algorithms for Molecular Dynamics Simulations on Commodity Clusters," F. D. In SC 2006 Conference, Proceedings of the ACM/IEEE;IEEE: 2006, 43.
Boyer et al., "Well-Defined Protein-Polymer Conjugates via in Situ RAFT Polymerization," J. Am. Chem. Soc., 2007, 129(22):7145-7154.
Braunecker, "Controlled/living radical polymerization: Features, developments, and perspectives," Prog. Polym. Sci., 2007, 32(1):93-146.
Brittain et al., "A Structural Definition of Polymer Brushes," Polym. Sci., Part A, Polym. Chem. 2007, 45(16):3505-3512.
Browne et al., "A possible three-dimensional structure of bovine α-lactalbumin based on that of hen's egg-white lysozyme," Journal of Molecular Biology, May 1969, 42(1):65-86.
Broyer et al., "Emerging synthetic approaches for protein-polymer conjugations," Chem. Commun., 2011, 47(8):2212-2226.
Bultz et al., "Ferrocene cocatalysis for ruthenium-catalyzed radical miniemulsion polymerization," Polymer, 2016, 106:313-319.
Caldwell et al., "Immobilization of Enzymes Based on Hydrophobic Interaction. I. Preparation and Properties of a Beta-Amylase Adsorbate," Biotechnol. Bioeng., 1976, 18(11):1573-1 588.
Callahan et al., "Triple Stimulus-Responsive Polypeptide Nanoparticles That Enhance Intratumoral Spatial Distribution," Nano Lett., 2012, 12(4):2165-2170.
Calligari et al., "Adaptation of Extremophilic Proteins with Temperature and Pressure: Evidence from Initiation Factor 6," The Journal of Physical Chemistry B, May 2015, 119(25):7860-7873.

Campbell et al., "Intramolecular Electron Transfer through Poly-Ferrocenyl Glucose Oxidase Conjugates to Carbon Electrodes: 1. Sensor Sensitivity, Selectivity and Longevity," Electrochimica Acta, Sep. 2017, 248:578-584.
Campbell et al., "Polymer-Based Protein Engineering Grown Ferrocene-Containing Redox Polymers Improve Current Generation in an Enzymatic Biofuel Cell," Biosensors and Bioelectronics, Jun. 2016, 86, 446-453.
Canfield, "The Amino Acid Sequence of Egg White Lysozyme," Journal of Biological Chemistry, Aug. 1963, 228(8):2698-2707.
Cao et al., "Super-hydrophilic zwitterionic poly(carboxybetaine) and amphiphilic non-ionic poly(ethylene glycol) for stealth nanoparticles," Nano Today, Oct. 2012, 7(5):404-413.
Carmali et al., "Polymer-Based Protein Engineering: Synthesis and Characterization of Armored, High Graft Density Polymer-Protein Conjugates.," Methods in Enzymology, 2017, 590: 347-380.
Carmali et al., "Tertiary Structure-Based Prediction of How ATRP Initiators React with Proteins," ACS Biomaterials Science & Engineering, Jul. 2017, 3(9):2086-2097.
Carrea et al., "Properties and Synthetic Applications of Enzymes in Organic Solvents," Angewandte Chemie International Edition, 2000, 39(13):2226-2254.
Castillo-Yanez et al., "Biochemical characterization of an isoform of chymotrypsin from the viscera of Monterey sardine (*Sardinops sagax caerulea*), and comparison with bovine chymotrypsin," Food Chem., 2009, 112(3):634-639.
Chan et al., "Chapter 2—Building on What Nature Gave US: Engineering Cell Glycosylation Pathways," Biotechnology Bioengineering, 2008, pp. 37-74.
Chao et al., "Two structural scenarios for protein stabilization by PEG," J. Phys. Chem. B, 2014, 118(28):8388-95.
Chapman et al., "Combinatorial Low-Volume Synthesis of Well-Defined Polymers by Enzyme Degassing," Angew. Chem. Int. Ed., 2016, 55(14):4500-4503.
Chapman et al., "Highly Controlled Open Vessel RAFT Polymerizations by Enzyme Degassing," Macromol., 2014, 47(24):8541-8547.
Charles, "Soluble-Insoluble Enzyme Catalysts," Biotechnol Bioeng., 1974, 16(11):1553-1556.
Chatterjee et al., "Signatures of Protein Thermal Denaturation and Local Hydrophobicity in Domain Specific Hydration Behavior: A Comparative Molecular Dynamics Study," Mol. Biosyst., 2016, 12(4):1139-1150.
Chen et al., "Quaternary Ammonium Functionalized Poly(propylene imine) Dendrimers as Effective Antimicrobials: Structure-Activity Studies," Biomacromolecules, 2000, 1(3):473-480.
Chen et al., "Site-Selective Lysine Modification of Native Proteins and Peptides via Kinetically Controlled Labeling," Bioconjugate Chemistry, Feb. 2012, 23(3):500-508.
Chen et al., "Effects of polyelectrolyte complexation on the UCST of zwitterionic polymer," Polymer, 2000, 41:141-147.
Chen et al., "Polymer-protein conjugates: II. Affinity precipitation separation of human immunogammaglobulbin by a poly(isopropylacrylamide—) protein A conjugate," Biomaterials, 1990, 11(9):631-634.
Chilkoti et al., "Targeted drug delivery by thermally responsive polymers," Adv Drug Deliver Rev, 2002, 54(5):613-630.
Ciampolini et al., "Five-Coordinated High-Spin Complexes of Bivalent Cobalt, Nickel, and Copper with Tris(2-dimethylaminoethyl)amine," Inorg. Chem., 1966, 5(1):41-44.
CN Office Action in Chinese Appln. No. 201680021192.1, dated May 6, 2020, 5 pages.
Cobo et al., "Smart Hybrid Materials by Conjugation of Responsive Polymers to Biomacromolecules," Nat. Mater., 2014, 14(2):143-159.
Coessens et al., "Functional polymers by atom transfer radical polymerization," Prog. Polym. Sci., 2001, 26(3):337-377.
Coker, "Extremophiles and biotechnology: current uses and prospects [version 1; peer review: 2 approved]," F1000Research, 2016, 5: 1-7.
Colloc'h et al., "Functional relevance of the internal hydrophobic cavity of urate oxidase," FEBS Letters, May 2014, 588(9): 1715-1719.

(56) References Cited

OTHER PUBLICATIONS

Cummings et al., "Design of Stomach Acid-Stable and Mucin-Binding Enzyme Polymer Conjugates," Biomacromolecules, 2017, 18(2):576-586.
Cummings et al., "Dramatically Increased pH and Temperature Stability of Chymotrypsin Using Dual Block Polymer-Based Protein Engineering," Biomacromolecules, 2014, 15(3):763-771.
Cummings et al., "Polymer-Based Protein Engineering Enables Molecular Dissolution of Chymotrypsin in Acetonitrile," ACS Macro Letters, 2016, 5(4):493-497.
Cummings et al., "Tailoring enzyme activity and stability using polymer-based protein Engineering," Biomaterials, 2013, 34(30):7437-7443.
Da Silva Freitas et al., "Biochemical and biophysical characterization of lysozyme modified by PEGylation," International Journal of Pharmaceutics, Jun. 2010, 392(1-2): 111-117.
Davidovich-Pinhas et al., "Mucoadhesion: a review of characterization techniques," Expert Opin. Drug Delivery, 2010, 7(2):259-71.
Davis et al., "A place for thioether chemistry in cellular copper ion recognition and trafficking," Nature Chem. Bio., 2008, 4(3):148-151.
Davis et al., "Statistical, Gradient, Block and Graft Copolymers by Controlled/Living Radical Polymerizations," Advances in Polymer Science, Oct. 2002, 159(1):1-13.
De Champdore et al., "Proteins from extremophiles as stable tools for advanced biotechnological applications of high social interest," Journal of The Royal Society Interface, 2007, 4(13):183-191.
De et al., "Temperature-Regulated Activity of Responsive Polymer-Protein Conjugates Prepared by Grafting-from via RAFT Polymerization," J. Am. Chem. Soc., 2008, 130(34):11288-11289.
Debuigne et al., "Synthesis of Poly(vinyl acetate) and Poly(vinyl alcohol) Containing Block Copolymers by Combination of Cobalt-Mediated Radical Polymerization and ATRP," Macromol., 2005, 38(23):9488-9496.
Depp et al., "Enzyme Sheathing Enables Nanoscale Solubilization of Biocatalyst and Dramatically Increases Activity in Organic Solvent," Biomacromolecules, 2008, 9(4):1348-1351.
Desie et al., "Study of the time-resolved tryptophan fluorescence of crystalline alpha-chymotrypsin," Biochemistry, 1986, 25(25):8301-8.
Dill, "Dominant forces in protein folding," Biochemistry, Aug. 1990, 29(31):7133-7155.
Dimitrov, "Therapeutic Proteins," Methods Mal. Biol., 2012, 899:1-26.
Dinndorf, P., et al., "FDA Drug Approval Summary: Pegaspargase (Oncaspar®) for the First-Line Treatment of Children with Acute Lymphoblastic Leukemia (ALL)," Oncologist, 2007, 12(8):991-998.
DiPalma et al., "Enzyme replacement for lactose malabsorption using a beta-D-galactosidase," J. Clin. Gastroenterol., 1989, 11(3):290-3.
Dong et al., "Synthesis and responsive behavior of poly(N,N-dimethylaminoethyl methacrylate) brushes grafted on silica nanoparticles and their quaternized derivatives," Polymer, 2012, 53(10):2074-2084.
Dorovska-Taran et al., "Comparison of the dynamic structure of α-chymotrypsin in aqueous solution and in reversed micelles by fluorescent active-site probing," European Journal of Biochemistry, Jan. 1993, 211(1-2):47-55.
Drevon et al., "Enzyme-Containing Michael-Adduct-Based Coatings," Biomacromolecules, 2003, 4(3):675-682.
Dvir et al., "Acetylcholinesterase: From 3D structure to function," Chemico-Biological Interactions, Sep. 2010, 187(1-3):10-22.
Dwyer et al., "Computational Design of a Biologically Active Enzyme," Science, Jun. 2004, 304(5679): 1967-1971.
Eckstein et al., "At low water activity a-chymotrypsin is more active in an ionic liquid than in non-ionic organic solvents," Biotechnology Letters, 2002, 24(11):867-872.

Eddleston et al., "Management of acute organophosphorus pesticide poisoning," Lancet, Feb. 2008, 371(9612):597-607.
EP Office Action in European Appln. No. 16749801.3, dated Oct. 2, 2018, 3 pages.
Estevez et al. "Model equations for the kinetics of covalent irreversible enzyme inhibition and spontaneous reactivation: Esterases and organophosphorus compounds," Critical Reviews in Toxicology, 2009, 39(5):427-448.
Eyer, "The Role of Oximes in the Management of Organophosphorus Pesticide Poisoning," Toxicological Reviews, 2003, 22(3):165-190.
Falatach et al., "Why synthesize protein-polymer conjugates? The stability and activity of chymotrypsin-polymer bioconjugates synthesized by RAFT," Polymer, 2015, 72(18):382-386.
Fantin et al., "Atom Transfer Radical Polymerization of Methacrylic Acid: A Won Challenge," J. Am. Chem. Soc., 2016, 138(23):7216-7219.
Fantin et al., "ATRP in Water: Kinetic Analysis of Active and Super-Active Catalysts for Enhanced Polymerization Control," Macromol., 2017, 50(7):2696-2705.
Fersht, "Conformational equilibria in α and δ-chymotrypsin: The energetics and importance of the salt bridge," Journal of Molecular Biology, Mar. 1972, 64(2):497-509.
Fieker et al., "Enzyme replacement therapy for pancreatic insufficiency: present and future," M. Clin. Exp. Gastroenterol., 2011, 4:55-73.
Finn, "PEGylation of Human Growth Hormone: Strategies and Properties.," PEGylated Protein Drugs: Basic Science and Clinical Applications, 2009, pp. 187-203.
Fischer et al., "Inhibition of chymotrypsin through surface binding using nanoparticle-based receptors," P. Natl. Acad. Sci. U.S.A. 2002, 99(8)5018-23.
Foser et al., "Isolation, structural characterization, and antiviral activity of positional isomers of monopegylated interferon α-2a (PEGASYS)," Protein Expression and Purification, Jul. 2003, 30(1):78-87.
Fuhrmann et al., "Sustained gastrointestinal activity of dendronized polymer-enzyme conjugates," Nat. Chem. 2013, 5(7):582-589.
Gabison et al., "Structural analysis of urate oxidase in complex with its natural substrate inhibited by cyanide: Mechanistic implications," BMC Structural Biology, Jul. 2008, 8(1):32, 8 pages.
Gao et al., "In situ growth of a PEG-like polymer from the C terminus of an intein fusion protein improves pharmacokinetics and tumor accumulation," Proceedings of the National Academy of Sciences of the USA, 2009, 106(36): 15231-15236.
Gao et al., "Synthesis of functional polymers with controlled architecture by CRP of monomers in the presence of cross-linkers: From stars to gels," Prog. Polym. Sci., 2009, 34(4):317-350.
Gaudriault et al., "Selective Labeling of Alpha- Or Epsilon-Amino Groups in Peptides by the Bolton-Hunter Reagent," Peptides, 1992, 13(6):1187-1192.
Gauthier et al., "Polymer-protein conjugates: an enzymatic activity perspective," Poly. Chem., 2010, 1(9);1341-1520.
Geokas et al., "The aging gastrointestinal tract, liver, and pancreas," P. Clin. Geriatr. Med., 1985, 1(1):177-205.
Gerislioglu et al., "Characterization of singly and multiply PEGylated insulin isomers by reversed-phase ultra-performance liquid chromatography interfaced with ion mobility mass spectrometry," Analytica Chimica Acta, Dec. 2017, 1004:58-66.
Girard et al., "Structure-Function Perturbation and Dissociation of Tetrameric Urate Oxidase by High Hydrostatic Pressure," Biophysical Journal, May 2010, 98(10):2365-2373.
Goldsmith, "Enzyme Engineering by Targeted Libraries," Meth Enzymol, 2013, 523:257-283.
Gong et al., "Releasable Conjugation of Polymers to Proteins," Bioconjug. Chem., 2015, 26(7):1179-1181.
Gormley et al., "Polymerization amplified detection for nanoparticle-based biosensing," Nano Letters, 2014, 14(11):6368-6373.
Graham, "Enzyme replacement therapy of exocrine pancreatic insufficiency in man. Relations between in vitro enzyme activities and in vivo potency in commercial pancreatic extracts," N. Engl. J. Med., 1977, 296(23):1314-7.

(56) References Cited

OTHER PUBLICATIONS

Green, "A Spectrophotometric Assay for Avidin and Biotin Based on Binding of Dyes by Avidin," Biochem. J., 1965, 94:23-24.

Griengl et al., "The Synthesis of Chiral Cyanohydrins by Oxynitrilases," Trends Biotechnol., 2000, 18(6):252-256.

Gulla et al., "Reactivation of immobilized acetyl cholinesterase in an amperometric biosensor for organophosphorus pesticide," Biochim Biophys Acta, 2002, 1597(1):133-139.

Gunther et al., "Trypsin-specific acyl-4-guanidinophenyl Esters for Alpha-Chymotrypsin-Catalysed Reactions Computational Predictions, Hydrolyses, and Peptide Bond Formation," Eur. J Biochem. 2000, 267(12):3496-3501.

Gupta et al., "Directed evolution of hydrolases for prevention of G-type nerve agent intoxication," Nature Chemical Biology, 2011, 7(2):120-125.

Han et al., "Fluorometric Assay Protocol for Protease-Catalyzed Transesterification Reactions in Organic Solvents," The Journal of Organic Chemistry, 2004, 69(8):2853-2855.

Hanis et al., "Effect of Pegylation on Pharmaceuticals," Nat. Rev. Drug Discov., 2003, 2(3):214-221.

Hedstrom et al., "Serine Protease Mechanism and Specificity," Chem. Rev. 2002, 102(12):4501-4523.

Helsel et al., "Pharmacological activity of metal binding agents that alter copper bioavailability," Dalton Transactions, 2015, 44(19):8760-8770.

Heredia et al., "In Situ Preparation of Protein-"Smart" Polymer Conjugates With Retention of Bioactivity," J. Am. Chem. Soc., 2005, 127(48):16955-16960.

Heyman, "Lactose intolerance in infants, children, and adolescents," Pediatrics, 2006, 118(3)1279-86.

Hills, "Industrial use of lipases to produce fatty acid esters," Eur. J Lipid Sci. Technol., 2003, 105(10):601-607.

Hoffman et al., "Conjugates of Stimuli-responsive polymers and proteins," Prog. Polymer Sci., 2007, 32(8-9):922-932.

Hollecker et al., "Effect on protein stability of reversing the charge on amino groups," Biochimica et Biophysica Acta (BBA)—Protein Structure and Molecular Enzymology, Mar. 1982, 701(3):395-404.

Hong et al., "Conjugation of α-chymotrypsin on a polymeric hydrophilic nanolayer covering magnetic nanoparticles," J. Mol. Catal. B: Enzym., 2006, 42(3-4):99-105.

Huang et al., "Highly Active Biocatalytic Coatings from Protein-Polymer Diblock Copolymers," ACS Applied Materials & Interfaces, Jul. 2015, 7(27): 14660-14669.

Huang et al., "Nonleaching Antibacterial Glass Surfaces via "Grafting Onto": The Effect of the Number of Quaternary Ammonium Groups on Biocidal Activity," Langmuir, 2008, 24(13):6785-6795.

Isarov et al., ""Graft-to" Protein/Polymer Conjugates Using Polynorbornene Block Copolymers," Biomacromolecules, 2016, 17(2):641-648.

Isom et al., "Large shifts in pKa values of lysine residues buried inside a protein," Proc. Natl. Acad Sci. USA, 2011, 108(13):5260-5265.

Iwata et al., "Initiation of radical polymerization by glucose oxidase utilizing dissolved oxygen," J. Polym. Sci. Part A, Polym. Chem., 1991, 29(8):1217-1218.

Jansen et al., "Inhibition of the Proteinase and Esterase Activities of Trypsin and Chymotrypsin by Diisopropyl Fluorophosphate; Crystallization of Inhibited Chymotrypsin," J Biol Chem., 1949, 179(1):189-199.

Jesson et al., "H2O2 Enables Convenient Removal of RAFT End-Groups from Block Copolymer Nano-Objects Prepared via Polymerization-Induced Self-Assembly in Water," Macromolecules, 2017, 50(1):182-191.

Jiang et al., "Structural and Dynamic Evolution of the Amphipathic N-terminus Diversifies Enzyme Thermostability in the Glycoside Hydrolase Family 12," Phys. Chem. Chem. Phys., 2016, 18(31):21340-21350.

Jockusch et al., "The active role of excited states of phenothiazines in photoinduced metal free atom transfer radical polymerization: singlet or triplet excited states?" Polymer Chemistry, 2016, 7(39):6039-6043.

Johnson, "The Structure and Function of Lysozyme," Science Progress, Jul. 1966, 54(21):367-385.

Kaar et al., "Impact of Ionic Liquid Physical Properties on Lipase Activity and Stability," J Am Chem Soc, 2003, 125(14):4125-4131.

Kamigaito et al., "Metal-catalyzed living radical polymerization," Chem Rev, 2001, 101(12):3689-3746.

Keefe et al., "Poly(zwitterionic)protein conjugates offer increased stability without sacrificing binding affinity or bioactivity," Nat Chem, 2012, 4(1):59-63.

Kijima et al., "Study on tryptophan fluorescence and catalytic activity of α-chymotrypsin in aqueous-organic media," Enzyme Microb. Technol., 1996, 18(1):2-6.

Kim et al., "Activity-Based Assay of Matrix Metalloproteinase on Nonbiofouling Surfaces Using Time-of-Flight Secondary Ion Mass Spectrometry," Anal. Chem., 2008, 80(13):5094-5102.

Kitz et al., "Activity-structure relationships in the reactivation of diethylphosphoryl acetylcholinesterase by phenyl-l-methyl-pyridinium," Biochem Pharmacol, 1965, 14(10):1471-1477.

Klibanov, "Improving enzymes by using them in organic solvents," Nature, 2001, 409(6817):241-6.

Koide et al., "Stabilization of a Fibronectin Type III Domain by the Removal of Unfavorable Electrostatic Interactions on the Protein Surface," Biochemistry, Aug. 2001, 40(34):10326-10333.

Kolb et al., "Click Chemistry: Diverse Chemical Function from a Few Good Reactions," Agnew. Chem. Int. Ed., 2001, 40(11):2004-2021.

Konieczny et al., "Investigations on the activity of poly(2-oxazoline) enzyme conjugates dissolved in organic solvents," Journal of Biotechnology, 2014, 181(5):55-63.

Konkolewicz et al., "ICAR ATRP with ppm Cu Catalyst in Water," Macromol., 2012, 45(11):4461-4468.

Kostina et al., "Non-fouling hydrogels of 2-hydroxyethyl methacrylate and zwitterionic carboxybetaine (meth)acrylamides," Biomacromolecules, 2012, 13(12)4164-70.

Kovaliov et al., "Synthesis of lipase polymer hybrids with retained or enhanced activity using the grafting-from strategy," Polymer, Feb. 2018, 137:338-345.

Kovarik et al., "Mutation of acetylcholinesterase to enhance oxime-assisted catalytic turnover of methylphosphonates," Toxicology, 2007, 233(1-3):79-84.
Kovarik et al., "Oximes: Reactivators of phosphorylated-acetylcholinesterase and antidotes in therapy against tabun poisoning," Chemical-Biological Interactions, 2008, 175(1-3):173-179.
Kuca et al., "Synthesis of the three monopyridinium oximes and evaluation of their potency to reactivate acetylcholinesterase inhibited by nerve agents," J Appl Biomed, 2004, 2:51-56.
Kulkarni et al., "Controlling the Aggregation of Conjugates of Streptavidin with Smart Block Copolymers Prepared via the RAFT Copolymerization Technique," Biomacromolecules, 2006, 7(10):2736-2741.
Kulkarni et al., "Reversible Meso-Scale Smart Polymer-Protein Particles of Controlled Sizes," Bioconjugate Chem., 2004, 15(4):747-753.
Kumar et al., "Overview of the Stability of α-Chymotrypsin in Different Solvent Media," Chem. Rev., 2012, 112(7):4283-4307.
Kurinomaru et al., "Effects of multivalency and hydrophobicity of polyamines on enzyme hyperactivation of α-chymotrypsin," J. Mol. Catal. B: Enzym., 2015, 115:135-139.
Lackey et al., "Hemolytic Activity of pH-Responsive Polymer-Streptavidin Bioconjugates," Bioconjugate Chem., 1999, 10(3):401-405.
Larger et al., "Pancreatic exocrine function in patients with diabetes," Diabetic Medicine, 2012, 29(8):1047-1054.
Laszlo et al., "alpha-chymotrypsin catalysis in imidazolium-based ionic liquids," Biotechnol Bioeng, 2001, 75(2):181-186.
Laurell et al., "Thiol-disulfide Interchange Chromatography Using Sepharose-linked Thiol Compounds to Separate Plasma Proteins," Anal. Biochem., 1997, 81(2):336-345.

(56) References Cited

OTHER PUBLICATIONS

Laurents et al., "Charge-Charge Interactions are Key Determinants of the pK Values of Ionizable Groups in Ribonuclease Sa (pI=3.5) and a Basic Variant (pI=10.2)," Journal of Molecular Biology, Jan. 2003, 325(5): 1077-1092.
Lawrence et al., "Conjugation Strategy Strongly Impacts the Conformational Stability of a PEG-Protein Conjugate," ACS Chem. Biol., 2016, 11(7):1805-1809.
Lawrence et al., "Criteria for Selecting PEGylation Sites on Proteins for Higher Thermodynamic and Proteolytic Stability," J. Am. Chem. Soc., 2014, 136(50):17547-17560.
Lawrence et al., "How PEGylation influences protein conformational stability," Curr. Opin. Chem. Biol., 2016, 34:88-94.
Le Droumaguet et al., "Recent advances in the design of bioconjugates from controlled/living radical polymerization," Polymer Chemistry, Jul. 2010, 1(5):545-756.
Leach, "Release and breakdown of sialic acid from human salivary mucin and its role in the formation of dental plaque," Nature, 1963, 199:486-7.
Lee et al., "A Novel Method for Identifying PEGylation Sites of Protein Using Biotinylated PEG Derivatives," Journal of Pharmaceutical Sciences, Jan. 2003, 92(1):97-103.
Lee et al., "Activation of Oxygen and Hydrogen Peroxide by Copper(II) Coupled with Hydroxylamine for Oxidation of Organic Contaminants," Environ. Sci. Technol., 2016, 50(15):8231-8238.
Lee et al., "Effects of Charge-to-Alanine Substitutions on the Stability of Ribosomal Protein L30e from Thermococcus celer," Biochemistry, Dec. 2005, 44(51):16817-16825.
Lee et al., "Non-coding RNAs derived from an alternatively spliced REST transcript (REST-003) regulate breast cancer invasiveness," Scientific Reports, Jun. 2015, 5:892.
LeJeune et al., "Covalent linkage of mammalian cholinesterases within polyurethane foams," Med. Def. Biosc. Rev. Proc., 1996, 1:223-230.
Lele et al., "Enhancing Enzyme Stability Against TiO2-UV Induced Inactivation," Biomacromolecules, 2005, 6(1):475-482.
Lele et al., "Synthesis of Uniform Protein-Polymer Conjugates," Biomacromolecules, 2005, 6(6):3380-3387.
Lele, "Rational Protein Modification Leading to Resistance of Enzymes to TiO2-UV Irradiation-Induced Inactivation," Biomacromolecules, 2004, 5(5):1947-1955.
Levitsky et al., "Reversible conformational transition gives rise to 'zig-zag' temperature dependence of the rate constant of irreversible thermoinactivation of enzymes," European Journal of Biochem. 1994, 219(1-2):219-230.
Li et al., "Protein conjugation of thermoresponsive amine-reactive polymers prepared by RAFT," Polymer Chemistry, 2011, 2(2):323-327.
Li et al., "Block copolymer conjugates prepared by sequentially grafting from proteins via RAFT," Polym. Chem., 2011, 2:1531-1535.
Li et al., "Thermoresponsive Block Copolymer-Protein Conjugates Prepared by Grafting-from via RAFT Polymerization," Macromol. Rapid Commun., 2011, 32(4):354-359.
Li et.al., "Single-Ion Homopolymer Electrolytes with High Transference Number Prepared by Click Chemistry and Photoinduced Metal-Free Atom-Transfer Radical Polymerization," ACS Energy Letters, 2018, 3:20-27.
Limer et al., "Amide Functional Initiators for Transition-Metal-Mediated Living Radical Polymerization," Macromolecules, 2006, 39(4):1353-1358.
Lisowska et al., "Unresponsive or non-compliant steatorrhea in cystic fibrosis?," J. Cystic Fibrosis, 2006, 5(4):253-5.
Liu et al., "Semi-permeable coatings fabricated from comb-polymers efficiently protect proteins in vivo," Nature Communications, Nov. 2014, 5(5526): 1-8.
Liu et al., "In Situ Formation of Protein-Polymer Conjugates through Reversible Addition Fragmentation Chain Transfer Polymerization," Angew. Chem., Int. Ed. 2007, 46(17):3099-3103.

Lo Nostro et al., "Hofmeister Phenomena: An Update on Ion Specificity in Biology," Chem Rev 2012, 112(4):2286-2322.
Loke et al., "O-Substituted derivatives of pralidoxime: muscarinic properties and protection against soman effects in rats," European Journal of Pharmacology, 2002, 442(3):279-287.
Loladze et al., "Removal of surface charge-charge interactions from ubiquitin leaves the protein folded and very stable," Protein Science, Jan. 2002, 11(1): 174-177.
Lozano et al., "Dynamic Structure/Function Relationships in the α-Chymotrypsin Deactivation Process by Heat and pH," European Journal of Biochemistry, Aug. 1997, 248(1):80-85.
Lozano et al., "Effect of polyols on α-chymotrypsin thermostability: a mechanistic analysis of the enzyme stabilization," Journal of Biotechnology, Jun. 1994, 35(1):9-18.
Lozano et al., "Stabilization of a-chymotrypsin by ionic liquids in transesterification reactions," Biotechnology and Bioengineering, Dec. 2001, 75(5):563-569.
Lu et al., "Controllable synthesis of poly(N-vinylpyrrolidone) and its block copolymers by atom transfer radical polymerization," Polymer 2007, 48(10):2835-2842.
Lucius et al., "Investigating the Impact of Polymer Functional Groups on the Stability and Activity of Lysozyme-Polymer Conjugates," Biomacromolecules, 2016, 17(3):1123-1134.
Lundy et al., "Development of the Bisquaternary oxime HI-6 Toward Clinical Use in the Treatment of Organophosphate Nerve Agent Poisoning," Toxicological Reviews, 2006, 25(4):231-243.
Lv et al., "Glucose oxidase deoxygenation-redox initiation for RAFT polymerization in air," J. Polym. Sci. Part A, Polym. Chem., 2017, 55(1):164-174.
Magnusson et al., "In Situ Growth of Side-Chain PEG Polymers from Functionalized Human Growth Hormone—A New Technique for Preparation of Enhanced Protein-Polymer Conjugates," Bioconjugate Chem., 2010, 21(4):671-678.
Mahler et al., "Studies on Uricase. I. Preparation, Purification, and Properties of a Cuproprotein," J. Biol. Chem., 1955, 216(2):625-641.
Mancini et al., "Trehalose glycopolymers for stabilization of protein conjugates to environmental stressors," J. Am. Chem. Soc., 2012, 134(20):8474-9.
Masson, "Catalytic Bioscavengers Against Toxic Esters, an Alternative Approach for Prophylaxis and Treatments of Poisonings," Acta Naturae, 2009, No. 1(1):68-79.
Matyjaszewski et al., "Controlled/"Living" Radical Polymerization. Kinetics of the Homogeneous Atom Transfer Radical Polymerization of Styrene," J. Am. Chem. Soc., 1997, 119(4):674-680.
Matyjaszewski et al., "3.12—Copper-Mediated Atom Transfer Radical Polymerization," Polymer Science: A Comprehensive Reference, 2012; 3:377-428.
Matyjaszewski et al., "Atom Transfer Radical Polymerization," Chemical Reviews, 2001, 101 :2921-2990.
Matyjaszewski et al., "Controlled Radical Polymerization, Copyright, Advisory Board, Foreword," ACS Symp. Ser., 1998, 685:258-83.
Matyjaszewski et al., "Handbook of Radical Polymerization," John Wiley & Sons, Inc. pub., 2002, pp. 553-555, 567.
Matyjaszewski et al., "Macromolecular engineering by atom transfer radical polymerization," J. Am. Chem. Soc., 2014, 136(18):6513-6533.
Matyjaszewski, "Architecturally Complex Polymers with Controlled Heterogeneity," Science, Aug. 2011, 333(6046):1104-1105.
Matyjaszewski, "Atom Transfer Radical Polymerization (ATRP): Current Status and Future Perspectives," Macromol., 2012, 45(10):4015-4039.
Matyjaszewski, "Atom transfer radical polymerization," Chem. Rev., 2001, 101(9):2921-2990.
Matyjaszewski, "Atom Transfer Radical Polymerization: From Mechanisms to Applications," Isr . . . J. Chem., 2012, 52(3-4):206-220.
Matyjaszewski, "Bulk Atom Transfer Radical Polymerization," ACS Symp. Ser., 1998, 713:96-112.
Matyjaszewski, "Chemistry. Architecturally complex polymers with controlled heterogeneity," Science, 2011, 333(6046):1104-1105.
Matyjaszewski, "Comparison and Classification of Controlled/Living Radical Polymerizations," ACS Symp. Ser., 2000, 768:2-26.

(56) References Cited

OTHER PUBLICATIONS

Matyjaszewski, "Controlled Radical Polymerization: State of the Art in 2008," ACS Symp. Ser., 2009, 1023:3-13.
Matyjaszewski, "Controlled Radical Polymerization: State-of-the-Art in 2011," ACS Symp. Ser., 2012, 1100:1-13.
Matyjaszewski, "Controlled/Living Radical Polymerization: State of the Art in 2002," ACS Symp. Ser., 2003, 854:2-9.
Matyjaszewski, "Organic-Inorganic Hybrid Polymers from Atom Transfer Radical Polymerization and Poly(dimethylsiloxane)," ACS Symp. Ser., 2000, 729:270-283.
Matyjaszewski, "The Preparation of Well-Defined Water Soluble-Swellable (Co)Polymers by Atom Transfer Radical Polymerization," ACS Symp. Ser., 2000, 765:52-71.
Matyjaszewski, Abstracts of Papers, Mar. 2018 ACS Meeting, POLY-157.
Mazor et al., "Aging-Resistant Organophosphate Bioscavenger Based on Polyethylene Glycol-Conjugated F338A Human Acetylcholinesterase," Molecular Pharmacology, 2008, 74(3):755-763.
McDaniel et al., "Actively targeting solid tumours with thermoresponsive drug delivery systems that respond to mild hyperthermia," Int. J. Hyperthermia. 2013, 29:501-510.
Merrifield, "The role of the support in solid phase peptide synthesis," Br. Polym. J., 1984, 16:173-178.
Millard et al., "Controlled/Living Radical Polymerization: Progress in ATRP," American Chemical Society, 2009, 1023:127-136.
Millard et al., "Design and Expression of Organophosphorus Acid Anhydride Hydrolase Activity in Human Butyrylcholinesterase," Biochemistry, 1995, 34(49):15925-15933.
Millard et al., "Organosphosphorus Acid Anhydride Hydrolase Activity in Human Butyrylcholinesterase: Synergy Results in a Somanase," Biochemistry, 1998, 37(1):237-247.
Montalto et al., "Management and treatment of lactose malabsorption," World J. Gastroenterol., 2006, 12(2):187-91.
Moon et al., "Enzyme-catalyzed reactions in ionic liquids," Korean J. Chem. Eng., 2006, 23(2):247-263.
Mozhaev et al., "Multipoint attachment to a support protects enzyme from inactivation by organic solvents: α-Chymotrypsin in aqueous solutions of alcohols and diols," Biotechnology and Bioengineering, Mar. 1990, 35(7):653-659.
Murata et al. "Solid-Phase Synthesis of Protein-Polymers on Reversible Immobilization Supports," Nature Communications, Feb. 2018, 9(845):1-10.
Murata et al., "Rational tailoring of substrate and inhibitor affinity via ATRP polymer-based protein engineering," Biomacromolecules, 2014, 15(7):2817-2823.
Murata et al., "Polymer-Based Protein Engineering Can Rationally Tune Enzyme Activity, pH-Dependence, and Stability," Biomacromolecules, Jun. 2013, 14(6):1919-1926.
Naito, "Three-Dimensional Cardiac Tissue Engineering Using a Thermoresponsive Artificial Extracellular Matrix," ASAIO J. 2004, 50:344-348.
Nasongkla et al., "Multifunctional Polymeric Micelles as Cancer-Targeted, MRI—Ultrasensitive Drug Delivery Systems," Nano Lett, 2006, 6(11):2427-2430.
Nesbitt et al., "Mechanism of action of certolizumab pegol (CDP870): in vitro comparison with other anti-tumor necrosis factor alpha agents," Inflamm Bowel Dis, 2007, 13(11):1323-1332.
Nicolas et al., "Fluorescently tagged polymer bioconjugates from protein derived macroinitiators," Chem. Commun. 2006, 45:4697-4699.
Nieto et al., "Effects of Temperature and pH on the Regeneration of the Amino Groups of Ovalbumin After Modification With Citraconic and Dimethylmaleic Anhydrides," Biochim. Biophys. Acta., 1983, 749(2):204-210.
Nordwald et al., "Stabilization of Enzymes in Ionic Liquids Via Modification of Enzyme Charge," Biotechnology and Bioengineering, Apr. 2013, 110(9):2352-2360.
Nothling et al., "Self-deoxygenating glassware," Chem. Commun., 2019, 55(59):8544-8547.
Ordentlich et al., "The role of AChE active site gorge in determining stereoselectivity of charged and noncharged VX enantiomers," Chemico-Biological Interactions, 2005, 157-158:191-198.
O'Sullivan, "Use of Peginterferon Alfa-2B in Chronic Hepatitis C Patients Failing Prior Therapy: A Cost-Effectiveness Analysis," Value Health, 2008, 11(6):A437.
Oytun et al., "Sugar overcomes oxygen inhibition in photoinitiated free radical polymerization," J. Polym. Sci. Part A, Polym. Chem., 2013, 51(8):1685-1689.
Pace et al., "Forces contributing to the conformational stability of proteins," FASEB Journal, Jan. 1996, 10(1):75-83.
Pace et al., "Forces stabilizing proteins," FEES Letters, Jun. 2014, 588(14):2177-2184.
Paeth et al., "Chapter Nine—Approaches for Conjugating Tailor-Made Polymers to Proteins," Methods in Enzymology, 2017, 590:193-224.
Pan et al., "Automated Synthesis of Well-Defined Polymers and Biohybrids by Atom Transfer Radical Polymerization Using a DNA Synthesizer," Angew. Chem. Int. Ed., 2017, 56(10):2740-2743.
Pandey et al., "Impact of site-specific PEGylation on the conformational stability and folding rate of the Pin WW domain depends strongly on PEG oligomer length," Bioconjugate Chem., 2013, 24(5):796-802.
Panganiban et al., "Random heteropolymers preserve protein function in foreign environments," Science, Mar. 2018, 359(6381):1239-1243.
Park et al., "Advances in computational protein design," Current Opinion in Structural Biology, Aug. 2004, 14(4):487-494.
Park et al., "Mechanisms of mucoadhesion of poly(acrylic acid) hydrogels," Pharm. Res., 1987, 4(6):457-64.
Parrott et al., "Drug Delivery: Relieving PEGylation," Nature Chemistry, Dec. 2011, 4(1):13-14.
Paterova et al., "Reversal of the Hofmeister Series: Specific Ion Effects on Peptides," J Phys Chem B, 2013, 117(27):8150-8158.
PCT International Preliminary Report on Patentability for International Appln. No. PCT/US2014/035033 issued Oct. 27, 2015.
PCT International Preliminary Report on Patentability in International Appln No. PCT/US2019/044723, dated Feb. 2, 2021, 7 pages.
PCT International Preliminary Report on Patentability in International Appln. No. PCT/US2019/044743, dated Feb. 2, 2021, 7 pages.
PCT International Preliminary Report on Patentability in International Appln. No. PCT/US2018/013552, dated Jul. 16, 2019, 9 pages.
PCT International Preliminary Report on Patentability in International Appln. No. PCT/US2018/044859, dated Feb. 4, 2020, 9 pages.
PCT International Search Report and Written Opinion for International Appln. No. PCT/US2016/017351 dated, Apr. 21, 2016, 9 pages.
PCT International Search Report and Written Opinion in International Appln No. PCT/US2019/044723, dated Dec. 5, 2019, 11 pages.
PCT International Search Report and Written Opinion in International Appln No. PCT/US2019/044743, dated Oct. 16, 2019, 9 pages.
PCT International Search Report and Written Opinion in International Appln . No. PCT/US2018/013552, dated Aug. 14, 2018, 17 pages.
PCT International Search Report and Written Opinion in International Appln. No. PCT/US19/44723, dated Dec. 5, 2019, 12 pages.
PCT International Search Report and Written Opinion in International Appln. No. PCT/US19/44742, dated Oct. 16, 2019, 15 pages.
PCT International Search Report and Written Opinion in International Appln. No. PCT/US2014/035033, dated Aug. 28, 2014.
PCT International Search Report and Written Opinion in International Appln. No. PCT/US2018044859, dated Oct. 22, 2018, 12 pages.
PCT Invitation to Pay Fees in International Appln. No. PCT/US19/44723, dated Sep. 20, 2019, 2 pages.
Peeler et al., "Genetically Encoded Initiator for Polymer Growth from Proteins," Journal of the American Chemical Society, 2010, 132(39): 13575-13577.

(56) References Cited

OTHER PUBLICATIONS

Pelegri-Oday et al., "Therapeutic Protein-Polymer Conjugates: Advancing Beyond PEGylation," Journal of the American Chemical Society, Dec. 2014, 136(41):14323-14332.
Perry et al., "PEGylated PRINT Nanoparticles: The Impact of PEG Density on Protein Binding, Macrophage Association, Biodistribution, and Pharmacokinetics," Nano Letters, Aug. 2012, 12(10):5304-5310.
Perutz, "Electrostatic effects in proteins," Science, Sep. 1978, 201(4362): 1187-1191.
Pettersen et al., "UCSF Chimera—a visualization system for exploratory research and analysis," J. Comput. Chem., 2004, 25(13):1605-12.
Pham et al., "Fenton-like copper redox chemistry revisited: Hydrogen peroxide and superoxide mediation of copper-catalyzed oxidant production," J. Catalysis, 2013, 301:54-64.
Pokala et al., "Review: protein design—where we were, where we are, where we're going," Journal of Structural Biology, 2001, 134(2-3):269-281.
Polymer Science: A Comprehensive Reference, Eds., 2012;377-428.
Porath, "Immobilized Metal Ion Affinity Chromatography," Protein Expr. Purif., 1992, 3(4):263-281.
Price et al., "Surface charge measurements on Micrococcus lysodeikticus and the catalytic implications for lysozyme," Biochimica et Biophysica Acta (BBA)—Molecular Cell Research, Nov. 1986, 889(2):128-135.
Qi et al., "A brush-polymer/exendin-4 conjugate reduces blood glucose levels for up to five days and eliminates poly(ethylene glycol) antigenicity," Nat. Biomed. Eng., 2016, 1(1):1-12.
Qi et al., "PEGylated porcine glucagon-like peptide-2 improved the intestinal digestive function and prevented inflammation of weaning piglets challenged with LPS," Animal, 2015, 9(9):1481-9.
Qi et al., "Sortase-Catalyzed Initiator Attachment Enables High Yield Growth of a Stealth Polymer from the C Terminus of a Protein," Macromolecular Rapid Communications, 2013, 34(15): 1256-1260.
Qiu et al., "Polymerization of Substituted Styrenes by Atom Transfer Radical Polymerization," Macromolecules, Sep. 1997, 30(19):5643-5648.
Qiu et al., "Controlled/living radical polymerization in aqueous media: homogeneous and heterogeneous systems," Progress in Polymer Science, Dec. 2001, 26(10):2083-2134.
Radestock et al., "Exploiting the Link between Protein Rigidity and Thermostability for Data-Driven Protein Engineering," Engineering in Life Sciences, Oct. 2008, 8(5):507-522.
Radic et al., "Catalytic detoxification of nerve agent and pesticide organophosphates by butyrylcholinesterase assisted with non-pyridinium oximes," Biochem. J., 2013, 450(1):231-242.
Reineke et al., "Can bioadhesive nanoparticles allow for more effective particle uptake from the small intestine?," J. Controlled Release, 2013, 170(3):477-484.
Riccardi et al., "Toward "stable-on-the-table" enzymes: improving key properties of catalase by covalent conjugation with poly(acrylic acid)," Bioconjugate Chem., 2014, 25(8):1501-10.
Riener et al., "Quick measurement of protein sulfhydryls with Ellman's reagent and with 4,4'-dithiodipyridine," Anal Bioanal Chem, 2002, 373(4-5):266-276.
Robinson et al., "Copper Metallochaperones," Ann. Rev. Biochem., 2010, 79(1):537-562.
Röcker et al., "The use of glucose oxidase and catalase for the enzymatic reduction of the potential ethanol content in wine," Food Chemistry, 2016, 210:660-670.
Rodriguez et al., "Site-directed mutagenesis improves catalytic efficiency and thermostability of *Escherichia coli* pH 2.5 acid phosphatase/phytase expressed in Pichia pastoris," Arch. Biochem. Biophys., 2000, 382(1):105-12.
Rodríguez-Martínez et al., "Enzymatic activity and thermal stability of PEG-a-chymotrypsin conjugates," Biotechnol. Lett., 2009, 31(6):883-887.
Rodríguez-Martínez, et al., "Stabilization of a-Chymotrypsin Upon PEGylation Correlates With Reduced Structural Dynamics," Biotechnol. Bioeng., 2008, 101(6):1142-1149.
Russell et al., "Rational Modification of enzyme catalysis by engineering surface charge," Nature, 1987, 328(6130):496-500.
Russell et al., "Electrostatic Effects on Modification of Charged Groups in the Active Site Cleft of Subtilisin by Protein Engineering," Mol. Biol. 1987, 193(4):803-813.
Sandanaraj et al., "Noncovalent Modification of Chymotrypsin Surface Using an Amphiphilic Polymer Scaffold: Implications in Modulating Protein Function," J Am Chem Soc, 2005, 127:10693-10698.
Sanderova et al., "The N-terminal Region Is Crucial for the Thermostability of the G-domain of Bacillus Stearothermophilus EF-Tu," Biochim. Biophys. Acta., 2010, 1804(1):147-155.
Scheidig et al., "Crystal structures of bovine chymotrypsin and trypsin complexed to the inhibitor domain of Alzheimer's amyloid beta-protein precursor (APPI) and basic pancreatic trypsin inhibitor (BPTI): engineering of inhibitors with altered specificities," Protein Sci., 1997, 6(9):1806-24.
Schild, "Poly(N-Isopropylacrylamide): Experiment, Theory and Application," Prog. Polym., Sci. 1992, 17(2):163-249.
Schröder et al., "Substituted Tris(2-pyridylmethyl)amine Ligands for Highly Active ATRP Catalysts," ACS Macro Letters, 2012, 1(8):1037-1040.
Schulz et al., "Site-Specific Polymer Conjugation Stabilizes Therapeutic Enzymes in the Gastrointestinal Tract," Adv. Mater., 2016, 28(7):1455-1460.
Shakya et al., "An update on smart biocatalysts for industrial and biomedical applications," Journal of Royal Society Interface, Feb. 2018, 15(139): 1-15.
Shan et al., "Chloride accelerated Fenton chemistry for the ultrasensitive and selective colorimetric detection of copper," Chem. Commun., 2016, 52(10):2087-2090.
Shental-Bechor et al., "Effect of glycosylation on protein folding: A close look at thermodynamic stabilization," PNAS. Jun. 2008, 105(24):8256-8261.
Shoichet et al., "A relationship between protein stability and protein function.," Proc. Natl. Acad Sci. USA, 1995, 92(2):452-456.
Simakova et al., "Aqueous ARGET ATRP," Macromol., 2012, 45(16):6371-6379.
Simon et al., "Structure and activity of alpha-chymotrypsin and trypsin in aqueous organic media," Biochem. Biophys. Res. Commun., 2001, 280(5)1367-71.
Sioud et al., "Cationic liposome-mediated delivery of siRNAs in adult mice," Biochemical and Biophysical Research Communications 2003, 312(4):1220-1225.
Smart, "The basics and underlying mechanisms of mucoadhesion," Adv. Drug Delivery Rev., 2005, 57(11):1556-68.
Smith et al., "Vascular Catheters with a Nonleaching Poly-Sulfobetaine Surface Modification Reduce Thrombus Formation and Microbial Attachment," Sci. Transl. Med., 2012, 4(153):153ra132.
Smolelis et al., "The Determination of Lysozyme," Journal of Bacteriology, Sep. 1949, 58(6):731-726.
Sola et al., "Glycosylation of Therapeutic Proteins," BioDrugs, Aug. 2010, 24(1):9-21.
Somaraju et al., "Pancreatic enzyme replacement therapy for people with cystic fibrosis," Cochrane Db. Syst. Rev., 2014, 13(10):CD008227.
Stepankova et al., "Strategies for Stabilization of Enzymes in Organic Solvents," ACS Catalysis 2013, 3(12);2823-2836.
Street et al., "A molecular mechanism for osmolyte-induced protein stability," P. Natl. Acad. Sci. U.S.A., 2006, 103(38):13997-4002.
Strozyk et al., "Protein/Polymer-Based Dual-Responsive Gold Nanoparticles with pH-Dependent Thermal Sensitivity," Adv. Funct. Mater., 2012, 22(7):1436-1444.
Su et al. "Catechol Polymers for pH-Responsive, Targeted Drug Delivery to Cancer Cells," J. Am. Chem. Soc., 2011, 133(31):11850-11853.
Suckau et al., "Protein surface topology-probing by selective chemical modification and mass spectrometric peptide mapping," Proceedings of the National Academy of Sciences of the USA, Jun. 1992, 89(12):5630-5634.

(56) References Cited

OTHER PUBLICATIONS

Tan et al., "Enzyme-Assisted Photoinitiated Polymerization-Induced Self-Assembly: An Oxygen-Tolerant Method for Preparing Block Copolymer Nano-Objects in Open Vessels and Multiwell Plates," Macromolecules, 2017, 50(15):5798-5806.

Tang et al., "Effects of Initiator Structure on Activation Rate Constants in ATRP," Macromol., 2007, 40(6):1858-1863.

Tang et al., "N-succinimidyl propionate: Characterisation and optimum conditions for use as a tritium labelling reagent for proteins," Journal of Labelled Compounds and Radiopharmaceuticals, Feb. 1983, 20(2): 277-284.

Taverna et al., "Why are proteins marginally stable?," Proteins, Nov. 2002, 46(1):105-109.

Taylor et al., "Acetylcholinesterase: Converting a vulnerable target to a template for antidotes and detection of inhibitor exposure," Toxicology, 2007, 233(1-3):70-78.

Taylor, "Chapter 6, Anticholinesterase Agents," Goodman and Gillman's The Pharmacological Basis of Therapeutics, 7th Ed., Macmillan Publishing Company, NY, 1985, pp. 110-129.

Teodorescu et al., "Atom Transfer Radical Polymerization of (Meth)acrylamides," Macromol., 1999, 32(15):4826-4831.

Terrier et al., "Revisiting the reactivity of oximate α-nucleophiles with electrophilic phosphorus centers. Relevance to detoxification of sarin, soman and DFP under mild conditions," Organic & Biomolecular Chemistry, 2006, 4(23):4352-4363.

Thilakarathne et al., "Protein Polymer Conjugates: Improving the Stability of Hemoglobin with Poly(acrylic acid)," Langmuir, May 2011, 27(12):7663-7671.

Thomas et al., "Tailoring the pH dependence of enzyme catalysis using protein engineering," Nature, 1985, 318(6044):375-376.

Timasheff, "Protein-solvent preferential interactions, protein hydration, and the modulation of biochemical reactions by solvent components," P. Natl. Acad. Sci. U.S.A., 2002, 99(15):9721-6.

Trapnell et al., "Relationship Between Pancreatic Enzyme Replacement Therapy and Healthcare Use In Children with Cystic Fibrosis," M. Pediatr. Pulm., 2014, 49:406-407.

Trzebicka et al., "Thermoresponsive polymer-peptide/protein conjugates," Progress in Polymer Science, May 2017, 68:35-76.

Tsarevsky et al., "Deactivation Efficiency and Degree of Control over Polymerization in ATRP in Protic Solvents," Macromolecules, 2004, 37(26):9768-9778.

Turner et al., "Stabilization of a supplemental digestive enzyme by post-translational engineering using chemically-activated polyethylene glycol," Biotechnol. Lett., 2011, 33(3):617-621.

Uchida et al., "Topography of Polymer Chains Grafted on a Polymer Surface Underwater," Macromolecules, 1997, 30(18):5464-5469.

Ugarova et al., "Chemical modification of the -amino groups of lysine residues in horseradish peroxidase and its effect on the catalytic properties and thermostability of the enzyme," Biochimica et Biophysica Acta (BBA)—Enzymology, Sep. 1979, 570(1):31-42.

Van de Wetering et al., "A Mechanistic Study of the Hydrolytic Stability of Poly(2-(dimethylamino)ethyl methacrylate)," Macromolecules, 1998, 31:8063-8068.

Van Hooidonk et al., "On the reactivity of organophosphorus compounds Part IV. The alkaline hydrolysis of some O-phosphorylated 2-pyridine oximes," Rec. Trav. Chim. 1968, 87(6):673-686.

Van Leemputten et al., "Soluble-Insoluble Complex of Trypsin Immobilized on Acrolein-Acrylic Acid Copolymer," Biotech. Bioeng., 1976, 18(4):587-590.

Venkataraman et al., "ATRP from an amino acid-based initiator: A facile approach for α-functionalized polymers," Macromolecules, 2006, 39(26):9661-9664.

Veronese et al., "PEGylation, successful approach to drug delivery," Drug Discovery Today, 2005, 10(21):1451-1458.

Veronese et al., "The impact of PEGylation on biological therapies," BioDrugs, 2008, 22(5): 315-329.

Veronese, "Peptide and Protein PEGylation: a review of problems and solutions," Biomaterials, 2001, 22(5):405-417.

Wang et al., "A Novel Mechanism of Protein Thermostability: A Unique N-terminal Domain Confers Heat Resistance to Fe/Mn-SODs," Sci. Rep., 2014, 4:7284.

Wang et al., "Controlled/"living" radical polymerization. atom transfer radical polymerization in the presence of transition," J. Am. Chem. Soc., 1995, 117(20):5614-5615.

Wang et al., "Enhancing Accuracy in Molecular Weight Determination of Highly Heterogeneously Glycosylated Proteins by Native Tandem Mass Spectrometry," Analytical Chemistry, 2017, 89(9):4793-4797.

Wang et al., "Improving the Protein Activity and Stability Under Acidic Conditions via Site-Specific Conjugation of a pH-Responsive Polyelectrolyte," Journal of Materials Chemistry B, Jan. 2015, 3(3):498-504.

Wang et al., "Structural and biological characterization of pegylated recombinant interferon alpha-2b and its therapeutic implications," Advanced Drug Delivery Reviews, Jun. 2002, 54(4):547-570.

Wang et al., "Tuning the molecular size of site-specific interferon-polymer conjugate for optimized antitumor efficacy," Science China Materials, Jun. 2017, 60(6):563-570.

Wang et al., "Functional protein-organic/inorganic hybrid nanomaterials," Wiley Interdisciplinary Reviews: Nanomedicine and Nanobiotechnology, 2013, 5(4):320-328.

Wang, "Lyophilization and development of solid protein pharmaceuticals," Int. J. Appl. Pharm., 2000, 203(1-2):1-60.

Ward et al. "Thermostable Enzymes," Biotechnol. 1988, Adv., 6(1):39-69.

Watson, "Exocrine insufficiency and pancreatic enzyme replacement therapy in pancreatic cancer," Clin. Oncol. (R Coll Radiol), 2010, 22(5):391.

Weaver, et al. "Synthesis and aqueous solution properties of a well-defined thermo-responsive schizophrenic diblock copolymer," Chem. Commun., 2002, 18:2122-2123.

Webb, "Drugmakers dance with autism," Nat. Biotechnol., 2010, 28(8):722-4.

Welinder et al., "Effects of glycosylation on protein folding, stability and solubility. Studies of chemically modified or engineered plant and fungal peroxidases," Progress in Biotechnology, 1995, 10:205-210.

Wenck et al., "A Noncovalent Switch for Lysozyme," Journal of the American Chemical Society, 2007, 129(51):16015-16019.

Werle, "Strategies to improve plasma half life time of peptide and protein drugs," Amino Acids, 2006, 30(4):351-67.

Wever et al., "Acrylamide Homopolymers and Acrylamide-N-Isopropylacrylamide Block Copolymers by Atomic Transfer Radical Polymerization in Water," Macromolecules, May 2012, 45(10):4040-4045.

Wijmans et al., "Polymer Brushes at Curved Surfaces," Macromolecules, 1993, 26(26): 7214-7224.

Williams et al., "Strategies for Biophysical Characterization of Protein-Polymer Conjugates," Nano Armoring of Enzymes: Rational Design of Polymer-Wrapped Enzymes, 2017, 590:93-114.

Wilson, "Synthesis and Applications of Protein/Peptide-Polymer Conjugates," Macromol. Chem. Phys., 2017, 218(9):1600595.

Written Opinion of the International Searching Authority for International Appln. No. PCT/US2014/035033, dated Aug. 28, 2014, 5 pages.

Wysocka et al., "Designing of Substrates and Inhibitors of Bovine α-Chymotrypsin with Synthetic Phenylalanine Analogues in Position P1," Protein Pept. Lett., 2008, 15(3):260-264(5).

Xenos et al., "Treatment of lactose intolerance with exogenous beta-D-galactosidase in pellet form," Eur. J. Drug Metab. Ph., 1998, 23(2):350-5.

Xiao et al., "Rational modification of protein stability by targeting surface sites leads to complicated results," Proc. Natl. Acad Sci. USA, Jul. 2013, 110(28): 11337-11342.

Xu et al., "Scalable method to produce biodegradable nanoparticles that rapidly penetrate human mucus," J. Controlled Release, 2013, 170(2):279-286.

(56) References Cited

OTHER PUBLICATIONS

Yang et al., "Polyethylene glycol-induced stabilization of subtilisin," Enzyme Microb. Technol., 1996, 18(2):82-89.

Yaphe, "The Use of Agarase From Pseudomonas Atlantica in the Identification of Agar in Marine Algae (Rhodophyceae)," Can. J Microbial., 1957, 3(7):987-993.

Yaayan et al., "Responsive hybrid block co-polymer conjugates of proteins-controlled architecture to modulate substrate specificity and solution behavior," C. Polym. Chem., 2011, 2(7):1567-1578.

Yin et al., "Drug permeability and mucoadhesion properties of thiolated trimethyl chitosan nanoparticles in oral insulin delivery," Biomaterials, 2009, 30(29):5691-700.

Zeikus et al., "Thermozymes: biotechnology and structure-function relationships," Trends Biotechnol., 1996, 14(6):83-190.

Zhang et al., "Interactions Between Macromolecules and Ions: The Hofmeister Series," Curr. Opin. Chem. Biol., 2006, 10(6):658-663.

Zhang et al., "On the role of electrostatics in protein—protein interactions," Physical Biology, May 2011, 8(3):35001.

Zhang et al., "Effects of Hofmeister Anions on the LCST of PNIPAM as a Function of Molecular Weight," J. Phys. Chem. C 2007, 111(25):8916-8924.

Zhang et al., "Enhanced catalytic activity in organic solvents using molecularly dispersed haemoglobin-polymer surfactant constructs," Chem Commun. 2013, 49(83):9561-9563.

Zhang et al., "Polysulfobetaine-Grafted Surfaces as Environmentally Benign Ultralow Fouling Marine Coatings," Langmuir, 2009, 25(23):13516-13521.

Zhao et al., "Synthesis of well-defined protein-polymer conjugates for biomedicine," Polymer, 2015, 66:A1-A10.

Zhou et al., "Electrophoretic separation of DNA using a new matrix in uncoated capillaries," J. Chromatography A, 2005, 1083(1-2):173-178.

U.S. Appl. No. 14/785,868, filed Oct. 21, 2015, Alan J. Russell.
U.S. Appl. No. 15/026,093, filed Mar. 30, 2016, Alan J. Russell.
U.S. Appl. No. 15/549,852, filed Aug. 9, 2017, Alan J. Russell.
U.S. Appl. No. 16/477,843, filed Jul. 12, 2019, Alan J. Russell.
U.S. Appl. No. 16/635,343, filed Jan. 30, 2020, Hironobu Murata.
U.S. Appl. No. 16/520,008, filed Jul. 23, 2019, Krzysztof Matyjaszewski.
U.S. Appl. No. 17/264,519, filed Jan. 29, 2021, Alan J. Russell.

Kreutzer, "Atom-Transfer Radical Polymerization: New Method Breathes Life Into ATRP," Nature Reviews Chemistry, 2018, 2(2):0111.

Becker et al. "Functional micellar assemblies prepared via block copolymers synthesized by living free radical polymerization upon peptide-loaded resins," Biomacromolecules, 2005, 6:220-228.

* cited by examiner

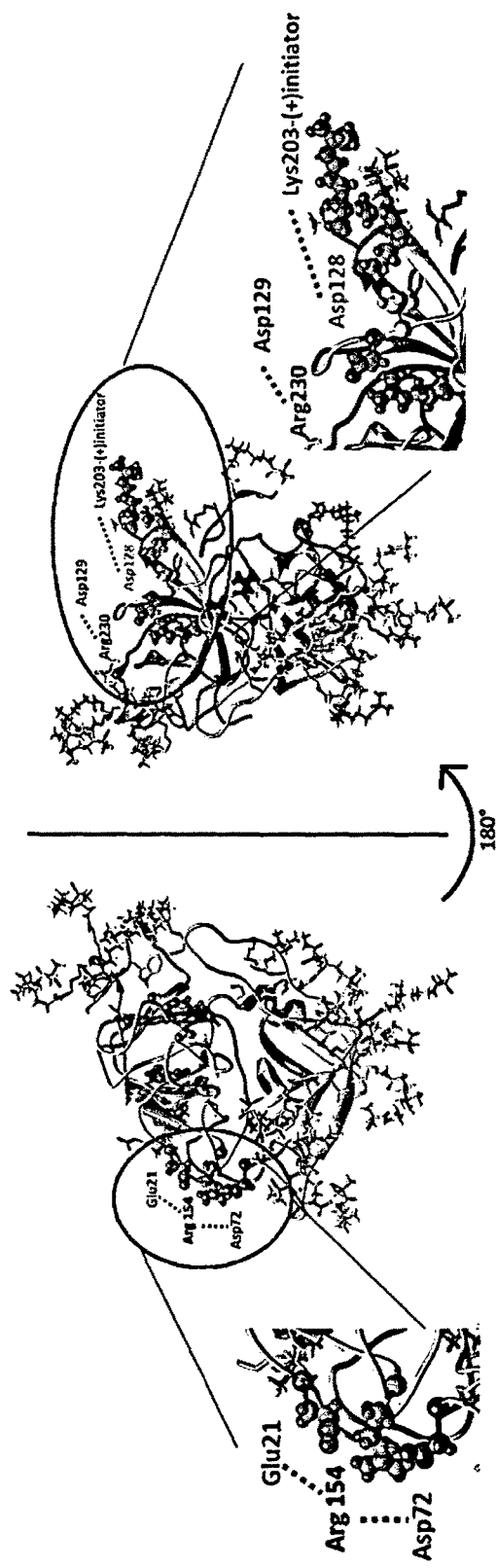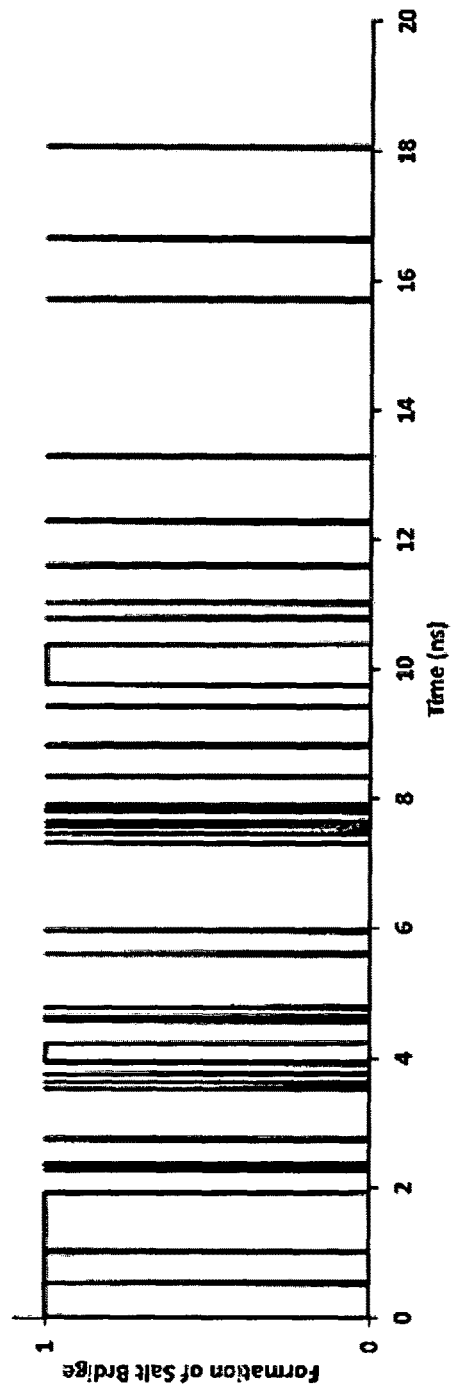
FIG. 10A
FIG. 10B

AMINO-REACTIVE POSITIVELY CHARGED ATRP INITIATORS THAT MAINTAIN THEIR POSITIVE CHARGE DURING SYNTHESIS OF BIOMACRO-INITIATORS

CROSS-REFERENCE TO RELATED APPLICATIONS

This application is a National Phase Application under 35 U.S.C. § 371 of International Application No. PCT/US2019/044743, filed on Aug. 1, 2019, which claims priority from U.S. Provisional Application Ser. No. 62/764,395, filed Aug. 1, 2018, which is incorporated by reference herein in its entirety.

TECHNICAL FIELD

This document relates to materials and methods that can facilitate atom transfer radical polymerization (ATRP) reactions, and more particularly to ATRP initiator molecules that maintain a positive charge during biomacro-initiator synthesis.

BACKGROUND

The delicate balance of forces that maintain the structure, function and dynamics of enzymes is at the heart of their remarkable activity and bothersome instability (Taverna and Goldstein, *Proteins* 2002, 46(1):105-109). Although some enzymes have evolved to survive in extreme environments (Calligari et al., *J. Phys. Chem. B* 2015, 119(25):7860-7873), protein engineers that desire to stabilize proteins for therapeutic or industrial use have generally used molecular biology to dramatically improve function (de Champdoré et al., *J. R. Soc. Interface* 2007, 4(13):183-191; Coker, *F1000Research* 2016, 5; and Radestock and Gohlke, *Eng. Life Sci.* 2008, 8(5):507-522). Another compelling approach to protein/enzyme stabilization has used covalently attached polymers to impart stability. Polymers such as polyethylene glycol (PEG) can be covalently coupled to the surface of an enzyme (commonly referred to as PEGylation) or grown from the surface of proteins using controlled radical polymerization from protein-initiator complexes. Protein-initiator complexes are most often formed by reacting accessible surface amino groups with activated ester alkyl halides. These reactions, and almost all PEGylation coupling chemistries, sacrifice the native electrostatic environment of the protein surface for the supposed benefit of the resulting conjugate.

The prevailing view of protein scientists has been that maintaining protein surface charge-charge interactions is less important to protein stability that maintaining the integrity of the hydrophobic core. Indeed, the hydrophobic interactions within a protein contribute hundreds of kJ mol$^{-1}$ to maintaining a folded conformation, whereas exposed surface charge-charge interactions only contribute a few kJ mol$^{-1}$ (Pace et al., *FEBS Lett.* 2014, 588(14):2177-2184; Dill, *Biochemistry* 1990, 29(31):7133-7155; Zhang et al., *Phys. Biol.* 2011, 8(3):35001; and Pace et al., *FASEB J.* 1996, 10(1):75-83). Surprisingly, however, rationally optimizing charge-charge interactions, both experimentally and computationally as a predictive tool, is still an effective strategy in designing proteins with high stability (Park et al., *Curr. Opin. Struct. Biol.* 2004, 14(4):487-494; Dwyer et al., *Science* 2004, 304(5679):1967-1971; and Lee et al., *Biochemistry* 2005, 44:16817-16825). It also has been observed that long-range electrostatic interactions are as important as short-range salt bridge interactions (Lee et al., supra). Additionally, charge-charge interactions can either be optimized by increasing favorable electrostatic interactions or by decreasing the number of unfavorable electrostatic interactions (Koide et al., *Biochemistry* 40:10326-10333). Conversely, others have questioned whether charge-charge interactions are important influencers of stability (Loladze and Makhatadze, *Protein Sci.* 2002, 11(1):174-177; Hollecker and Creighton, *Biochim. Biophys. Acta—Protein Struct. Mol. Enzymol.* 1982, 701(3):395-404; Xiao et al., *Proc. Natl. Acad. Sci. USA* 2013, 110(28):11337-11342; Ugarova et al., *Biochim. Biophys. Acta—Enzymol.* 1979, 570(1):31-42; and Perutz, *Science* 1978, 201(4362):1187-1191). It is not surprising, therefore, that the protein-polymer conjugate community has all but ignored the impact of polymer attachment chemistry on surface charge.

Protein modification is not only used to increase protein robustness, but also to diversify functionality and modulate activity (Radestock and Gohlke, supra; Pokala and Handel, *J. Struct. Biol.* 2001, 134(2-3):269-281; Shoichet et al., *Proc. Natl. Acad. Sci. USA* 1995, 92(2):452-456; and Thilakarathne et al., *Langmuir* 2011, 27(12):7663-7671). The human body does this naturally through post-translational modification (e.g., by glycosylation, phosphorylation, lipidation, and/or nitrosylation). For example, glycosylation introduces sugar moieties to the surfaces of proteins which alters protein folding, stability, solubility, and dynamics (Shental-Bechor and Levy, *Proc. Natl. Acad. Sci. USA* 2008, 105(24):8256-8261; Sold and Griebenow, *BioDrugs* 2010, 24(1); 9-21; Welinder et al., *Prog. Biotechnol.* 1995, 10:205-210; and Lee et al., *Sci. Rep.* 2015, 5:892).

Over the past four decades, scientists have engineered proteins with covalently attached synthetic polymers for a variety of therapeutic and industrial applications (Cummings et al., *ACS Macro Lett.* 2016, 5(4):493-497; Murata et al., *Biomacromolecules* 2013, 14(6):1919-1926; Veronese et al., *Drug Discov. Today* 2005, 10(21):1451-1458; Cummings et al., *Biomacromolecules* 2017, 18(2):576-586; Parrott et al., *Nat. Chem.* 2011, 4(1):13-14; Lozano et al., *Biotechnol. Bioeng.* 2001, 75(5):563-569; Huang et al., *ACS Appl. Mater. Interfaces* 2015, 7(27):14660-14669; Campbell et al., *Electrochim. Acta* 2017, 248:578-584; and Shakya and Nandakumar, *J. Roy. Soc. Interface* 2018, 15(139):1-15). Of the twelve FDA-approved therapeutic protein-polymer conjugates, only one maintained surface charge during PEG attachment (Pelegri-Oday et al., *J. Am. Chem. Soc.* 2014, 136(41):14323-14332). In grafting-from protein-polymer conjugate synthesis, where initiators are first attached to targeted sites on the protein surface from which controlled radical polymerization occurs, surface charge has also been ignored (Lele et al., *Biomacromolecules* 2005, 6(6):3380-3387; Kovaliov et al., *Polymer (Guildf)*. 2018, 137:338-345; and Paeth et al., *Methods Enzymol.* 2017, 590:193-224). ATRP has been used to grow dense polymer coatings that "nano-armor" proteins (Matyjaszewski and Tsarevsky, *J. Am. Chem. Soc.* 2014, 136(18):6513-6533; and Averick et al., *ACS Macro Lett.* 2012, 1(1):6-10). A wide variety of polymers with a broad range of molecular weights and densities have been conjugated with proteins to determine their impact on function, including random copolymers (Panganiban et al., *Science* 2018, 359(6381):1239-1243), block copolymers (Kulkarni et al., *Biomacromolecules* 2006, 7(10):2736-2741; Huang et al., supra; and Cummings et al., *Biomacromolecules* 2014, 15(3):763-771), thermo-responsive polymers (Murata et al., supra; Huang et al., supra; and Trzebicka et al., *Prog. Polym. Sci.* 2017, 68:35-76), pH-responsive polymers (Cummings et al., *Biomateri-*

*als* 2013, 34(30):7437-7443), branched polymers (Gauthier and Klok, *Polym. Chem.* 2010, 1(9):1352), and charged polymers (Cummings 2017, supra; Lucius et al., *Biomacromolecules* 2016, 17(3):1123-1134; and Bhattacharjee et al., *ChemBioChem* 2015, 16(17):2451-2455). The charge of the ATRP-initiator has never been explored.

SUMMARY

Rational design of protein-polymer conjugates by protein-ATRP has remained elusive because the polymers can have unpredictable effects on the activity and stability of the formed bioconjugates. For the most part, the assumption has been that the physicochemical properties of the polymer dominate the resulting bioactivity and stability. Molecular dynamics simulations have shown, however, that the polymer rarely interacts intimately. Attention therefore has focused on the interface between the polymer and the protein and, in particular, on maintaining the electrostatic environment at the surface of enzymes during the growth of polymers.

This document is based on the development of a novel, amino-reactive, positively charged ATRP initiator that maintains its permanent positive charge during the synthesis of biomacro-initiators. Enzymatic macro-initiators generated as described herein maintained surface charge and suffered none of the deleterious effects on activity and stability exhibited by their counterparts generated with a neutral initiator. Further, this document is based, at least in part, on the discovery that maintaining the electrostatic environment during initiation can protect enzyme activity during and after the growth of protein-compatible polymers, as well as polymers that typically inactivate proteins. Embodiments include the positively charged N-hydroxysuccinimidyl ester protein-ATRP-initiator that was synthesized as described herein, as well as methods for using such initiators in the design and synthesis of functional protein-polymer conjugate variants.

In a first aspect, this document features a method for generating a protein-initiator conjugate, comprising contacting a protein with an ATRP initiator, where the ATRP initiator includes an amine-reactive group, one or more alkyl halide groups, and a positively charged group. The amine-reactive group can include an active ester (e.g., an N-hydroxysuccinimide ester, a nitrophenol ester, a pentafluorophenol ester, or an oxybenzotriaole ester). The alkyl halide can include bromine or chlorine. The positively charged group can include a quaternary ammonium. The protein can be an enzyme (e.g., an esterase, a lipase, an organophosphate hydrolase, an aminase, an oxidoreductase, a hydrogenase, or lysozyme).

In another aspect, this document features a protein-initiator conjugate containing a protein coupled to an ATRP initiator, where the ATRP initiator includes an amine-reactive group, one or more alkyl halide groups, and a positively charged group. The amine-reactive group can include an active ester (e.g., an N-hydroxysuccinimide ester, a nitrophenol ester, a pentafluorophenol ester, or an oxybenzotriaole ester). The alkyl halide can include bromine or chlorine. The positively charged group can include a quaternary ammonium. The protein can be an enzyme (e.g., an esterase, a lipase, an organophosphate hydrolase, an aminase, an oxidoreductase, a hydrogenase, or lysozyme).

In another aspect, this document features a method for generating a protein-polymer conjugate. The method can include contacting a protein-initiator conjugate with a population of monomers in the presence of a transition metal catalyst or metal-free organic complex that can participate in a redox reaction, where the initiator includes an amine-reactive group, one or more alkyl halide groups, and a positively charged group. The amine-reactive group can include an active ester (e.g., an N-hydroxysuccinimide ester, a nitrophenol ester, a pentafluorophenol ester, or an oxybenzotriaole ester). The alkyl halide can include bromine or chlorine. The positively charged group can include a quaternary ammonium. The protein can be an enzyme (e.g., an esterase, a lipase, an organophosphate hydrolase, an aminase, an oxidoreductase, a hydrogenase, or lysozyme). The monomer can be selected from the group consisting of carboxybetaine methacrylate, (oligo(ethylene glycol) methacrylate), 2-dimethylaminoethyl methacrylate, sulfobetaine methacrylate, 2-(methylsulfinyl)ethyl acrylate, oligo(ethylene oxide) methyl ether methacrylate, and (hydroxyethyl) methacrylate.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 5A indicates residual activities at 50° C. and pH 8, while FIG. 5B shows tryptophan fluorescence emission intensities at 45° C. and pH 8. Increased fluorescence intensity indicated protein unfolding as buried aromatic residues became more exposed to the solvent. FIG. 5C shows residual activities, and FIG. 5D shows tryptophan fluorescence emission intensities at pH 1 and 37° C. Connecting lines are nonlinear fits. Error bars represent standard error of the mean from triplicate measurements. At elevated temperature, the CT-neutral initiator lost all detectable activity within the first 5 minutes, which correlated to rapid unfolding in the tryptophan fluorescence plot. The CT-positive initiator displayed residual activities and conformational stabilities similar to those of native CT, indicating that surface charge was important for maintaining CT's stability. In acid, both the CT-neutral and CT-positive initiators rapidly lost activity, as confirmed with rapid unfolding via tryptophan fluorescence.

FIGS. 10A and 10B illustrate formation of salt bridge analysis of CT fully modified with positive initiators from a 20 ns molecular dynamics simulation. FIG. 10A is a schematic showing salt bridges between acidic and basic residues: Asp 72-Arg 154, Glu 21-Arg 154, Asp 129-Arg 230, and Asp 128-Lys203-positive initiator. FIG. 10B is a graph representation of salt bridge formation, which is indicated by a value of 1 on the y-axis. Four salt bridges were formed, with the most dominant salt bridge occurring between Asp 72-Arg 154.

DETAILED DESCRIPTION

Figure 1:
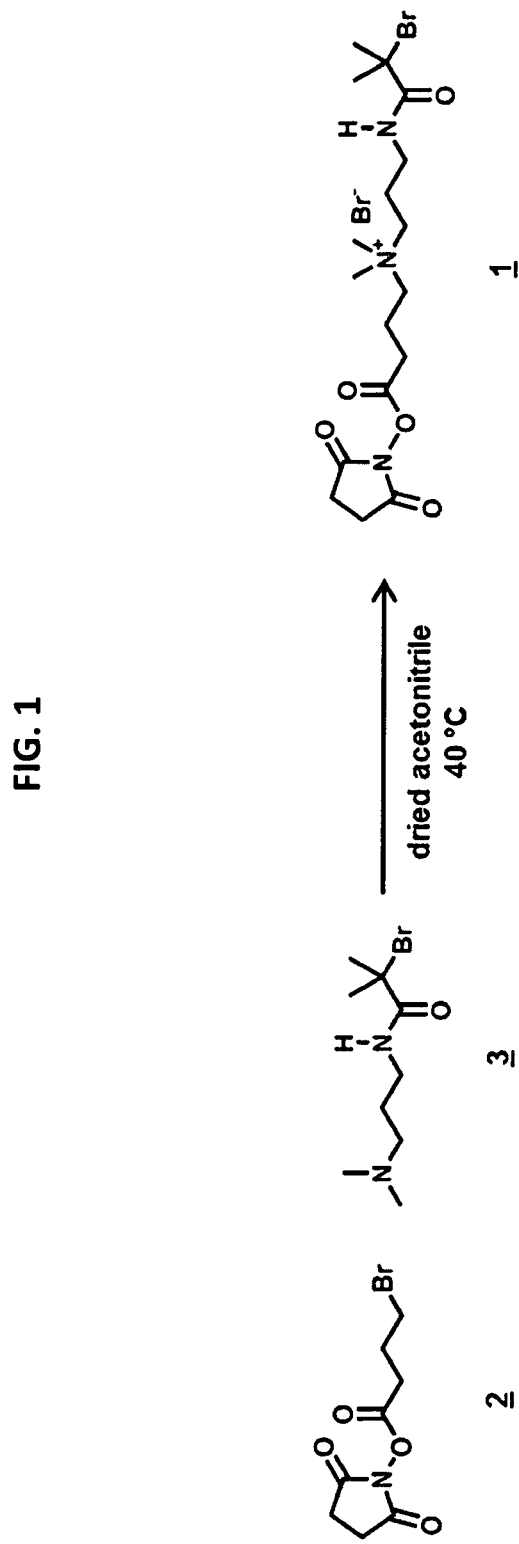
FIG. 1 is a diagram depicting synthesis of positive initiator (1).

ATRP is a type of a reversible-deactivation radical polymerization, and is a means of forming a carbon-carbon bond with a transition metal catalyst. ATRP typically employs an alkyl halide (R—X) initiator and a transition metal complex (e.g., a complex of Cu, Fe, Ru, Ni, or Os) as a catalyst. In an ATRP reaction, the dormant species is activated by the transition metal complex to generate radicals via electron transfer. Simultaneously, the transition metal is oxidized to a higher oxidation state. This reversible process rapidly establishes an equilibrium that predominately is shifted to the side with very low radical concentrations. The number of polymer chains is determined by the number of initiators, and each growing chain has the same probability of propagating with monomers to form living/dormant polymer chains (R—$P_n$—X). As a result, polymers with similar molecular weights and narrow molecular weight distribution can be prepared.

The basic ATRP process and a number of improvements are described elsewhere. See, for example, U.S. Pat. Nos. 5,763,546; 5,807,937; 5,789,487; 5,945,491; 6,111,022; 6,121,371; 6,124,411; 6,162,882; 6,624,262; 6,407,187; 6,512,060; 6,538,091; 6,541,580; 6,624,262; 6,627,314; 6,759,491; 6,790,919; 6,887,962; 7,019,082; 7,049,373; 7,064,166; 7,125,938; 7,157,530; 7,332,550; 7,407,995; 7,572,874; 7,678,869; 7,795,355; 7,825,199; 7,893,173; 7,893,174; 8,252,880; 8,273,823; 8,349,410; 8,367,051;

8,404,788; 8,445,610; 8,816,001; 8,865,795; 8,871,831; 8,962,764; 9,243,274; 9,410,020; 9,447,042; 9,533,297; and 9,644,042; and Publication Nos. 2014/0183055; 2014/0275420; and 2015/0087795.

ATRP also is discussed in a number of publications and reviewed in several book chapters. See, e.g., Matyjaszewski and Zia, Chem. Rev. 2001, 101:2921-2990; Qiu et al., Prog. Polym. Sci. 2001, 26:2083-2134; Wang and Matyjaszewski, J. Am. Chem. Soc. 1995, 117:5614-5615; Coessens et al., Prog. Polym. Sci. 2001, 26:337-377; Braunecker and Matyjaszewski, Prog. Polym. Sci. 2007, 32:93-146; Matyjaszewski, Macromol. 2012, 45:4015-4039; Schroder et al., ACS Macro Letters 2012, 1:1037-1040; Matyjaszewski and Tsarevsky, J. Am. Chem. Soc. 2014, 136:6513-6533; and Kamigaito et al., Chem Rev 2001, 101:3689-3746. Indeed, ATRP can control polymer composition, topology, and position of functionalities within a copolymer (Coessens et al., supra; Advances in Polymer Science; Springer Berlin/Heidelberg: 2002, Vol. 159; Gao and Matyjaszewski, Prog. Polym. Sci. 2009, 34:317-350; Blencowe et al., Polymer 2009, 50:5-32; Matyjaszewski, Science 2011, 333:1104-1105; and Polymer Science: A Comprehensive Reference, Matyjaszewski and Martin, Eds., Elsevier: Amsterdam, 2012; pp 377-428). All of the above-mentioned patents, patent application publications, and non-patent references are incorporated herein by reference to provide background and definitions for the present disclosure.

Monomers and initiators having a variety of functional groups (e.g., allyl, amino, epoxy, hydroxy, and vinyl groups) can be used in ATRP. ATRP has been used to polymerize a wide range of commercially available monomers, including various styrenes, (meth)acrylates, (meth)acrylamides, N-vinylpyrrolidone, acrylonitrile, and vinyl acetate as well as vinyl chloride (Qiu and Matyjaszewski, Macromol. 1997, 30:5643-5648; Matyjaszewski et al, J. Am. Chem. Soc. 1997, 119:674-680; Teodorescu and Matyjaszewski, Macromol. 1999, 32:4826-4831; Debuigne et al., Macromol. 2005, 38:9488-9496; Lu et al., Polymer 2007, 48:2835-2842; Wever et al., Macromol. 2012, 45:4040-4045; and Fantin et al., J. Am. Chem. Soc. 2016, 138:7216-7219). Non-limiting examples of monomers that can be used in ATRP reactions include carboxybetaine methacrylate (CBMA), oligo(ethylene glycol) methacrylate (OEGMA), 2-dimethylaminoethyl methacrylate (DMAEMA), sulfobetaine methacrylate (SBMA), 2-(methylsulfinyl)ethyl acrylate (MSEA), oligo (ethylene oxide) methyl ether methacrylate (OEOMA), and (hydroxyethyl)methacrylate (HEMA).

ATRP can be used to add polymer chains to the surfaces of proteins. An initial step in a protein-ATRP reaction is the addition of initiator molecules to the protein surface. In some cases, ATRP initiators (1) contain an alkyl halide as the point of initiation, (2) are water soluble, and (3) contain a protein-reactive "handle." Alkyl halide ATRP-initiators usually include NHS groups that react with protein primary amines, including the N-terminal and lysine residues. Targeting amino groups can be the best way to achieve the highest polymer coating due to the high abundance of amino groups on protein surfaces. The initiation reaction can be somewhat controlled using carefully designed algorithms that can predict specific reaction rates and sites of the individual amino groups (Carmali et al., ACS Biomater. Sci. Eng. 2017, 3(9):2086-2097).

The amino group at the N-terminus typically has a p$K_a$ in the range of 7.8-8.0, while the p$K_a$'s of lysine side chains range from about 10.5 to 12.0, depending on their local environment (Murata et al., Nat. Commun. 2018, 9, 845). Therefore, at biologically relevant pH values (6-8), the accessible amino groups are positively charged. During ATRP reactions, these positive charges are lost upon initiator attachment, as most (if not all) initiators typically used in ATRP reactions are neutral (see, e.g., Le Droumaguet and Nicolas, Polym. Chem. 2010, 1(5):563; and Broyer et al., Chem. Commun. 2011, 47(8):2212).

Figure 2:
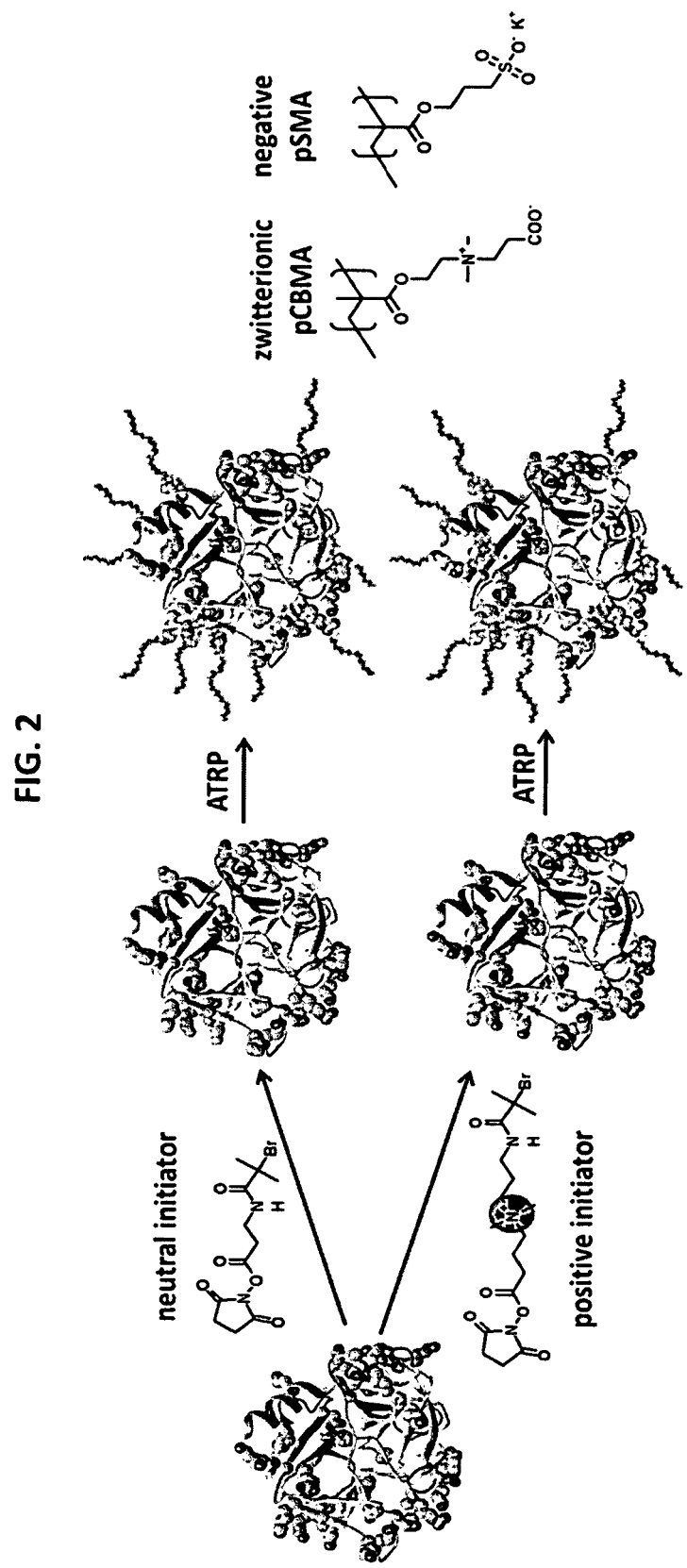
FIG. 2 is a scheme illustrating a synthetic approach to making grafted-from protein-polymer conjugates using neutral or positively charged initiators. The initiators react with primary amino groups on the protein surface through N-Hydroxysuccinimide (NHS) chemistry. ATRP is then performed from the macroinitiators using zwitterionic monomers such as carboxybetaine methacrylate (CBMA) or negatively charged monomers such as sulfonate methacrylate (SMA).

As described herein, the positive charge on a protein surface can be maintained during and after the addition of polymer chains when a positively charged initiator is used. As further described herein, maintaining a positive charge on the protein can permit the protein to maintain its function after polymerization is complete—an important development for therapeutic and industrial protein-polymer conjugates. Thus, this document provides materials and methods for generating protein-polymer conjugates through ATRP while maintaining protein charge and function. In some aspects, for example, this document provides methods for polymer-based engineering of proteins such as the serine protease chymotrypsin, which can be used as a charged initiator on design of enzyme structure, dynamics and function by controlling the kinetics and stability of the chymotrypsin-initiator complexes. As described herein, neutral and positively charged initiators were used to grow poly CBMA (pCMBA) or poly SMA (pSMA) from the surface of various enzymes (FIG. 2). It was shown that pCBMA—a zwitterionic polymer—increased activity and stability, while pSMA—a negatively charged polymer—was devastating to normal function. Conjugates containing these polymers therefore represented best and worst case scenarios when using a neutral ATRP-initiator. Also as described herein, however, when a positively charged initiator was used, enzyme function was retained.

Also described herein are positively charged ATRP-initiators and methods for their synthesis. The positively charged ATRP-initiators can restore the native net charge on an enzyme surface, thereby enhancing activity and stability of the enzyme-initiator complex, as well as the protein-polymer conjugates derived from the enzyme-initiator complex. This document presents the first positively charged ATRP-initiator and demonstrates its impact on the activity and stability of protein-initiator complexes and protein polymer conjugates of enzymes such as α-chymotrypsin (CT), urease, acetylcholinesterase AChE), lysozyme, and avidin. Also described herein are methods for using the positive charge of an ATRP-initiator in the design of highly active and stable protein-polymer conjugate variants.

Figure 14B:
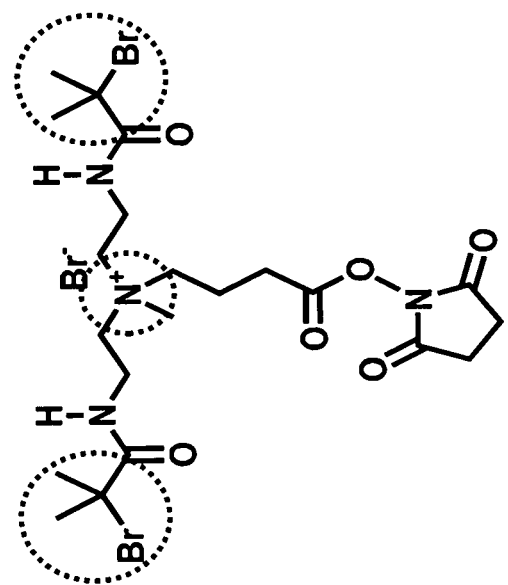
FIGS. 14A-14C are diagrams showing the structure of a "single headed" positively charged ATRP initiator from which one grafting polymer chain can be grown (FIG. 14A), a positively charged "multiple headed" ATRP initiator from which two grafting polymer chains can be grown (FIG. 14B), and a positively charged "multiple headed" ATRP initiator from which four grafting polymer chains can be grown (FIG. 14C). The positions of the positive charges and the initiator heads are circled.
Figure 14A:
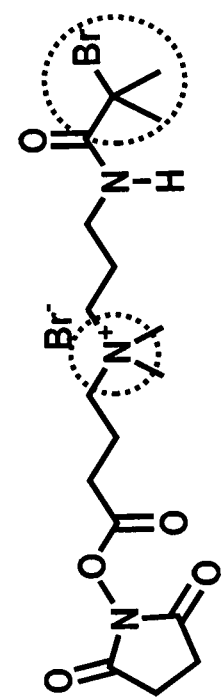
Figure 14C:
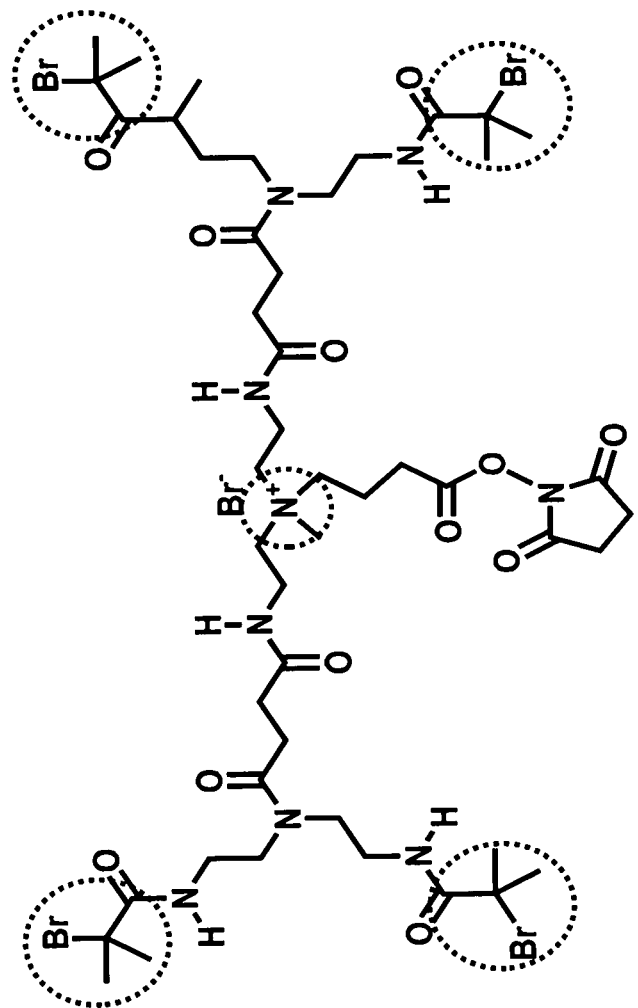

Any appropriate ATRP initiator can be used in the methods provided herein. Suitable initiators can be based on, for example, 2-bromopropanitrile (BPN), ethyl 2-bromoisobutyrate (BriB), ethyl 2-bromopropionate (EBrP), methyl 2-bromopropionate (MBrP), 1-phenyl ethylbromide (1-PEBr), tosyl chloride (TsCl), 1-cyano-1-methylethyldiethyldithiocarbamte (MANDC), 2-(N,N-diethyldithiocarbamyl)-isobutyric acid ethyl ester (EMADC), dimethyl 2,6-dibromoheptanedioate (DMDBHD), 2-chloro-2-methypropyl ester (CME), 2-chloropropanitrile (CPN), ethyl 2-chloroisobutyrate (CliB), ethyl 2-chloropropionate (EC1P), methyl 2-chloropropionate (MC1P), dimethyl 2,6-dichloroheptanedioate (DMDC1HD), or 1-phenyl ethylchloride (1-PEC1), provided that the initiator includes a group with a positive charge (in addition to an amine-reactive group and an alkyl halide or other group that can react with a monomer to initiate polymer addition to the protein). As described in the Examples below, for example, neutral initiator molecules such as those listed above can be modified by reaction with N-(3-N',N'-dimethylaminopropyl)-2-bromo-2-methylpropanamide in the presence of acetonitrile (FIG. 1), resulting in a molecule with an amine-reactive group, an alkyl halide from which monomer addition can be initiated, and a positively charged quaternary ammonium group. In some cases, a positively charged initiator can have a single alkyl halide group from which to initiate polymer growth (FIG. 14A), while in other cases, a positively charged initiator can have two or more (e.g., two, three, four, five, six, or more than six) alkyl halide groups from which to initiate polymer growth. See, e.g., FIGS. 14B and 14C. For example, a protein surface active, positively charged, multitude-headed ATRP initiator can be synthesized from dimethylalkylamine and an alkylbromide containing an active ester such as N-oxysuccinimide.

In some embodiments, this document provides protein-initiator conjugates in which a protein is coupled to a controlled radical polymerization (CRP) (e.g., ARTP) initiator having an amine-reactive group, one or more alkyl halide groups, and a positively charged group. The amine-reactive group can react with amine groups on a protein surface, while the alkyl halide can react with a monomer to initiate polymerization. Any suitable amine-reactive group can be used. Examples of appropriate amine-reactive groups include active esters (e.g., N-hydroxysuccinimide ester, nitrophenol ester, pentafluorophenol ester, can oxybenzotriaole ester). Further, any suitable alkyl halide can be used. In some cases, the alkyl halide can include a bromine or a chlorine atom. Moreover, any suitable group can provide the positive charge to an initiator used in the methods provided herein. In some cases, for example, the positively charged group can include a quaternary ammonium.

Also provided herein are methods for generating protein-initiator conjugates, where the methods include contacting a protein with a positively charged CRP initiator. The initiator include can have an amine-reactive group for reaction with amine groups on a protein surface, and an alkyl halide group for reaction with a monomer to initiate polymerization. Again, any suitable amine-reactive group, any suitable alkyl halide, and any suitable positively charged group can be used, including those listed herein.

In some cases, the methods provided herein can further include using ATRP to generate a protein-polymer conjugate from a protein-initiator conjugate prepared as described herein. For example, a protein-initiator conjugate can be contacted with a population of monomers in the presence of a transition metal catalyst or metal-free organic complex that can participate in a redox reaction.

ATRP can be carried out using standard methods. For example, a protein-initiator/protein-blocker complex can be contacted with a population of monomers and a transition metal catalyst that includes a metal ligand complex. Any appropriate metal ligand complex can be used. The transition metal in the metal ligand complex can be, for example, copper, iron, cobalt, zinc, ruthenium, palladium, or silver. The ligand in the metal ligand complex can be, without limitation, an amine-based ligand (e.g., 2,2'-bipyridine (bpy), 4,4'-di(5-nonyl)-2,2'-bipyridine (dNbpy), N,N,N',N'-tetramethylethylenediamine (TMEDA), N-propyl(2-pyridyl)methanimine (NPrPMI), 2,2':6',2"-terpyridine (tpy), 4,4',4"-tris(5-nonyl)-2,2':6',2"-terpyridine (tNtpy), N,N,N', N",N"-pentamethyldiethylenetriamine (PMDETA), N,N-bis (2-pyridylmethyl)octylamine (BPMOA), 1,1,4,7,10,10-hexamethyltriethylenetetramine (HMTETA), tris[2-(dimethylamino)ethyl]amine (Me6TREN), tris[(2-pyridyl) methyl]amine (TPMA), 1,4,8,11-tetraaza-1,4,8,11-tetramethylcyclotetradecane (Me4CYCLAM), or N,N,N', N'-tetrakis(2-pyridylmethyl)ethylenediamine (TPEN). The invention will be further described in the following examples, which do not limit the scope of the invention described in the claims.

EXAMPLES

Example 1—Materials and Methods

Materials: α-chymotrypsin (CT) from bovine pancreas (type II), acetylcholinesterase (AChE) from *Electrophorus electricus* (electric eel, type Vl-S), Uricase from *Candida* sp., and Lysozyme 548 from chicken egg white were purchased from Sigma Aldrich (St. Louis, MO). CT and Lysozyme were used as received. AChE and Uricase were dialyzed in 25 mM sodium phosphate (pH 7.0) using a 25 kDa molecular weight cutoff dialysis tube in a refrigerator for 24 hours and then lyophilized. Copper (II) chloride, sodium ascorbate, 1,1,4,7,10,10-hexamethyltriethylenetetramine (HMTETA), 2-bromo-2-methylpropionyl bromide, 3-(dimethylamino)-1-propylamine, N,N'-diisopropylcarbodimine, fluorescamine, acetylthiocholine iodide, 5,5'-dithiobis(2-nitrobenzoic acid) (DTNB) were purchased from Sigma Aldrich. 4-bromobutyric acid and N-hydroxysuccinimide were purchased from TCI USA (Portland, OR). Micro BCA assay kit was purchased from Thermo Fisher Scientific.

Instrumentation and Sample Analysis Preparations: $^1$H and $^{13}$C NMR were recorded on a spectrometer (500 MHz, 125 MHz, Bruker Avance™ 500) with deuterium oxide ($D_2O$) and DMSO-$d_6$. Routine FT-IR spectra were obtained with a Nicolet Avatar 560 FT-IR spectrometer (Thermo). UV-VIS spectra were obtained and used for enzyme activity determination using an UV-VIS spectrometer (Lambda 45, PerkinElmer) with a temperature-controlled cell holder. Melting points (mp) were measured with a Laboratory Devices Mel-Temp. Number and weight average molecular weights (Mn and Mw) and the polydispersity index ($M_w/M_n$) were estimated by gel permeation chromatography (GPC) on a Water 2695 Series with a data processor, equipped with three columns (Waters Ultrahydrogel Linier, 500 and 250), using Dulbecco's Phosphate Buffered Saline with 0.02 wt % sodium azide for pCBMA and 80 vol % of 100 mM sodium phosphate (pH 9.0) and 20 vol % of acetonitrile for pSMA as an eluent at flow rate 1.0 mL/min, with detection by a refractive index (RI) detector. Pullulan standards (PSS—Polymer Standards Service—USA Inc, Amherst, MA) were used for calibration. Matrix-Assisted Laser Desorption Ionization Time-of-Flight Spectrometry (MALDI-TOF MS) was performed with a Perseptive Biosystems Voyager Elite MALDI-TOF spectrometer. Dynamic Light Scattering (DLS) data were collected on a Malvern Zetasizer nano-ZS. The concentration of the sample solution was kept at 0.2-1.0 mg/mL. The hydrodynamic diameter of samples was measured three times (15 run to each measurement) in various buffers.

Positive Initiator (1) Synthesis and Characterization 4-bromobutyloyl-N-oxysuccinimide ester (2): N,N'-diisopropylcarbodimine (8.5 mL, 55 mmol) was slowly added to the solution of 4-bromobutyric acid (8.4 g, 50 mmol) and N-hydroxysuccinimide (4.3 g, 55 mmol) in dichloromethane (100 mL) at 0° C., and the mixture was stirred at room temperature overnight. Precipitated urea was filtered out and the filtrate was evaporated to remove solvent. 4-bromobutyloyl-N-oxysuccinimide ester was isolated by recrystallization in 2-propanol; yield 589 10.2 g (77%), mp 49-52° C. $^1$H NMR (500 MHz, DMSO-$d_6$) δ 2.16 (m, 2H, C=OCH$_2$CH$_2$CH$_2$Br), 2.81 (s, 4H, succinimide), 2.83 (t, 2H, J=7.0 Hz, C=OCH$_2$CH$_2$CH$_2$Br), 3.60 (t, 2H, J=7.0 Hz, C=OCH$_2$CH$_2$CH$_2$Br) ppm; $^{13}$C NMR (125 MHz, DMSO-d$_6$) δ 25.9, 27.9, 29.5, 33.3, 168.7, 170.6 ppm; IR (KBr pellete) 3017, 2948, 2914, 2852, 1812, 1786, 1731, 1382, 1360, 1311, 1202 and 1150 cm$^{-1}$.

N-(3-N',N'-dimethylaminopropyl)-2-bromo-2-methylpropanamide (3): 2-bromo-2-methylpropionyl bromide (3.4 mL, 27 mmol) was slowly added into the solution of 3-(dimethylamino)-1-propylamine (3.1 mL, 24.6 mmol) in deionized water (50 mL) at 0° C., and the the mixture was stirred at room temperature for 1 hour. After the mixture adjusted to pH 10 with 5 N NaOH aq. at 0° C., the product was extracted with ethyl acetate (50 mL×3). The organic phase was washed with 20 wt % of potassium carbonate aq. (50 mL×3) and saturated NaCl aq. (50 mL×2). The organic phase was dried with Na$_2$CO$_3$ and evaporated to remove solvent. N-(3-N',N'-dimethylaminopropyl)-2-bromo-2-methylpropanamide was obtained in vacuum. oil compound; yield 5.9 g (95%), $^1$H NMR (500 MHz, DMSO-d$_6$) δ 1.56 (m, 2H, (CH$_3$)$_2$NCH$_2$CH$_2$CH$_2$NHC=O), 1.84 (s, 6H, C=OC(CH$_3$)$_2$Br), 2.11 (s, 6H, (CH$_3$)$_2$NCH$_2$CH$_2$), 2.22 (t, 2H, J=7.0 Hz, (CH$_3$)$_2$NCH$_2$CH$_2$), 3.12 (td, 2H, J=5.5 Hz and J=7.0 Hz, CH$_2$CH$_2$NHC=O), 8.20 (broad t, 1H, J=5.5 Hz, amide) ppm; $^{13}$C NMR (125 MHz, DMSO-d$_6$) δ 26.7, 31.6, 38.7, 45.5, 57.4, 61.5, 170.9 ppm; IR (NaCl plate) 3349, 2975, 2946, 2864, 2822, 2800, 1661, 1537, 1465, 1370, 1294, 1263, 1195, 1161 and 1113 cm$^{-1}$.

Positively charged ATRP initiator (1): N-(3-N',N'-dimethylaminopropyl)-2-bromo-2-methylpropanamide (1.9 g, 7.5 mmol) and 4-bromobutyloyl-N-oxysuccinimide ester (2.0 g, 1.5 mmol) were added in dried acetonitrile (50 mL) and bubbled with nitrogen gas for 10 minutes. The mixture was sealed and stirred at 40° C. overnight. Positively charged ATRP initiator (1) was precipitated in mixture of ethyl acetate and diethyl ether (1:1 volume ratio), and the oil compound was isolated in vacuo; yield 3.6 g (93%), $^1$H NMR (500 MHz, D$_2$O) δ 1.88 (s, 6H, C=OC(CH$_3$)$_2$Br), 1.91-2.24 (m, 4H, C=OCH$_2$CH$_2$CH$_2$N$^+$CH$_2$CH$_2$CH$_2$NHC=O), 2.83-2.93 (m, 9H, succinimide and C=OCH$_2$CH$_2$CH$_2$N$^+$(CH$_3$)), 3.04-3.14 (m, 5H, C=OCH$_2$CH$_2$CH$_2$N$^+$(CH$_3$)), 3.28-3.41 (m, 4H, N$^+$CH$_2$CH$_2$CH$_2$NHC=O) ppm; $^{13}$C NMR (125 MHz, D$_2$O) 822.1, 24.0, 25.6, 30.6, 36.6, 42.9, 51.1, 55.4, 61.6, 62.1, 169.1, 173.2, 174.9 ppm; IR (NaCl plate) 3418, 2969, 2708, 1813, 1780, 1734, 1653, 1536, 1472, 1371, 1298, 1210, 1113 and 1074 cm$^{-1}$.

Protein-Initiator Synthesis and Characterization

CT: 200 μL of NHS-functionalized ATRP initiator solution in DMSO (168 μmol, 56 mg for neutral and 87 mg for positive initiator, respectively) was added to CT solution (60 mg in 30 mL of 100 mM phosphate (pH 8.0)) and stirred at 4° C. for 2 hours. CT-initiator conjugates were dialyzed in deionized water using a 15 kDa molecular cutoff dialysis tube in a refrigerator for 24 hours and then lyophilized.

Lysozyme: 200 μL of NHS-functionalized ATRP initiator solution in DMSO (172 58 mg for neutral and 89 mg for positive initiator, respectively) was added to lysozyme solution (70 mg in 30 mL of 100 mM phosphate (pH 8.0)) and stirred at room temperature for 2 hours. Lysozyme-initiator conjugates were dialyzed in deionized water using an 8 kDa molecular cutoff dialysis 632 tube in a refrigerator for 24 hours and then lyophilized.

Uricase: 200 μL of NHS-functionalized ATRP initiator solution in DMSO (100 μmol, 34 mg for neutral and 52 mg for positive initiator, respectively) was added to Uricase solution (20 mg of 638 Uricase in 20 mL of 100 mM phosphate (pH 7.0)) and stirred at room temperature for 2 hours. Uricase-initiator conjugates were dialyzed in 25 mM sodium phosphate (pH 7.0) using a 25 kDa molecular cutoff dialysis tube in a refrigerator for 24 hours and then lyophilized. The concentration of Uricase initiator conjugates was determined using a Micro BCA Assay Kit (ThermoFisher Scientific).

AChE: 100 μL of NHS-functionalized ATRP initiator solution in DMSO (12.7 μmol, 4.3 mg for neutral and 5.5 mg for positive initiator, respectively) was added to AChE solution (7 mg of AChE in 10 mL of 100 mM phosphate (pH 8.0)) and stirred at room temperature for 2 hours. AChE-initiator conjugates were dialyzed in 25 mM sodium phosphate (pH 7.0) using a 25 kDa molecular cutoff dialysis tube in a refrigerator for 24 hours and then lyophilized. The concentration of AChE initiator conjugates was determined using a Micro BCA Assay Kit.

BCA protein assay: The concentration of protein in the solution was determined using a Micro BCA protein Assay Kit (ThermoFisher Scientific). The sample solution (25 μL) and Micro BCA working reagent (75 μL) were incubated at 60° C. for 1 hour. After 900 μL of deionized water was added, the absorbance at 562 nm was recorded by a UV-VIS spectrometer (Lambda 45, Perkin Elmer). The standard curve was obtained from native protein with different concentration.

Fluorescamine assay: A fluorescamine assay was used to determine the number of initiators bound on the protein surface. 40 μL of sample, 100 mM sodium phosphate (40 μL, pH 8), and fluorescamine solution in DMSO (20 μL, 3 mg/mL) were added to wells of a 96-well plate and incubated at room temperature for 15 minutes. Fluorescence intensities were measured at the excitation of 390 nm and emission of 470 nm with 10-nm bandwidths by a Safire Spike plate reader. Concentrations were determined using a standard curve obtained from the native protein.

Trypsin digestion of protein-initiators: Trypsin digestion was performed on protein-initiators to generate peptide fragments to determine modification sites. Peptide fragments were analyzed using matrix-assisted laser desorption/ionization time-of-flight (MALDI-ToF) mass spectrometry. Native CT, CT-neutral initiator, and CT-positive initiator were digested according to the protocol described in the In-Solution Tryptic Digestion and Guanidination Kit. 20 μg of protein or protein-initiator complexes (10 of a 2 mg/mL protein solution in deionized water) were added to 15 μL of 50 mM ammonium bicarbonate with 1.5 μL of 100 mM dithiothreitol (DTT) in an Eppendorf tube. The reaction was incubated for 5 minutes at 95° C. Three (3) μL of 100 mM iodoacetamide aqueous solution was then added and samples were incubated in the dark for 20 minutes at room temperature for thiol alkylation. Next, 1 μL of 100 ng trypsin was added to the tube and the reaction was incubated at 37° C. for 3 hours. An additional 1 of 100 ng trypsin was subsequently added. The trypsin digestion was terminated after a total reaction time of 12 hours by the addition of trifluoroacetic acid (TFA). Digested samples were purified using ZipTipC$_{18}$ microtips and eluted with 2 μL of matrix solution (20 mg/mL sinapinic acid in 50% acetonitrile with 0.1% TFA) directly onto a MALDI-ToF plate. The molecular weight of the expected peptide fragments before and after digestion was predicted using PeptideCutter on UniProt P00766 (ExPASy Bioinformatics Portal, Swiss Institute of Bioinformatics). CT-initiator digests were compared to native CT digests. Modification at a particular amino group was determined by either the loss of a peak of the CT-initiator in comparison to native CT or by the appearance of a new peak that equaled the mass (or adducts) of the peptide fragment plus the mass of the initiator (neutral initiator: 220 Da, positive initiator: 320 Da).

MALDI-ToF analysis: Protein solutions (1.0 mg/mL) were mixed with an equal volume of matrix (Sinapinic acid (20 mg/mL) in 50% acetonitrile with 0.4% trifluoroacetic acid), and 2 µL of the resulting mixture was loaded onto a silver sterling plate target. Apomyoglobin, cytochrome C, and aldolase were used as calibration standards. To determine the extent of initiator modification on protein-initiators, the m/z of the native protein was subtracted from the m/z of the protein-initiator. The difference in m/z was then divided by the mass of the initiator (neutral initiator: 220 Da, positive initiator: 320 Da) to obtain the number of initiators per protein. When analyzing trypsin digests of protein-initiators, Bradykinin fragment, angiotensin II (human) and insulin oxidized B chain (bovine) were used as calibration standards. MALDI-ToF data was collected on a PerSeptive Voyager STR MS with nitrogen laser (337 nm) and 20 kV accelerating voltage with a grid voltage of 90%. 300 laser shots covering the complete spot were accumulated for each spectrum.

Isoelectric Focusing (IEF) gel: Criterion IEF precast gels (pH 3-10, 12+2 well, polyacrylamide gel, 13.3×8.7 cm) from Bio-Rad were used to determine the isoelectric point of proteins and protein-initiators. Protein solutions (concentration depending on the sample) were mixed with 50% glycerol using a 1 to 10 ratio of protein sample to 50% glycerol. Thirty (30) µL were loaded into each well. The IEF standards were prepared and loaded according to the Bio-Rad instruction manual. The gel was run in a stepwise manner as follows: 100 V for 60 minutes, 250 V for 60 minutes, 500 V for 30 minutes. Gels were silver stained using the Pierce Silver Stain Kit following their instructions.

CT-pCBMA and pSMA conjugate synthesis: A solution of monomer (230 mg for CBMA and 246 mg for SMA, 1.0 mmol respectively) and CT-initiator (23 mg for neutral and 25 mg for positive initiator, 10 µmol of initiator) in 100 mM sodium phosphate (20 mL, pH 7) was sealed and bubbled with nitrogen gas in an ice bath for 30 minutes. Two (2) mL of deoxygenated catalyst solution (Cao et al., Nano Today 2012, 7(5):404-413) was the added to the polymerization reactor under bubbling nitrogen. The mixture was sealed and stirred in a refrigerator for 1 hour. The conjugate was isolated by dialysis with a 25 kDa molecular weight cutoff dialysis tube in deionized water in a refrigerator for 24 hours and then lyophilized. Conjugate CT content was determined by BCA assay as described elsewhere (Lee et al. 2005, supra). Other protein-polymer conjugates were prepared by the same procedure as CT-polymers.

Acid hydrolysis and characterization of cleaved polymer: The grafted polymer was cleaved by acidic hydrolysis from the conjugate. CT-polymer conjugate (20 mg) and 6 N HCl aq. (5 mL) were placed in a hydrolysis tube. After three freeze-pump-thaw cycles, the hydrolysis was performed at 110° C. for 24 hours in vacuum. The cleaved polymer was isolated by dialysis using a 1 kDa molecular weight cut off dialysis tube in deionized water and then lyophilized. The molecular weight of the cleaved polymer was measured by GPC.

Dynamic light scattering: Dynamic light scattering data was collected on a Malvern Zetasizer nano-ZS located in the Department of Chemistry, Carnegie Mellon University, Pittsburgh, PA The hydrodynamic diameters (number distribution) of samples were measured three times (5 runs for each measurement) at room temperature.

Prediction of log D ChemAxon was used to draw the structure of and calculate the hydrophobicity (log D) of lysine side chains and lysine-initiators.

Activity Assays

CT: N-succinyl-Ala-Ala-Pro-Phe-p-nitroanilide (Suc-AAPF-pNA; SEQ ID NO:1) was used as a substrate for CT. Substrate (0-20 mg/mL in DMSO, 30 µL) was added to a 1.5 mL cuvette with sodium phosphate buffer (pH 8, 100 mM). Native CT, CT-initiators, and CT-polymers (0.1 mg/mL protein, 4 µM, 10 µL) was added to the cuvette with substrate and buffer. The initial substrate hydrolysis rate was measured in triplicate by recording the increase in absorbance at 412 nm over the first 60 seconds after mixing using a Lambda 2 Perkin Elmer ultraviolet-visible spectrometer equipped with a temperature-controlled cell holder at 37° C. Michaelis-Menten parameters were determined using nonlinear curve fitting of initial hydrolysis rate versus substrate concentration in GraphPad.

Lysozyme: Activity of Native, Lysozyme-initiator and polymer conjugates was determined by turbidimetric assay. Lyophilized *Micrococcus lysodeikticus* (Sigma Aldrich) was used to monitor enzymatic catalysis of cell wall lysis. Absorption at 450 nm of suspended *M. lysodeikticus* (990 µL, 0.2 mg/mL) in 50 mM sodium phosphate (pH 6.0) was measured by UV-VIS spectrometer. 10 µL of native and Lysozyme-initiator solution (1.4 µM in 50 mM sodium phosphate (pH 6.0)) was added and the change of absorbance at 450 nm at room temperature was monitored.

Uricase: Uric acid (0-400 µL of 300 µM in in 50 mM sodium tetraborate (pH 8.5)) was mixed with 50 mM sodium phosphate (990-580 µL, pH 8.5). Native, initiator and polymer conjugate solution (10 µL, 20 µM of Uricase) was added to the substrate solution. The initial rate was monitored by recording the decreasing in absorbance as 290 nm using an UV-VIS absorbance spectrometer with a temperature controlled cell folder at 37° C. Michaelis-Menten parameters were determined by nonlinear curve fitting of initial rate versus substrate concentration plots using Prism 7 software (GraphPad).

AChE: Acetylthiocholine iodide (0-100 µL of 10 mM in 100 mM sodium phosphate buffer (pH 7.4)) and 10 µL of DTNB solution (50 mM in DMSO) was mixed with 100 mM sodium phosphate (980-880 µL, pH 7.4). Native, initiator and polymer conjugates solution (10 µL, 4.2 µM of AChE) was added to the substrate solution. The initial rate was monitored by recording the increasing in absorbance as 412 nm using an UV-VIS absorbance spectrometer with a temperature controlled cell folder at 37° C. Michaelis-Menten parameters were determined by nonlinear curve fitting of initial rate versus substrate concentration plots using Prism 7 software (GraphPad).

Residual Activity Assays

CT: Native CT, CT-initiators, and CT-polymers (1 mg/mL, 40 µM protein) were dissolved in sodium phosphate buffer (pH 8, 100 mM). In triplicate, samples were then diluted to 4 µM for incubation. For thermostability, samples were incubated at 50° C. and pH 8 in a circulating water bath. For acid stability, samples were incubated at pH 1 (167 mM HCl) and 37° C. At specified time points, aliquots of 10 µL were removed over 60 minutes and residual activity was measured using Suc-AAPF-pNA as a substrate (6 mg/mL, 30 µL, 288 µM in DMSO) in sodium phosphate buffer (pH 8, 100 mM, 37° C., 960 µL). Initial hydrolysis rate was measured as the increase in absorbance at 412 nm over 40 seconds and data was normalized to its optimal activity (pH 8, 37° C.) at time 0.

Lysozyme: Native lysozyme, initiator and polymer conjugates (14 µM of Lysozyme) in 50 mM sodium phosphate (pH 6.0) were incubated at 80° C. At given time, aliquots (10 µL) were removed and activity was measured in 990 µL of suspended *M lysodeikticus* (0.2 mg/mL) in 50 mM sodium phosphate (pH 6.0) at room temperature. Rates were monitored by recording the decreasing in absorbance at 450 nm using UV-VIS spectrometer. The residual activity was calculated as a ratio of initial rates of the reaction at the given incubation time over initial activity at time zero.

Uricase: Native uricase, initiator and polymer conjugates (20 µM of Uricase) in 50 mM sodium borate (pH 8.5) were incubated at 75° C. At given time, aliquots (10 µL) were removed and activity was measured in 990 µL of 100 µM of uric acid in 50 mM sodium borate (pH 8.5) at 37° C. Rates were monitored by recording the decreasing in absorbance at 290 nm using UV-VIS spectrometer. The residual activity was calculated as a ratio of initial rates of the reaction at the given incubation time over initial activity at time zero.

AChE: Native, initiator, and polymer conjugates (1.4 µM of AChE) in 100 mM sodium phosphate (pH 7.0) were incubated at 50° C. At given time, aliquots (10 µL) were removed and activity was measured in the mixture of 930 µL of 100 mM sodium phosphate (pH 7.4), 50 µL of acetylthiocholine iodide (10 mM in 100 mM sodium phosphate (pH 7.4) and 10 µL of DTNB solution (50 mM in DMSO) at 37° C. Rates were monitored by recording the increasing in absorbance at 412 nm using UV-VIS spectrometer. The residual activity was calculated as a ratio of initial rates of the reaction at the given incubation time over initial activity at time zero.

Tryptophan Fluorescence: Fluorescence measurements were collected using a BioTek Synergy H1 Plate Reader. Native CT, CT-initiators, and CT-polymers (1 mg/mL, 40 µM protein) were dissolved in sodium phosphate buffer (pH 8, 100 mM). Samples were diluted to 0.1 mg/mL (4 µM protein) in a black round bottom 96 well plate in triplicate. For thermostability, samples were incubated at 45° C. and pH 8. For acid stability, samples were incubated at pH 1 (167 mM HCl) and 37° C. Fluorescence intensity was measured every 2 minutes over 60 minutes (excitation at 270 nm, emissions at 330 nm and 350 nm). The ratio of emission fluorescence intensities (350 nm/330 nm) was plotted over time with time 0 as the fluorescence intensity of the sample at pH 8 and 37° C.

Molecular Dynamics Simulation: A CT-positive initiator model was built with the Maestro Schrodinger build toolkit using the crystal structure of CT as the initial structure (PDB: 4CHA). Positive initiators were attached to the N-terminus and all 14 lysine residues to create a fully modified CT-positive initiator complex. The molecule was subjected to a 1 ns simulated annealing using Desmond. Simulated annealing was performed in 4 stages: linear increasing temperature from 300-400 K over 0-100 ps, constant temperature at 400 K from 100-400 ps, linear decreasing temperature from 400-300 K over 400-700 ps, and constant temperature at 300 K from 700-1000 ps. The simulation system was prepared in Desmond system builder and consisted of OPLS 2005 force field, SPC water model, orthorhombic minimized box, and NaCl ions to neutralize the box followed by the addition of 100 mM NaCl. NVT ensemble and Berendsen thermostat were used to control temperature with a 1 ps relaxation time. The van der Waals interaction had a cutoff of 9 Å and particle mesh Ewald was used for Coulomb interactions with a 9 Å switching distance. The molecule was simulated using Desmond over 1 ns with a 1.2 ps recording energy interval and 5 ps trajectory recording. A molecular dynamics simulation production run was performed on the final structure from simulated annealing. The simulation was performed over 20 ns at 300 K with a NPT ensemble (trajectories were recorded every 1.2 ps and energy was recorded every 4.8 ps). The trajectory was then loaded into Visual Molecular Dynamics (VIVID) software for further analysis. The VIVID salt bridge plug-in was used to monitor salt bridge formation and location over the 20 ns trajectory.

Example 2—Protein-Initiators and Protein-Polymer Conjugates

A positively charged ATRP-initiator (FIGS. 1 and 2) was synthesized. N-(3-N',N'-dimethylaminopropyl)-2-bromo-2-methylpropanamide and 4-bromobutyloyl-N-oxysuccinimide ester were synthesized and then reacted with each other to form the final positively charged ATRP-initiator. The overall synthesis had a 68% yield. The positive charge was in the form of a quaternary ammonium group located about halfway between the protein-reactive NHS group and the terminal alkyl halide. The quaternary ammonium group as the source of the positive charge was selected because it would remain positively charged at any pH, as it does not have a $pK_a$.

The initiator was used to grow pCBMA or pSMA from the chymotrypsin surface (FIG. 2). pCBMA, a zwitterionic polymer, increased activity and stability, while pSMA, a negatively charged polymer, was devastating to normal function (Cummings 2017, supra). These conjugates represented the best and worst case scenarios when using a neutral ATRP-initiator.

Figure 3A:
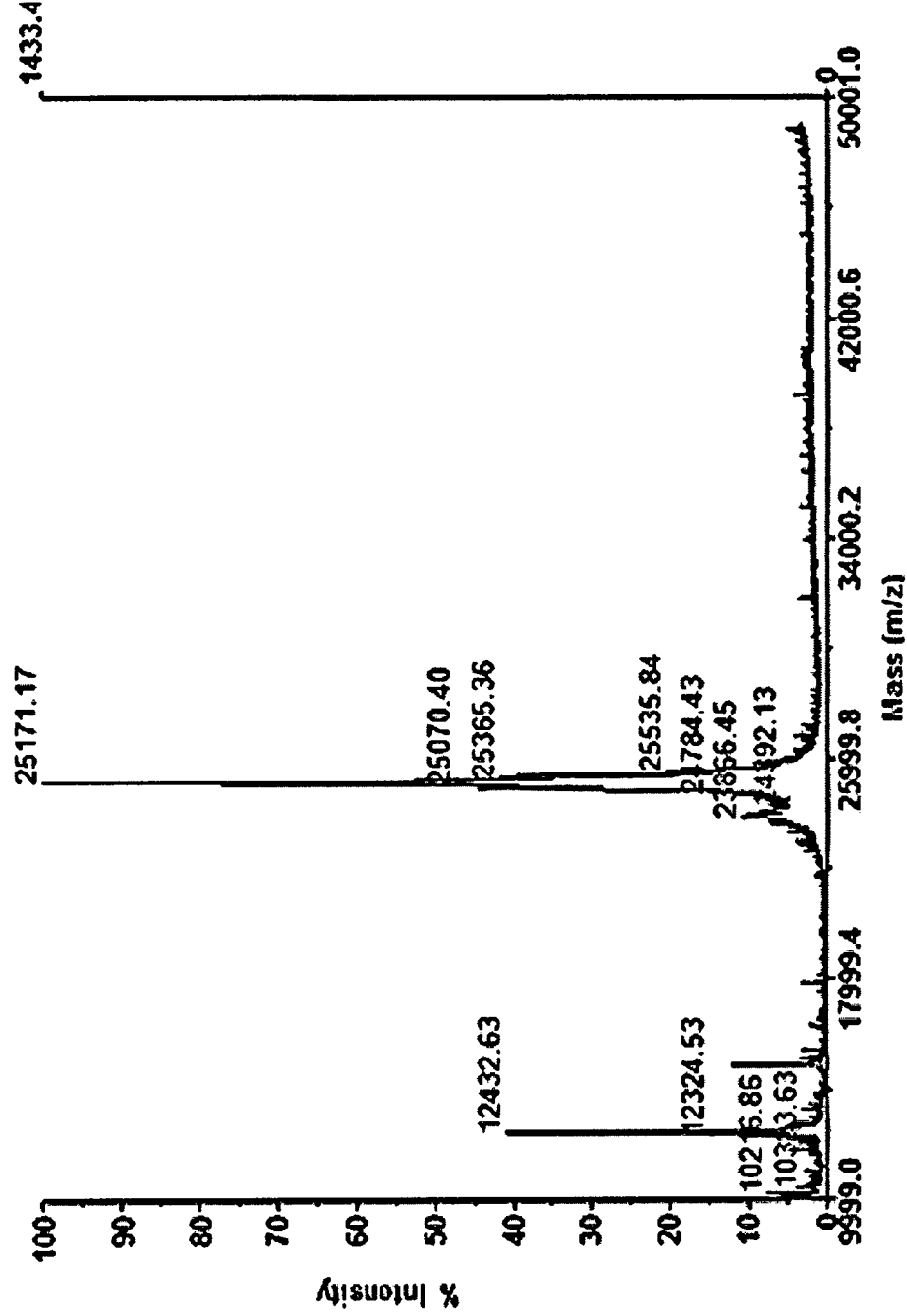
FIGS. 3A-3C are MALDI-ToF spectra of native CT (FIG. 3A), CT(+) (FIG. 3B), and CT(N) (FIG. 3C). The number of modifications was 75, determined by taking the difference in m/z of the CT-initiators and native CT and dividing by the initiator 76 molar mass without the —NHS group (positive initiator=320 Da, neutral initiator=220 Da). CT(+) had an average of 10.6 modifications and CT(N) had an average of 14.1 modifications.
Figure 3B:
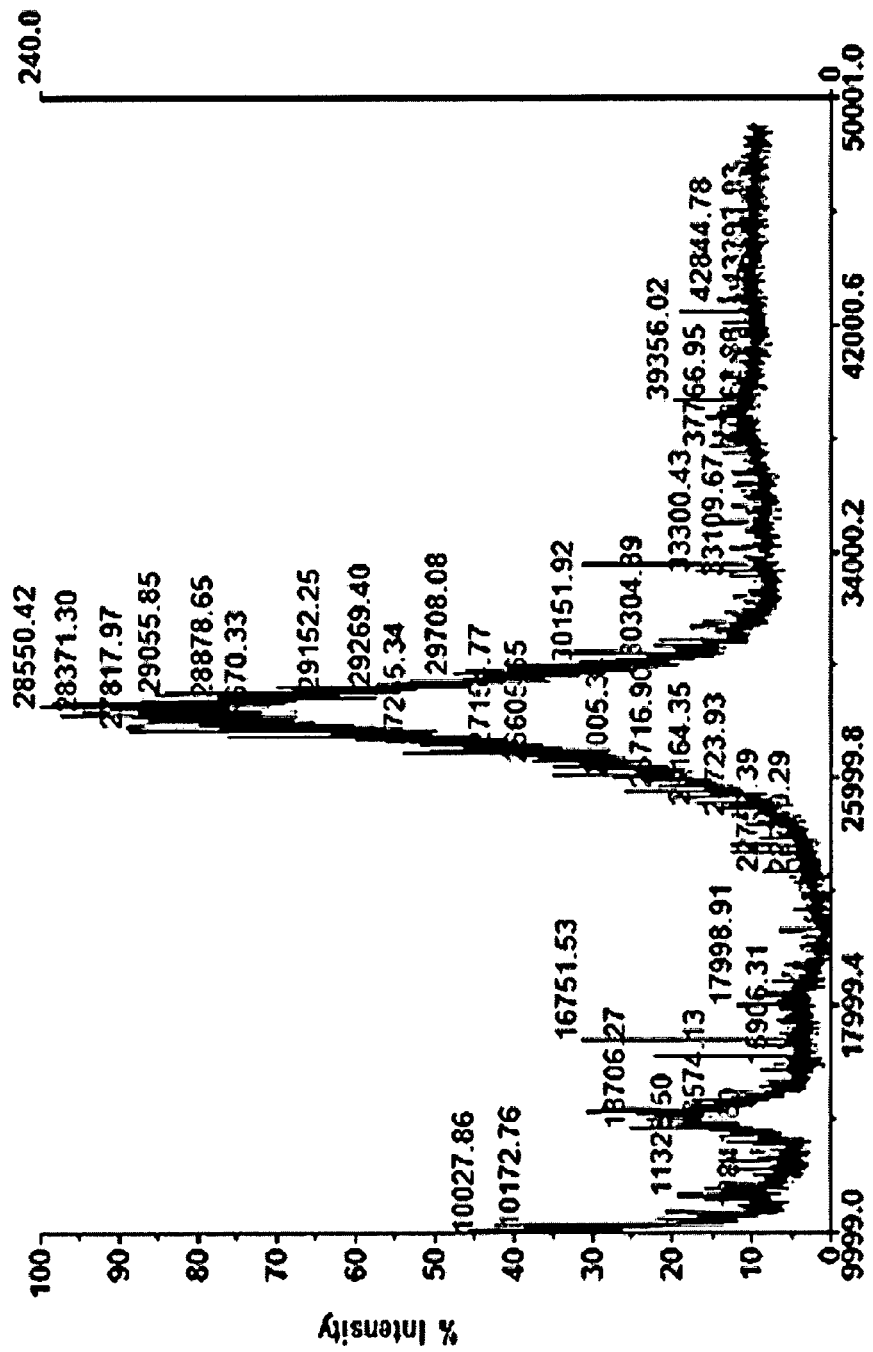
Figure 3C:
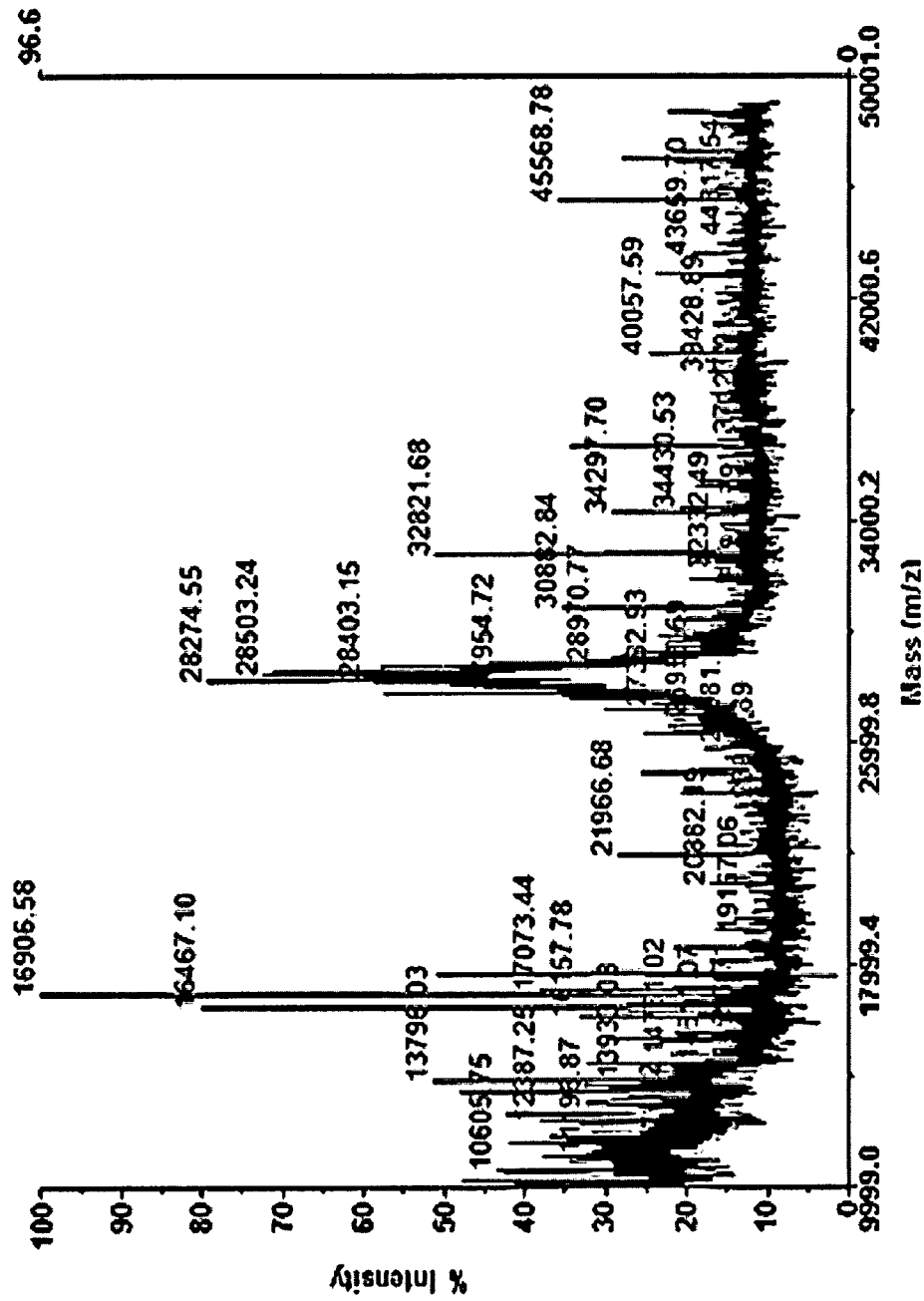
Figure 4:
FIG. 4 is an image of an isoelectric focusing gel used to determine the change in pI of chymotrypsin upon modification with neutral or positively charged ATRP-initiators. The gel had a pH gradient from 3-10. Lanes 1 and 8: ladders, Lane 2: CT-positive initiator (low concentration, 0.6 µg/well), Lane 3: CT-positive initiator (high concentration, 1.2 µg/well), Lane 4: CT-neutral initiator (low concentration, 0.6 µg/well), Lane 5: CT-neutral initiator (high concentration, 1.2 µg/well), Lane 6: CT (low concentration, 1.2 µg/well), Lane 7: CT (high concentration, 2.4 µg/well). The pI's of CT, CT-neutral initiator, and CT-positive initiator were ~9.6, <3-6, and 5-7.5, respectively. The multiple bands in the CT-initiator lanes were due to different populations of macroinitiators that varied in the degree of modification.

The CT-initiator complexes were analyzed with MALDI-ToF mass spectroscopy to determine the average number of amino groups that had been modified (FIGS. 3A-3C). CT has 15 total amino groups (one at the N-terminus and 14 on lysine residues). The average numbers of initiators attached to CT were 14 for the neutral initiator and 11 for the positive initiator (TABLE 1). The slight decrease in total number of positive initiator modifications in comparison to the neutral initiator was likely due to its larger size and charge. The larger size could inhibit reactions with primary amines that have decreased solvent accessible surface areas, while the positive charge could hinder reactions with primary amines in positively charged regions of CT (Carmali et al., supra). In order to determine the sites of modification for each protein-initiator complex, trypsin digestion followed by analysis of peptide fragments using MALDI-ToF was performed (TABLES S2 and S3→2 and 3). In determining how the different CT-initiators impacted the isoelectric point (pI) of CT (the pH at which CT has no net electrical charge), an isoelectric focusing (IEF) gel that had a pH 3-10 gradient was used (FIG. 4). Native CT had a pI of about 9.6. The pI of CT-neutral initiator dropped to pI values ranging from ~3-6, with the majority at the limit of the gel around pH 3. There were three distinct bands: pI ~3, 5, and 6 which were most likely due to sub-populations of protein-initiators. While MALDI-ToF provided an average number of modifications in the sample, the IEF gel allowed visualization of the sub-populations with different degrees of modification. The decrease in pI for CT-neutral initiator (~5-7.5) was expected since the protein was losing positive charges and becoming more acidic. Theoretical pI values are calculated from an average of the individual residue $pK_a$ values, which are highly sensitive to their local electrostatic environment (Isom et al., *Proc. Natl. Acad. Sci. USA* 2011, 108(13):5260-5265). It also is known that charge-charge interactions are the dominant factor that shift p$K_a$ values of ionizable groups on the protein surface (Laurents et al., *J. Mol. Biol.* 2003, 325(5):1077-1092). Since the positively charged initiator did not have a p$K_a$, the pI of CT-positive initiator would be restored to native CT values. After verifying that pI values for CT-positive initiator were increased from CT-neutral initiator, protein-polymer conjugates were synthesized (TABLE 1). CT-pCBMA conjugates had slightly larger hydrodynamic diameters because pCBMA is super-hydrophilic, which would give CT-pCBMA a larger hydration layer than CT-pSMA conjugates.

To obtain the data presented in TABLE 1, two conjugates were synthesized for each macroinitiator: one with pCBMA and one with pSMA. Degree of initiator modification was determined using MALDI-ToF mass spectroscopy. Protein-polymer conjugates were characterized by various methods. A bicinchoninic acid (BCA) assay was used to determine protein content from which total conjugate molecular weight and degree of polymerization were estimated. Polymers were cleaved from the protein surface using acid hydrolysis to be analyzed separately by gel permeation chromatography (GPC). The polymer molecular weight, and thus degree of polymerization, as well as total conjugate molecular weight were estimated. Hydrodynamic diameters (Dh) were also measured using dynamic light scattering and are reported as number distributions. All conjugates had similar degrees of polymerization around 100. Conjugates also grew in hydrodynamic diameter in comparison to native CT.

TABLE 1

Characterization of grafted-from CT-polymer conjugates using ATRP.

| Sample | Number of initiators by MALDI | Conjugate MW (kDa) by BCA (estimated DP) | Cleaved polymer MW (kDa); PDI by GPC | Conjugate MW (kDa) by GPC (estimated DP) | $D_h$ (nm) Number Distribution |
|---|---|---|---|---|---|
| Native CT | — | — | — | — | 3.98 ± 0.48 |
| CT-neutral initiator | 14.1 | — | — | — | 4.07 ± 0.31 |
| CT-positive initiator | 10.6 | — | — | — | 4.18 ± 0.70 |
| CT-neutral initiator-pCBMA | 14.1 | 329 (94) | 18.1; 1.54 | 281 (79) | 17.5 ± 7.7 |
| CT-positive initiator-pCBMA | 10.6 | 268 (100) | 23.8; 1.57 | 278 (104) | 18.3 ± 3.4 |
| CT-neutral initiator-pSMA | 14.1 | 433 (109) | 19.9; 1.54 | 306 (75) | 12.9 ± 6.9 |
| CT-positive initiator-pSMA | 10.6 | 262 (84) | 21.7; 1.44 | 256 (82) | 14.3 ± 7.5 |

TABLE 2

Trypsin digestion fragments of CT-neutral initiator

| Peptide fragment (SEQ ID NO:) | Expected mass (m/z) | Observed mass (m/z) | Amino group modified |
|---|---|---|---|
| CGVPAIQPVLSGLSR (2) | 3463.24 | 3463.94 [2M + 3H2O + 2H] | N-terminus |
| IVNGEEAVPGSWPWQVSLQDK (3) | 2602.5 | 2604.96 [M + ACN + H] | K36 |
| TGFHFCGGSLINENWVVTAAHCGVT TSDVVVAGEFDQGSSSEK (4) | 4843.7 | 4843.36 [M + ACN + Na] | K79 |
| IQK | 672.4 | 672.88 [M + ACN + Na] | K82 |
| LK or IK | 962.0 | 963.6 [2M + H] | K84 or K177 |
| IAK | 615.3 | 616.2 [M + ACN + Na] | K87 |
| LSTAASFSQTVSAVCLPSASDDFAAG TTCVTTGWGLTR (5) | 1342.6 | 1343.86 [M + 2H + Na] | K145 |
| LQQASLPLLSNTNCKK (6) | 2219.0 | 2220.38 [M + H] | K169 + K170 |
| YWGTK (7) | 917.0 | 916.4 [M + ACN + H] | K175 |
| DAMICAGASGVSSCMGDSGGPLVCK (8) | 2791.6 | 2791.20 [M + 2ACN + H] | K202 |

TABLE 3

Trypsin digestion fragments of CT-positive initiator.

| Peptide fragment (SEQ ID NO:) | Expected mass (m/z) | Observed mass (m/z) | Amino group modified |
|---|---|---|---|
| CGVPAIQPVLSGLSR (2) | 1858.8 | 1858.72 [M + ACN + Na] | N-terminus |
| IVNGEEAVPGSWPWQVSLQDK (3) | 2682.6 | 2683.05 [M + Na] | K36 |
| TGFHFCGGSLINENWVVTAAHCGVT TSDVVVAGEFDQGSSSEK (4) | 1627.3 | 1628.46 [M + 3H] | K79 |
| VFK | 1489.0 | 1487.89 [2M + ACN + Na] | K90 |
| LQQASLPLLSNTNCKK (6) | 2417.1 | 2416.52 [M + H] | K169 + K170 |
| YWGTK (7) | 2011.4 | 2010.23 [2M + ACN + Na] | K175 |

ATRP was used to synthesize CT-pCBMA and CT-pSMA conjugates from the neutral and positive protein-initiator complexes. The molecular weight of the polymers was kept constant (targeted degree of polymerization of 100) in order to compare the activity and stability of each conjugate to that of the native enzyme (Murata et al., *Biomacromolecules* 2014, 15(7):2817-2823). After ATRP and purification of the conjugate via dialysis, protein-polymer conjugates were characterized with a bicinchoninic acid (BCA) assay to determine protein concentration from which conjugate molecular weight and degree of polymerization were estimated (Lele et al., supra). The polymers also were cleaved from the protein surface via acid hydrolysis, and the isolated polymers were analyzed by gel permeation chromatography for relative molecular weight and polydispersity (PDI), from which conjugate molecular weight and degree of polymerization were estimated. The two characterization techniques agreed well, showing that the conjugates had similar degrees of polymerization. Hydrodynamic diameters (Dh) were also measured using dynamic light scattering and conjugates grew in size from 3.98 nm for native CT to approximately 18 nm for CT-pCBMA conjugates and approximately 13 nm for CT-pSMA conjugates grown from either CT-neutral or CT-positive initiators (TABLE 1).

Example 2—Activity of Chymotrypsin-Initiators and Chymotrypsin-Polymer Conjugates Michaelis-Menten kinetics were measured at pH 8 and 37° C. using Succinyl-Ala-Ala-Pro-Phe-p-nitroanilide (Suc-AAPF-pNA; SEQ ID NO:1), a hydrophobic and negatively charged substrate for CT that binds to the hydrophobic $S_1$ binding pocket and is then cleaved by the catalytic triad (Ser 195, His 57, Asp 102). The turnover numbers ($k_{cat}$, $s^{-1}$), Michaelis constants ($K_M$, μM), and specificity constants ($k_{cat}/K_M$, $μM^{-1}s^{-1}$) were determined for the CT-neutral initiator, CT-positive initiator and the conjugates (TABLE 4). The CT-neutral initiator and CT-positive initiator had similar activities, but both had higher overall catalytic efficiencies than native CT due to a decrease in $K_M$ by half. The observed decrease in $K_M$ upon neutral initiator attachment could have been the result of the hydrophobicity of the initiator. The partition coefficient (log D) of a lysine side chain at pH 8.0 is −1.00. After covalent attachment of the neutral initiator, the log D value of the new product rose to 1.82. Considering that this reaction occurred on 14 out of the possible 15 amino groups, the surface of CT would undoubtedly have become more hydrophobic, which would have strengthened the van der Waals interactions between the hydrophobic substrate and hydrophobic $S_1$ binding pocket to increase the affinity for the substrate. After attachment of the positive initiator, however, the log D decreased to −1.98, but the positive charge would have promoted favorable electrostatic interactions with the negatively charged substrate to increase the binding affinity.

Attachment of polymers to proteins can cause dramatic activity reductions, which has been attributed to protein structural stiffening (Rodriguez-Martinez et al., *Biotechnol. Bioeng.* 2008, 101(6):1142-1149). The turnover numbers for the CT-neutral initiator-pCBMA and CT-positive initiator-pCBMA were similar to that of the native CT, and the $K_M$ remained decreased. It was possible that pCBMA's superhydrophilicity could pull water molecules away from the protein surface and into the polymer phase, which would strengthen the hydrophobic-hydrophobic driving force for substrate binding (Cao et al., supra). When using the positive initiator, CT-pCBMA had an increased $k_{cat}/K_M$ (0.30±0.01 to 0.42±0.02 $μM^{-1}s^{-1}$), with an increased $k_{cat}$ and a decreased $K_M$ (TABLE 4). The overall catalytic efficiency of CT-positive initiator-pCBMA was nearly double that of native CT.

Zwitterionic polymers are known to stabilize proteins, whereas negatively charged polymers, such as pSMA, can inactivate CT rapidly. Indeed, tryptophan fluorescence intensity at pH 8 after synthesis of the CT-neutral initiator-pSMA conjugate was synthesized increased, indicating that the conjugate was already partially unfolded even in its most optimal environment. The growth of pSMA from CT-neutral initiator caused CT to lose 97% of its activity. A positively charged initiator might protect enzymes from polymer-induced decreases in function. Excitingly, the CT-positive initiator-pSMA conjugate had restored activity compared to native CT in terms of both $k_{cat}$ and $K_M$ and a nearly 20-fold higher overall activity than CT-neutral initiator-pSMA.

TABLE 4

Michaelis-Menten kinetics at pH 8 and 37° C. of native CT, CT-neutral initiator, CT-positive initiator, and conjugates with pCBMA and pSMA grown from the differently charged protein-initiators. Activity pH dependence at pH 8 and 37° C.

| | $k_{cat}$ (s$^{-1}$) | $K_M$ (μM) | $k_{cat}/K_M$ (μM$^{-1}$s$^{-1}$) |
|---|---|---|---|
| CT | 26.6 ± 0.3 | 107 ± 5 | 0.25 ± 0.01 |
| CT-neutral initiator | 18.9 ± 0.4 | 53 ± 5 | 0.36 ± 0.03 |
| CT-positive initiator | 21.6 ± 0.6 | 60 ± 7 | 0.36 ± 0.03 |
| CT-neutral initiator-pCBMA | 25.6 ± 0.2 | 84 ± 3 | 0.30 ± 0.01 |
| CT-positive initiator-pCBMA | 30.5 ± 0.6 | 73 ± 6 | 0.42 ± 0.02 |
| CT-neutral initiator-pSMA | 3.0 ± 0.2 | 217 ± 35 | 0.01 ± 0.002 |
| CT-positive initiator-pSMA | 22.2 ± 0.2 | 109 ± 3 | 0.20 ± 0.004 |

Example 3—Resistance of CT-Initiators and CT-Polymer Conjugates to Heat- and Acid-Induced Inactivation Replacing neutral NHS amino-reactive protein modifiers with positively charged modifiers also can impact protein stability. Various strategies have been used to stabilize CT including by adding excipients (polyols and salts) (Lozano et al., *J. Biotechnol.* 1994, 35(1):9-18; Levitsky et al., *Eur. J. Biochem.* 1994, 219(1-2):231-236; and Baldwin, *Biophys. J.* 1996, 71(4):2056-2063), immobilization onto solid supports (Mozhaev et al., *Biotechnol. Bioeng.* 1990, 35(7):653-659), encapsulation into reverse micelles (Dorovska-Taran et al., *Eur. J Biochem.* 1993, 211(1-2):47-55), or by covalent attachment of polymer (Cummings et al. 2017, supra).

Figure 5A:
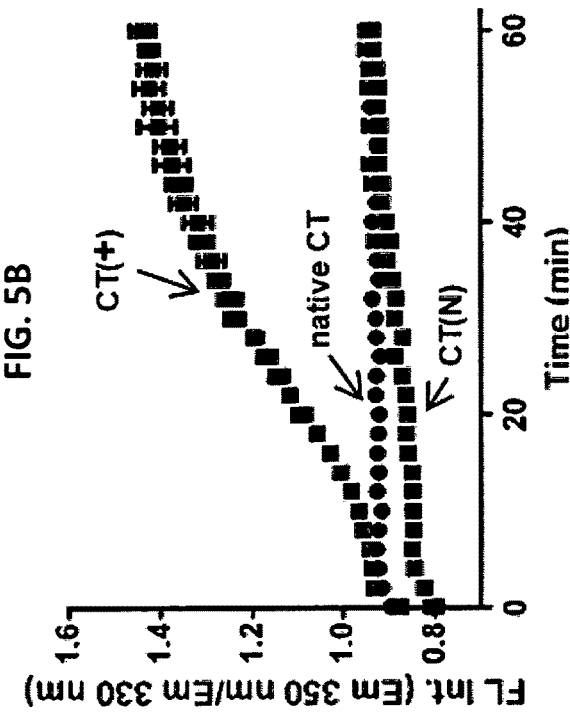
FIGS. 5A-5D are a series of graphs plotting the thermal and acid stabilities of native CT and CT-initiators. Stabilities were normalized to time 0, which represents the most active form of CT (pH 8 and 37° C.).
Figure 5B:
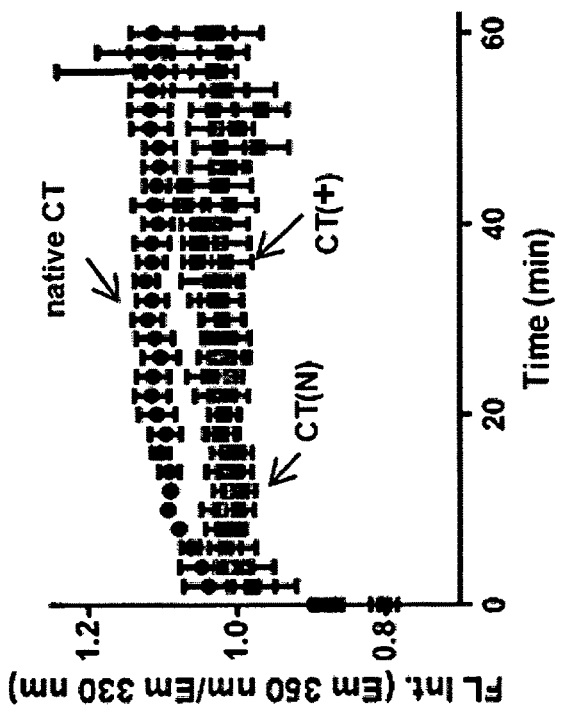
Figure 5C:
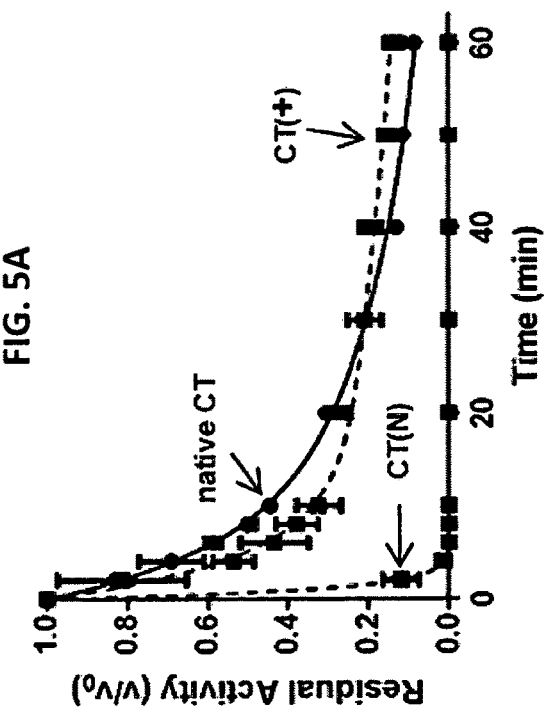
Figure 5D:
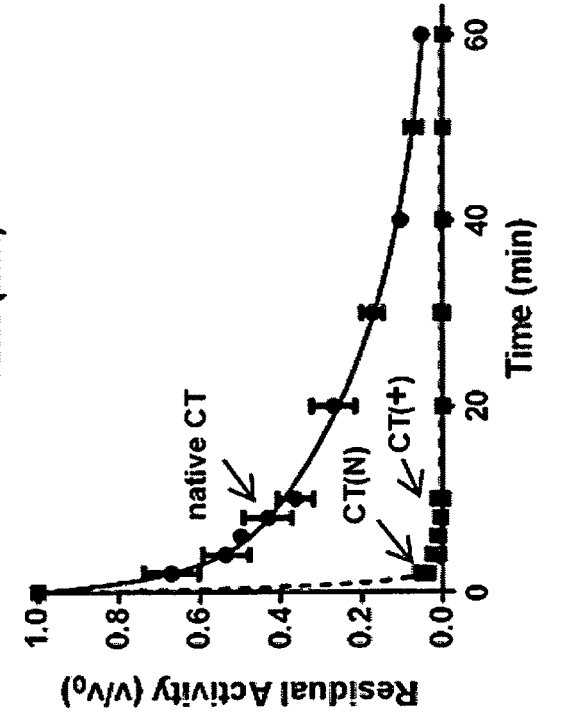

CT has a two-step deactivation mechanism where it undergoes complete deactivation via an intermediate transition state as follows (1),

$$F \xrightleftharpoons{k_1} I \xrightarrow{k_2} U \qquad (1)$$

where F, I, and U are the folded, intermediate, and unfolded conformational states, and $k_1$ and $k_2$ are first order deactivation rate constants (min$^{-1}$). CT resists inactivation by either not unfolding or refolding at a high rate (Lozano et al., *Eur. J. Biochem.* 1997, 248(1):80-85). The resistance of CT-initiator complexes and polymer conjugates to inactivation was determined using heat (50° C., pH 8) and acid (pH 1, 37° C.) (FIGS. 5A and 5C). At specified time points, aliquots were taken from the incubating samples and activities were measured at pH 8 and 37° C. Residual activities also were correlated with conformational changes by following changes in tryptophan fluorescence emissions over time during incubation at high temperature (45° C., pH 8) and in acid (pH 1, 37° C.) (FIGS. 5B and 5D) (Williams et al., *Strategies for Biophysical Characterization of Protein-Polymer Conjugates*, 1st ed.; Elsevier Inc., 2017; Vol. 590). At elevated temperature, the CT-neutral initiator was irreversibly inactivated within the first 5 minutes. A large increase in tryptophan fluorescence was observed, showing that the CT unfolded over time at elevated temperature. The stability profile of the CT-positive initiator was completely different than the CT-neutral initiator complex, however. The complex that maintained its electrostatic environment was similar to native CT. When the data were fitted to the two step inactivation model described by equation (1), the CT-positive initiator displayed a larger $k_1$ and a smaller $k_2$ than the native enzyme (TABLE 5). In acid, both CT-neutral and CT-positive initiators were irreversibly inactivated within the first 5 minutes, which correlated to rapid increases in tryptophan fluorescence intensities (FIGS. 5B and 5D and TABLE 6).

TABLE 5

Deactivation rates at pH 8 and 50° C.

| | One-phase decay | Two-phase decay | |
|---|---|---|---|
| | k(min$^{-1}$) | $k_1$(min$^{-1}$) | $k_2$(min$^{-1}$) |
| Native CT | — | 0.18 ± 0.05 | 0.03 ± 0.02 |
| CT-neutral initiator | 1.06 ± 0.03 | — | — |
| CT-positive initiator | — | 0.23 ± 0.04 | 0.01 ± 0.02 |
| CT-positive-neutral initiator mix | 0.55 ± 0.03 | 0.64 ± 0.01 | 0.10 ± 0.05 |
| CT-neutral initiator-pCBMA | 0.19 ± 0.04 | — | — |
| CT-positive initiator-pCBMA | 0.09 ± 0.03 | — | — |
| CT-neutral initiator-pSMA | — | 0.78 ± 0.21 | 0.12 ± 0.15 |
| CT-positive initiator-pSMA | — | 0.48 ± 0.06 | 0.02 ± 0.01 |

TABLE 6

Deactivation rates at pH I and 37° C.

| | One-phase decay | Two-phase decay | |
|---|---|---|---|
| | k(min$^{-1}$) | $k_1$(min$^{-1}$) | $k_2$(min$^{-1}$) |
| Native CT | — | 0.59 ± 0.14 | 0.04 ± 0.01 |
| CT-neutral initiator | 1.63 ± 0.09 | — | — |
| CT-positive initiator | 1.55 ± 0.06 | — | — |
| CT-neutral initiator-pCBMA | 1.51 ± 0.76 | — | — |
| CT-positive initiator-pCBMA | 0.88 ± 0.15 | — | — |
| CT-neutral initiator-pSMA | — | — | — |
| CT-positive initiator-pSMA | 1.69 ± 0.19 | — | — |

Figure 6A:
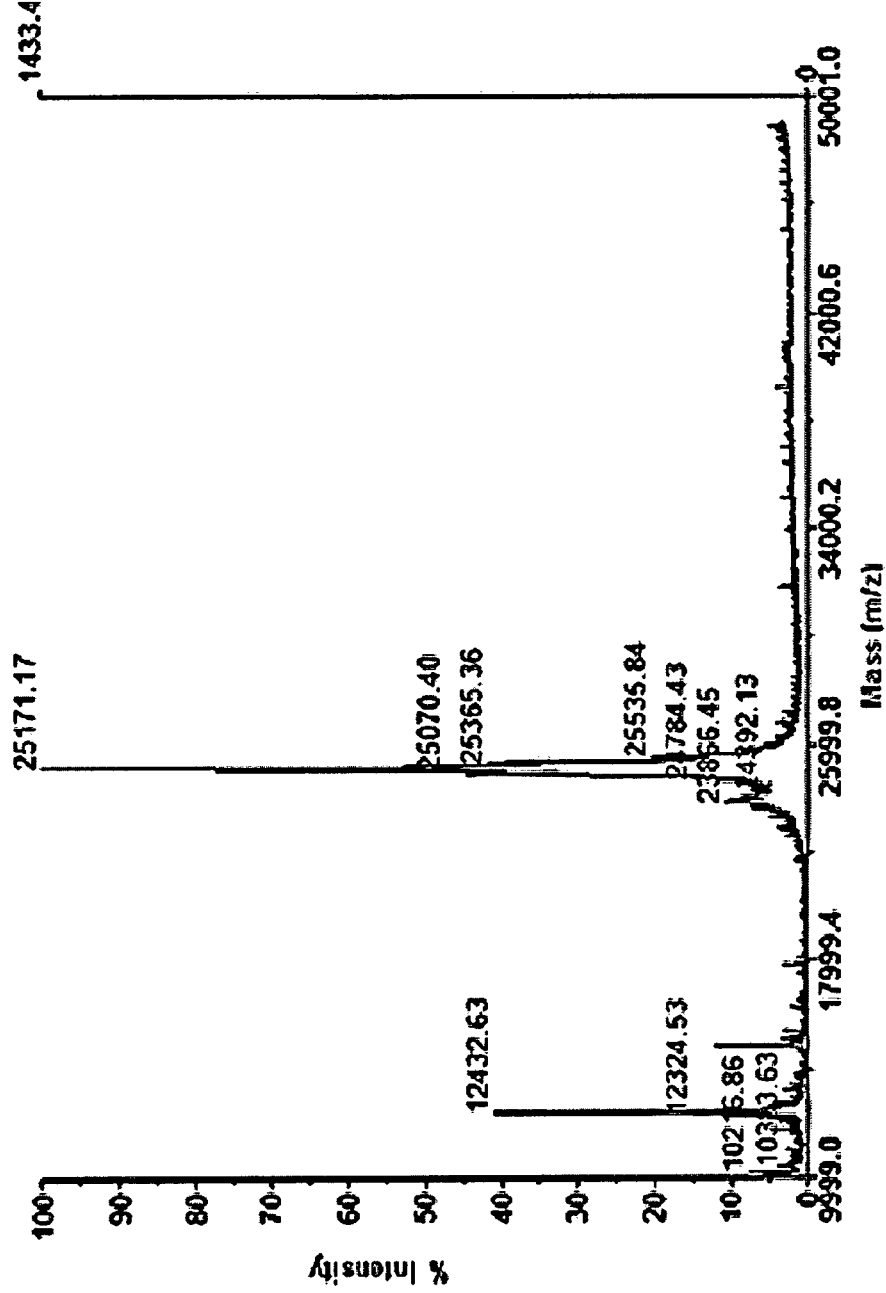
FIGS. 6A-6C are MALDI-ToF spectra of native CT (FIG. 6A), CT(+) (FIG. 6B), and CT-positive-neutral initiator (FIG. 6C). CT(+) was synthesized stoichiometrically and after purification and MALDI-ToF analysis, neutral initiator was reacted with the remaining amino groups, followed by purification and MALDI-ToF. CT(+) showed 5.1 modifications and CT-positive-neutral initiator showed an additional modification of 9 neutral initiators.
Figure 6B:
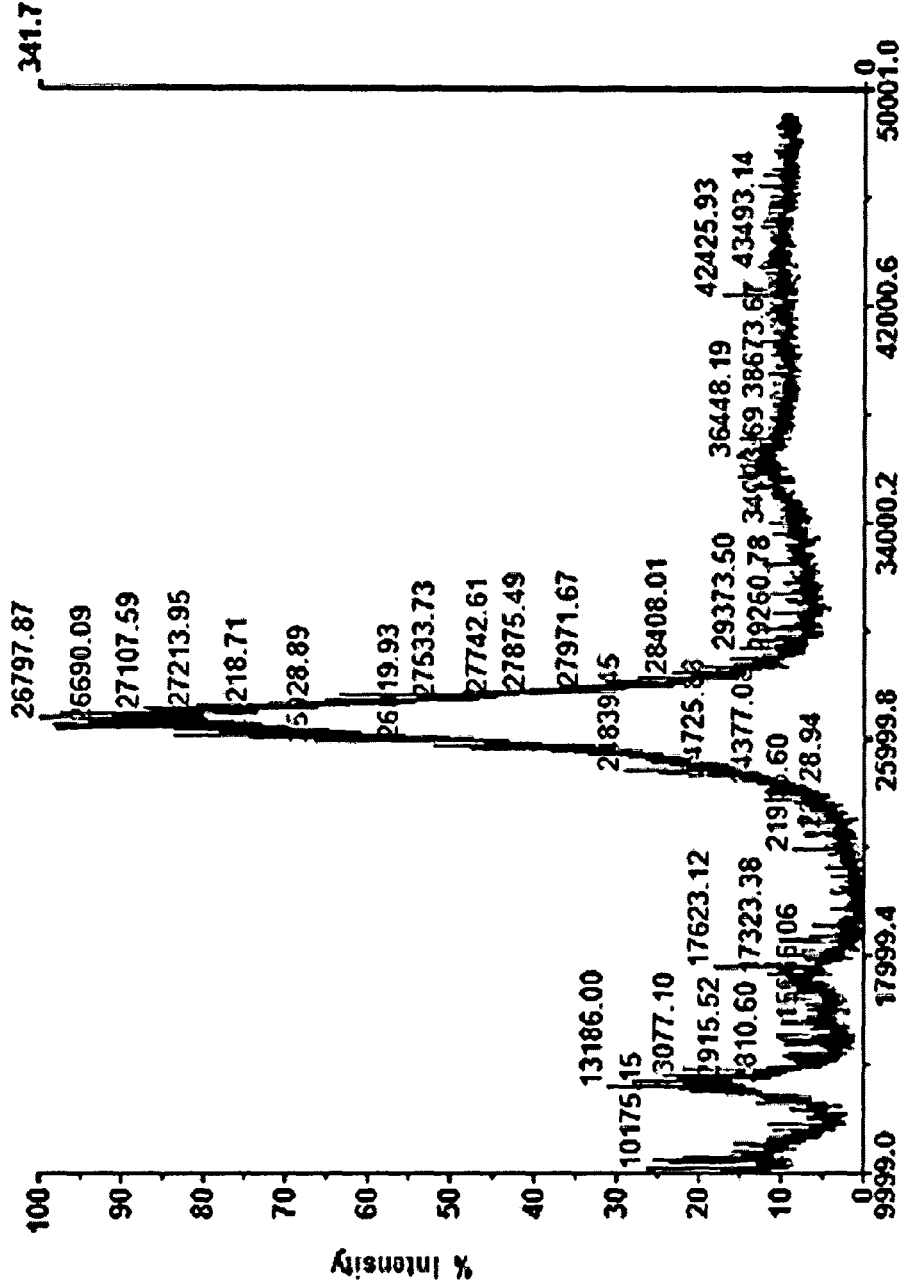
Figure 6C:
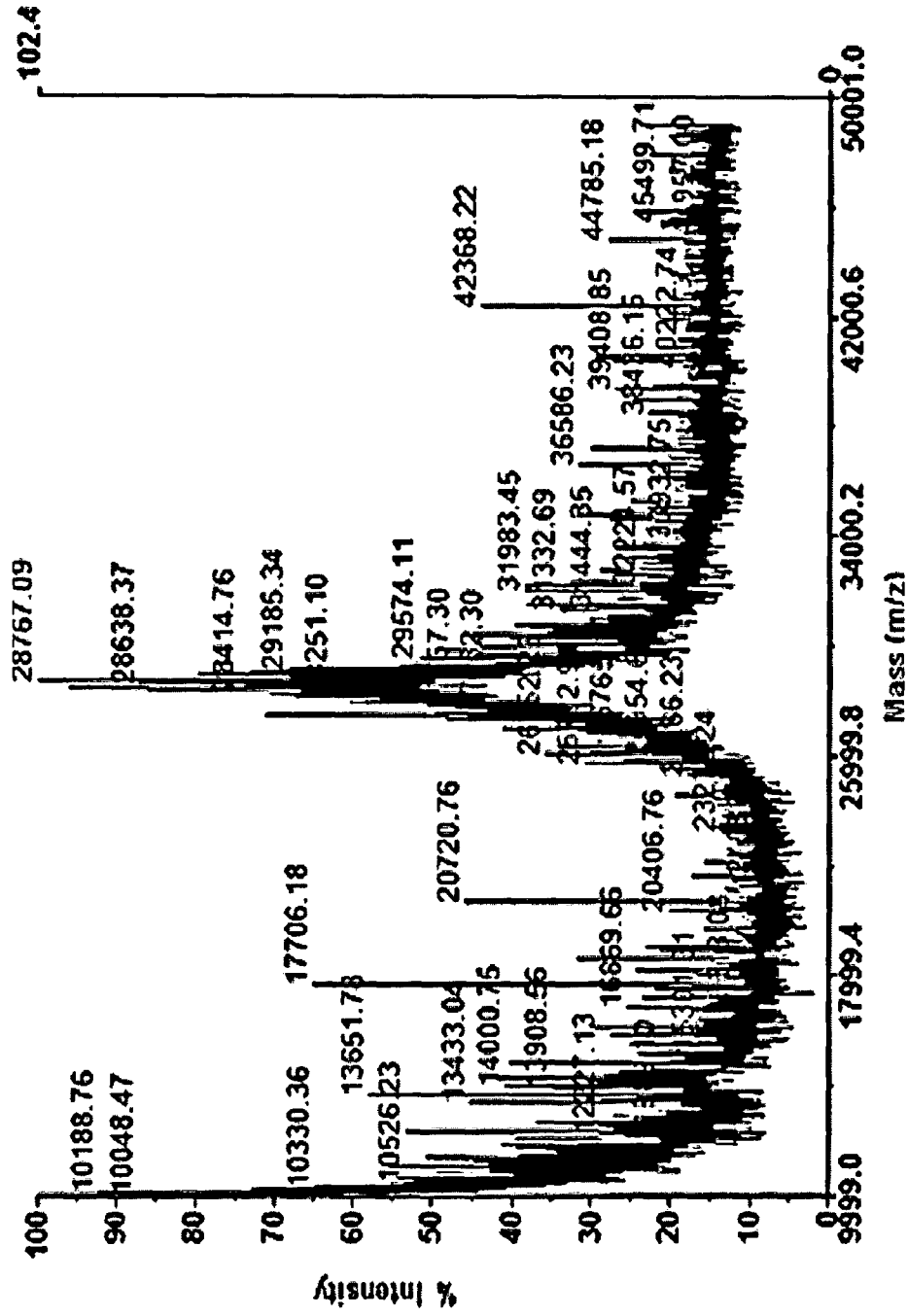
Figure 7:
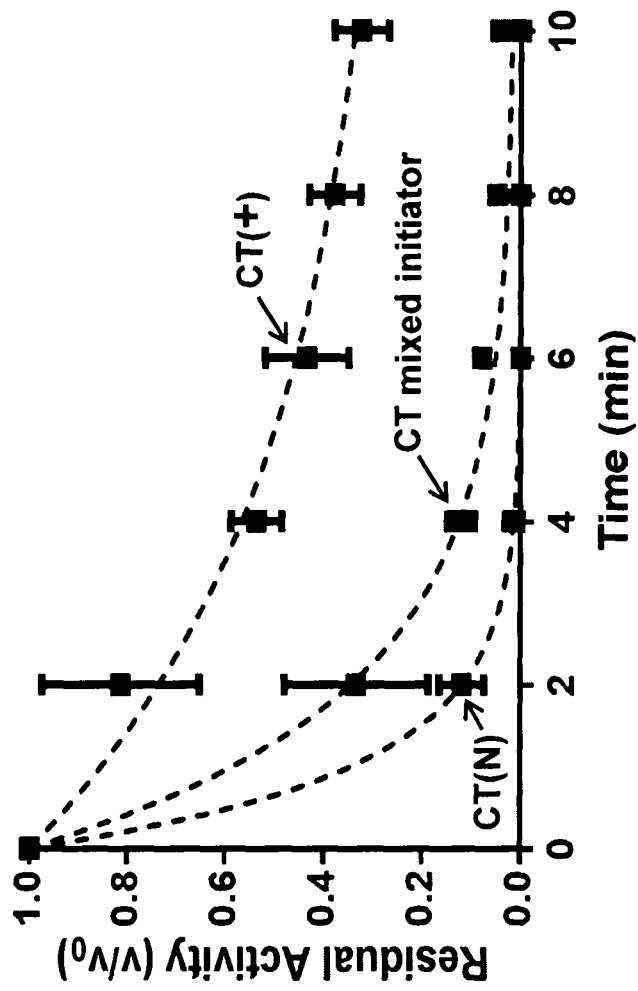
FIG. 7 is a graph plotting residual activity of CT-mixed initiator in relation to CT(N) and CT(+). CT-mixed initiator was modified with about 9 neutral initiators and 5 positive initiators. CT-mixed initiator displayed a stability profile between those of CT(N) and CT(+). Error bars are from standard deviations of triplicate measurements.

To further explore whether net charge restoration caused the observed effects on stability, a CT-initiator complex was synthesized that contained a random mixture of neutral and positive initiators around the protein surface. Characterization by MALDI-ToF showed that the complexes contained an average of 9 neutral and 5 positive initiators per CT (FIGS. 6A-6C). The mixed complex had slightly lower Michaelis-Menten parameters than both the CT-neutral initiator and CT-positive initiator ($k_{cat}$=16.7±0.4 s$^{-1}$, $K_M$=82±7 μM, $k_{cat}/K_M$=0.20±0.01 μM$^{-1}$s$^{-1}$) at pH 8 and 37° C. The mixed initiator complex had a stability curve that fell between the CT-neutral initiator and CT-positive initiator curves while the deactivation rate of the CT-mixed initiator (0.55±0.03 min$^{-1}$) was about half that of CT-neutral initiator (1.06±0.03 min$^{-1}$) (FIG. 7). These data indicated that the stabilizing effect of the positive initiator was most likely due to maintenance of surface charge versus each of the initiators reacting with different amino groups.

Figure 8A:
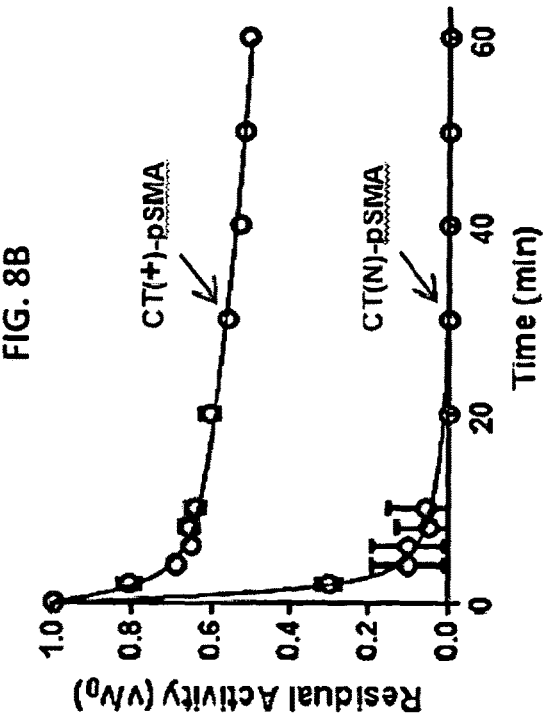
FIGS. 8A-8D are a series of graphs plotting thermal and acid stabilities measured though residual activities at either high temperature or in acid. Thermal stabilities at 50° C. and pH 8 were plotted for CT-pCBMA (FIG. 8A) and CT-pSMA conjugates grown from neutral or positively charged initiators (FIG. 8B). Acid stabilities at pH 1 and 37° C. were plotted for CT-pCBMA (FIG. 8C) and CT-pSMA conjugates grown from neutral or positively charged initiators (FIG. 8D). Connecting lines are nonlinear curve fits. All conjugates synthesized using the positive initiator had increased thermal and acid stabilities in comparison to their neutral initiator conjugate counterparts. Residual activities were normalized to activity at time 0 which was the conjugate's optimal conditions for activity at pH 8 and 37° C. Error bars in all plots represent the standard error of the mean from triplicate measurements.
Figure 8B:
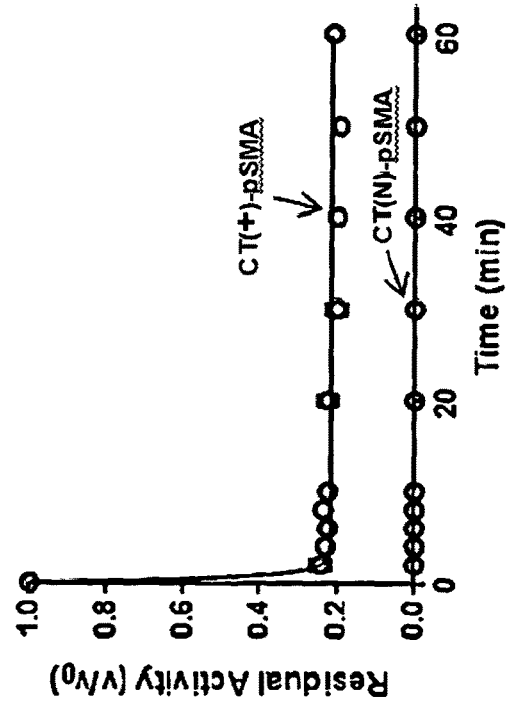
Figure 8C:
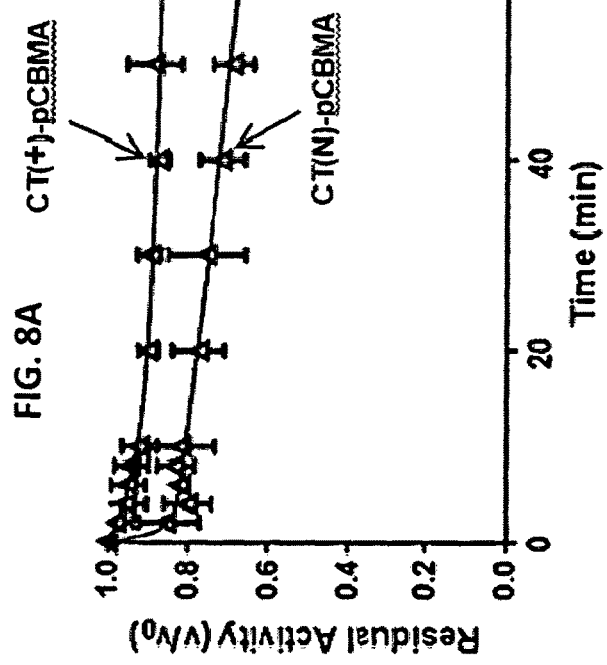
Figure 8D:
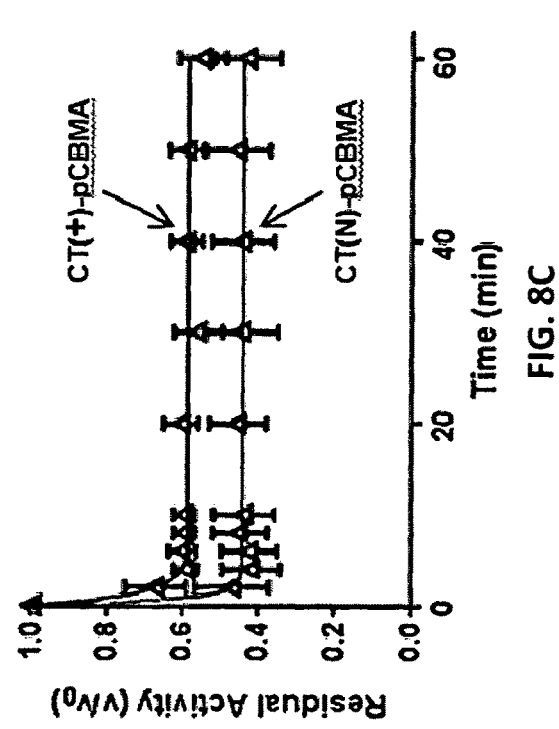

Further studies were conducted to determine the impact of initiator charge on enzyme-polymer conjugate stability. Residual activities of CT-pCBMA and CT-pSMA conjugates, grown from either neutral or positive initiators, were measured after incubation at either high temperature (FIGS. 8A and 8B) or in acid (FIGS. 8C and 8D). At high temperature, both CT-pCBMA conjugates were relatively stable. The CT-positive initiator-pCBMA conjugate was the most stable and even maintained ~90% activity after exposure to high temperature for 60 minutes. By way of comparison, the CT-neutral initiator-pSMA conjugate irreversibly inactivated after just 10 minutes at 50° C. In another demonstration of the impact of maintaining the electrostatic environment of proteins during polymer modification, the CT-positive initiator-pSMA conjugate was remarkably stable (retaining 60% residual activity at 60 minutes).

Other work has elucidated the mechanism of CT-polymer conjugate resistance to acid induced irreversible inactivation. In acid, the CT-positive initiator-pCBMA conjugate maintained about 60% residual activity, compared to about 40% for CT-neutral initiator-pCBMA. Remarkably, even the CT-positive initiator-pSMA conjugate had higher stability and was able to maintain 20% residual activity as compared to CT-neutral initiator-pSMA, which was immediately and irreversibly inactivated.

Example 4—Molecular Dynamics Simulation

Figure 9A:
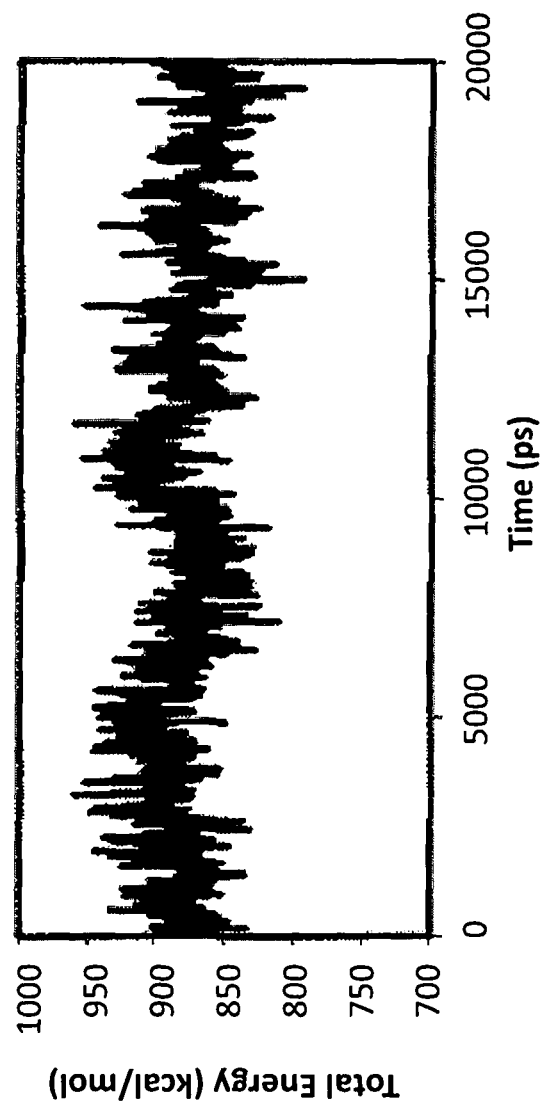
FIGS. 9A-9C are graphs plotting the results of molecular dynamics simulation analysis of a fully modified CT-positive initiator molecule, showing the total energy (kcal/mol) (FIG. 9A), the root mean square deviation (RMSD) of the alpha carbons (nm) (FIG. 9B), and the radius of gyration (nm) (FIG. 9C) of the CT-positive initiator complex over the 20 ns simulation.
Figure 9B:
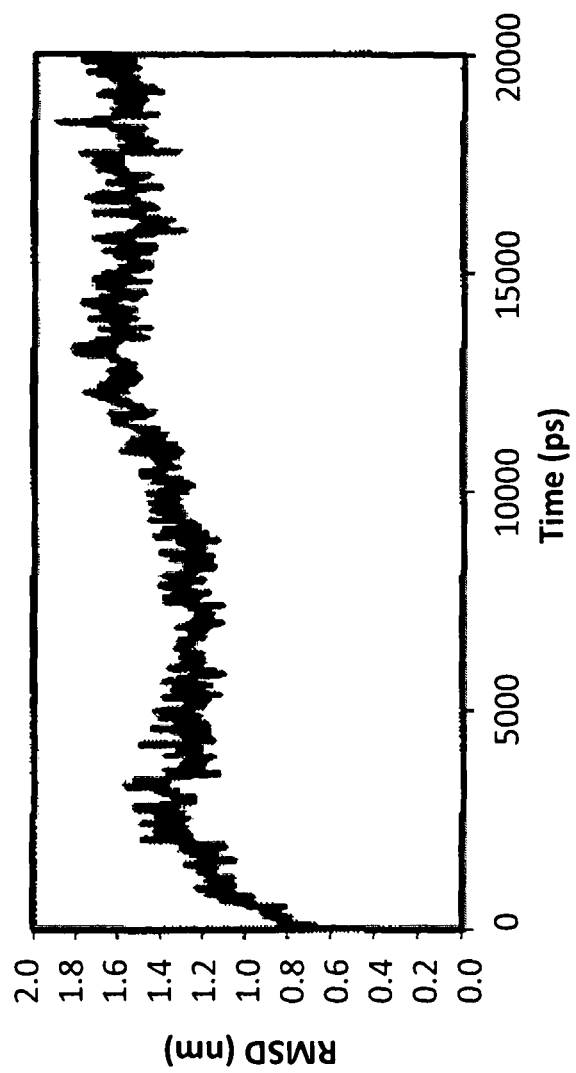
Figure 9C:
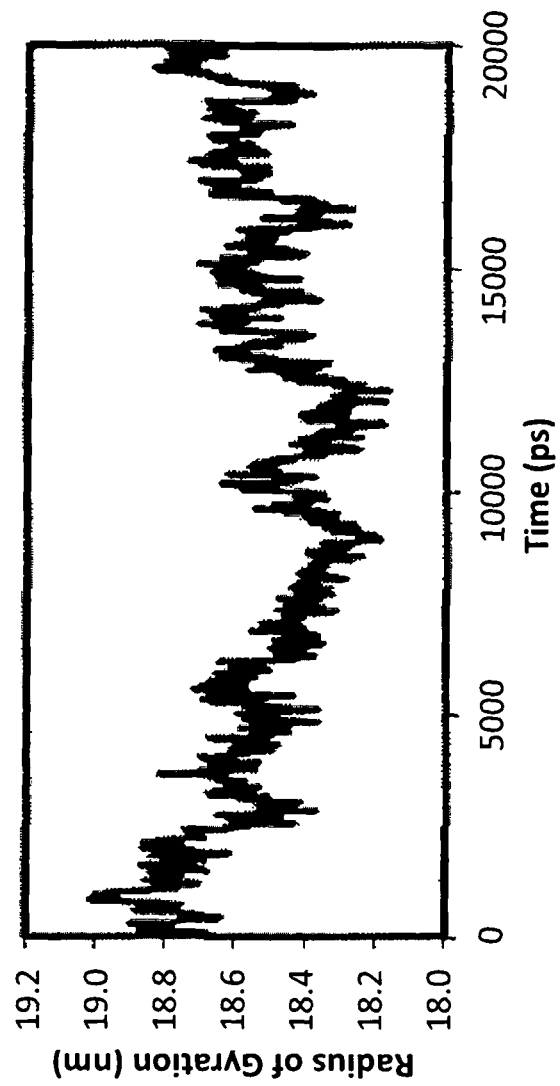

In order to deepen the understanding of why positively charged initiator-CT complexes might restore native stability, a short (20 ns) all-atom molecular dynamics (MD) simulation was performed in a water box with periodic boundary conditions on a fully modified CT (PDB: 4cha) with positive initiators. The simulation was performed to mimic experimental conditions by adjusting the protonation states of ionizable groups to pH 8 and adding 100 mM NaCl. The system was subjected to a short (1 ns) simulated annealing to place the molecule in its lowest energy state and remove bias before starting the 20 ns production run. MD simulations were performed using the OPLS2005 force field and the average radius of gyration was 1.85 nm which was validated against experimental hydrodynamic diameter data (FIGS. 9A-9C). Electrostatic interactions around the protein surface were monitored over the 20 ns trajectory by determining the number of salt bridge formations. The simulations determined when salt bridges between two residues was formed using Visual Molecular Dynamics (VIVID) software. Native CT has one known salt bridge (between the α-ammonium ion of Ile 16 and the carboxylate ion of Asp 194). Destabilization of this salt bridge decreased stability by 2.9 kcal mol$^{-1}$ Ferscht, *J. Mol. Biol.* 1972, 64(2):497-509). In the CT-positive initiator complex, the formation of 4 different salt bridges was observed throughout the 20 ns analysis: Asp 72-Arg 154, Glu 21-Arg 154, Asp 129-Arg 230, and Asp 128-Lys203-positive initiator (FIG. 10A). Arg 154 is located within close proximity of two acidic residues, Asp 72 and Glu 21, and formed salt bridges with both in the simulated model. The time spent in a salt bridge was also monitored over 20 ns (FIG. 10B). The most dominant salt bridge was between Asp 72-Arg 154. Since there was only one salt bridge formed that was associated with a lysine residue, it was possible that the CT-neutral initiator could also form the majority of the salt bridges induced by conformational changes. Additionally, the stabilities of CT and CT-positive initiator were similar, indicating that the formation of additional salt bridges did not significantly enhance CT's stability. Rather, it is more likely that the maintained stability of CT-positive initiator over CT-neutral initiator was due to long-range electrostatic interactions through restoring the charge balance, aligning with the findings of activity and stability of CT-mixed initiator.

Figure 11:
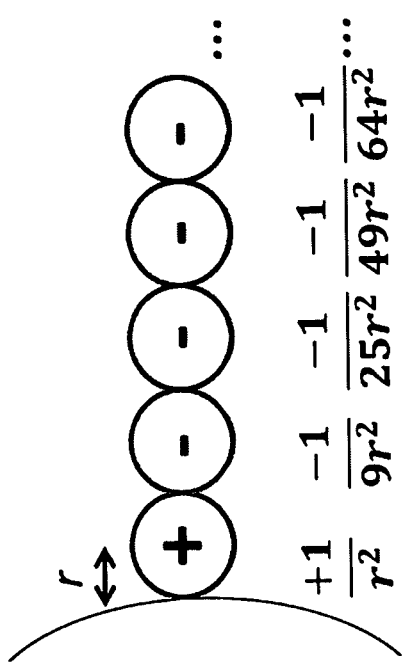
FIG. 11 is a graphic illustrating a CT-positive initiator-pSMA conjugate modeled as point charges. The positive charge is from the quaternary ammonium on the positive initiator, while the remaining negative charges are the anionic sulfonate groups on SMA monomers. Even if there were 99 negative charges to the right of the positive charge, the electric field strength at the protein surface would still be +0.77.

Example 5—Theoretical Explanation of Impact of Maintaining Surface Charge on Protein Polymer Conjugate Function A simple charged initiator might have a dramatic array of negative charges in the polymer. After all, the CT-pSMA conjugate retained 10 positive charges at its surface, but added over 1,000 positive charges to the molecular shell. Charged groups produce an electric field due to interactions with other charged particles in close proximity. The electric field strength at a surface with propagating point charges can be estimated using (equation 2), $$E = \frac{kq}{r^2} \tag{2}$$

where E is electric field (NC$^{-1}$), k is Coulomb's constant (9.0E9 Nm$^2$C$^{-2}$), q is the signed magnitude of the point charge, and r is the distance between the charges. Therefore, the electric field strength is proportional to the magnitude of the electric charge and inversely proportional to the distance. A CT-positive initiator-pSMA conjugate of one polymer chain was modeled to estimate the electric field strength at the protein surface (FIG. 11). Since the electric field is additive, even if there were 100 negative charges (DP=100) following the positive charge, the electric field strength at the protein surface would still be +0.77. This highlighted the importance of maintaining optimal surface charge prior to growth of charged polymers.

Figure 12A:
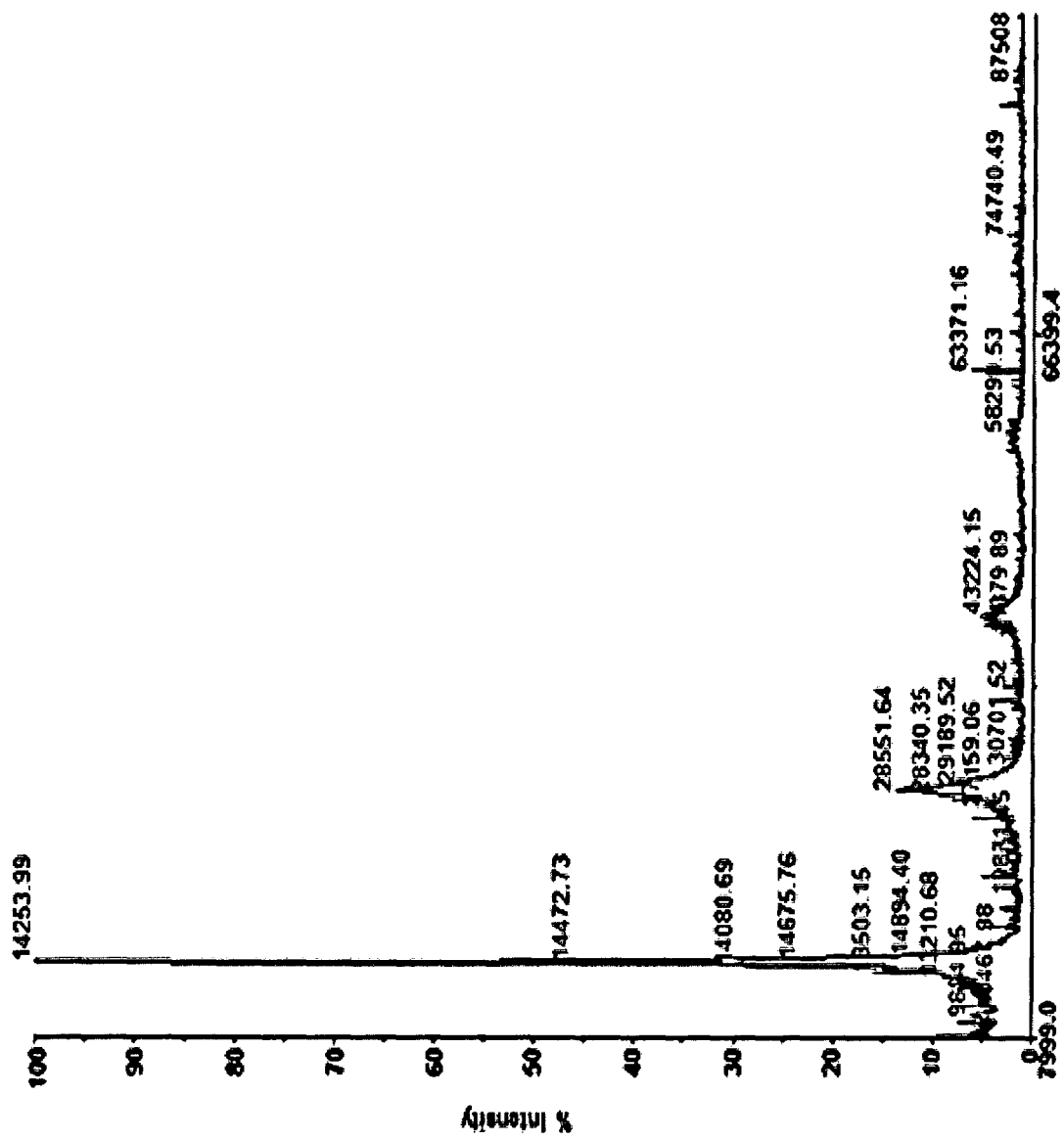
FIGS. 12A-12C are MALDI-ToF spectra of native lysozyme (FIG. 12A), lysozyme-neutral initiator (FIG. 12B), and lysozyme-positive initiator (FIG. 12C). The degree of modification was determined by taking the difference in m/z between the lysozyme-initiator and native lysozyme and then dividing by the molar mass of the initiator (neutral initiator: 220 Da, positive initiator: 320 Da).
Figure 12B:
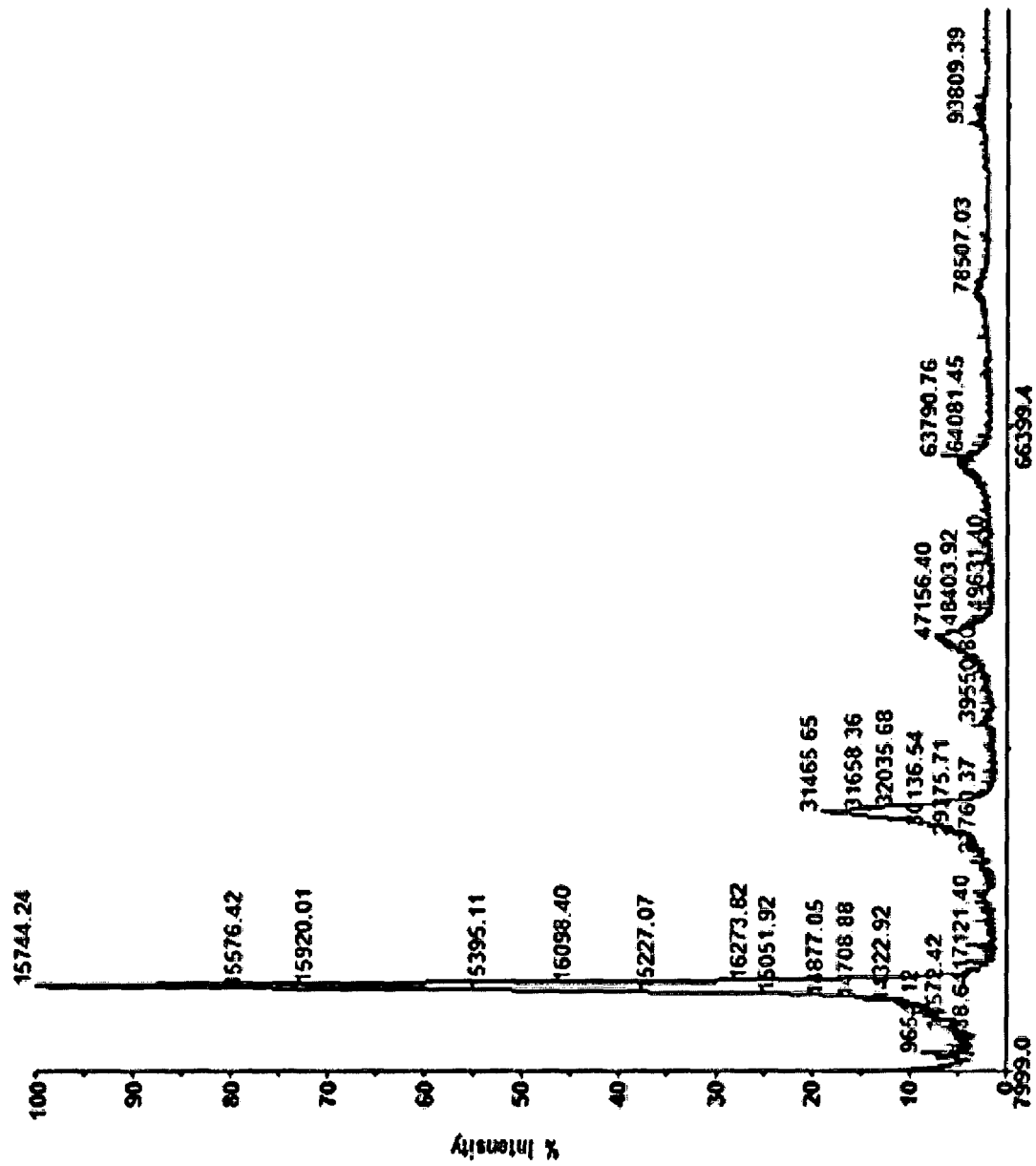
Figure 12C:
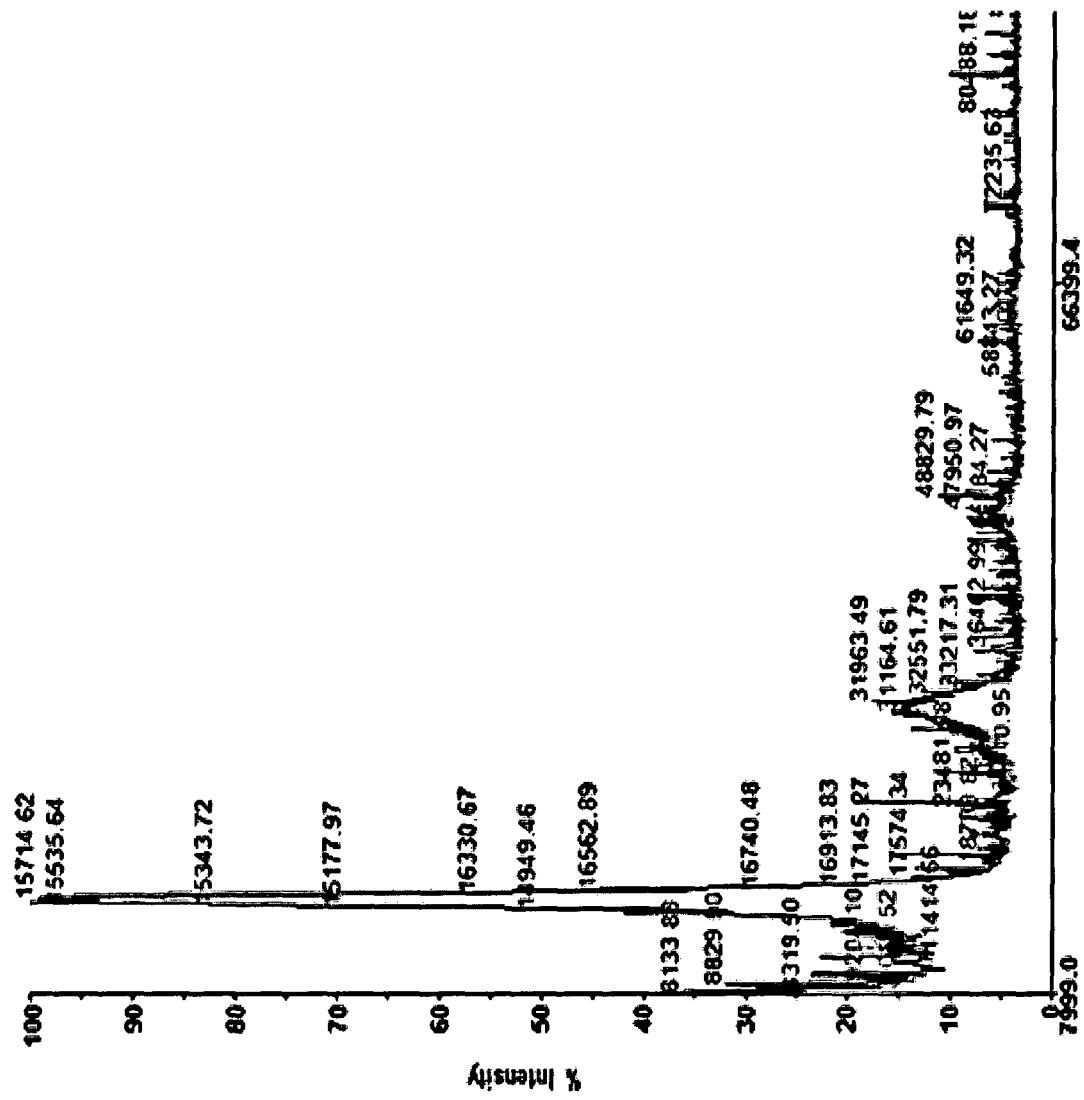

Example 6—the Ability to Maintain the Electrostatic Environment of Protein-Polymer Conjugates is not Limited to Chymotrypsin Although the positively charged initiator results with chymotrypsin were truly compelling, there was a possibility that the effect may have been enzyme-specific. The impact of the positively-charged initiator on the activity and stability of a widely divergent group of enzymes, enzyme-initiator complexes and enzyme-polymer conjugates was therefore explored. Lysozyme (14.3 kDa, 7 amines), avidin (16.4 kDa, 10 amines), uricase (35 kDa, 35 amines), and acetylcholinesterase (AChE, 70 kDa, 26 amines) have differing molecular weights, numbers of amino groups, active sites, and multimeric characteristics. The degree of initiator modification for each protein-initiator complex was determined using a fluorescamine assay, except for lysozyme samples, which were small enough to be determined by MALDI-ToF (FIGS. 12A-12C).

Figure 13A:
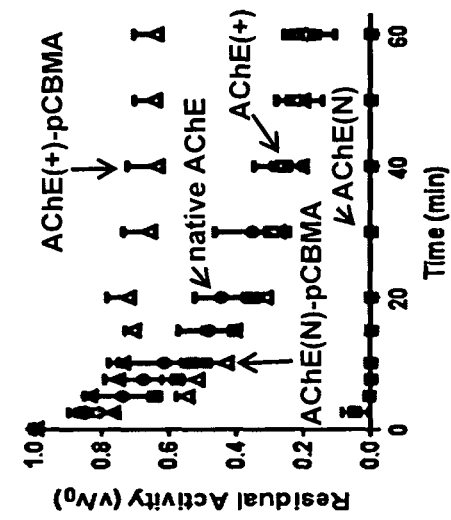
FIGS. 13A-13C are graphs plotting the thermostabilities of proteins and protein-initiators for lysozyme (FIG. 13A), uricase (FIG. 13B), and acetylcholinesterase (FIG. 13C). The thermostabilities of lysozyme, uricase, and acetylcholinesterase samples were performed at 80° C., 75° C., and 50° C., respectively. Error bars represent standard deviations from triplicate measurements. All proteins showed enhanced thermostability when modified with positive initiators versus neutral initiators.

Lysozyme: Lysozyme (Lyz) is a small, single sub-unit protein that is an antimicrobial enzyme and is important for the immune system. Lysozyme hydrolyzes the β-1,4 glycosidic linkages between N-acetylmuramic acid and N-acetylglucosamine that are present in the cell wall of the bacteria. As seen for CT, the positive initiator modified fewer amino groups than the neutral initiator, but high degrees of modification were still achievable (TABLE 3). Lysozyme activity was measured by the change in absorbance at 450 nm over time when using *Micrococcus lysodeikticus* as a substrate. The lysozyme-neutral initiator complex was almost completely inactive (two orders of magnitude less activity than native lysozyme. The compelling results with CT were mirrored for the lysozyme-positive initiator complex, however, and complete restoration of activity for the complex was observed. Growth of pCBMA from Lyz-neutral initiator complex regained activity lost upon neutral initiator attachment while growth of pCBMA from Lyz-positive initiator only showed moderate further increase in activity. Growth of pSMA from both of the initiator-modified lysozyme samples rendered the conjugate inactive and the activity was completely undetectable by absorbance over the experimental time frame. This result for pSMA conjugates was not surprising, however, because strong repulsive electrostatic interactions between the large negatively charged bacteria substrate and the negatively charged pSMA coating would hinder diffusion of the substrate through the polymer to the active site. The thermal stabilities of lysozyme-initiators and subsequent lysozyme-polymer conjugates were assessed next by measuring residual activities over time during incubation at 80° C. (FIG. 13A). Lyz-neutral initiator had the lowest thermal stability and had lost approximately 60% of its original activity after 2 minutes at 80° C. The stability of Lyz-neutral initiator was regained upon growth of pCBMA and was similar to those of native Lyz, Lyz-positive initiator, and Lyz-positive initiator-pCBMA. The thermal stabilities of Lyz-pSMA conjugates could not be assessed because all detectable activities were lost as indicated in TABLE 6.

Avidin: Avidin (Avi) is a tetrameric protein (homo-4-mer) that is approximately 66 kDa in its tetrameric form and is found in the egg whites of birds, reptiles, and amphibians. Its highly specific activity arises from binding strongly to biotin and this binding event is one of the strongest noncovalent interactions known, making avidin extremely useful for biochemical assays/probes and protein purification chemistries. Each sub-unit of avidin can bind to one biotin molecule. In agreement with CT and Lyz, the number of initiator modifications when using the positive initiator was less than that achieved with neutral initiator (4.3 versus 7.9). The activities of avidin samples were measured next using two different techniques (TABLE 6). Biotin binding rates were determined kinetically and total equilibrium biotin binding were determined spectophotometrically using 4'-hydroxyazobenzene-2-carboxylic acid (HABA) dye. Since the avidin-biotin binding is so strong, the displacement of HABA by biotin in the active site can be measured and the amount of bound biotin can be determined by the decrease in absorbance at 500 nm. The biotin binding rate of Avi-neutral initiator was decreased to 0.48 s$^{-1}$ from 105.2 s$^{-1}$ for native avidin. Avi-positive initiator, however, had a 1.7-fold increase in the biotin binding rate compared to Avi-neutral initiator. When comparing the equilibrium binding, the attachment of both neutral and positive initiators decreased the amount of biotin that was able to displace HABA, however, the binding for Avi-positive initiator was slightly increased over Avi-neutral initiator.

Figure 13B:
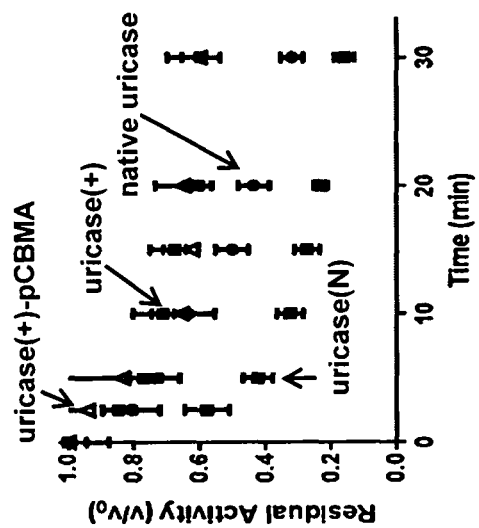

Uricase: In the liver, uricase catalyzes the oxidation of uric acid by gaseous molecular oxygen to produce 5-hydroxyisourate and hydrogen peroxide by the catalytic triad comprised of Thr 57, Lys 10, and His 256 (Girard et al., *Biophys. J.* 2010, 98(10):2365-2373; and Gabison et al., *BMC Struct. Biol.* 2008, 8(1):32). Uricase has a homo-tetrameric structure and the active sites of the monomers are located at dimeric interfaces. There also is a hydrophobic cavity on each monomer located next to the active site, and the flexibility of this cavity is essential for catalysis (Colloc'h and Prangé, *FEBS Lett.* 2014, 588(9):1715-1719). The therapeutic utility of uricase makes it an ideal target for polymer-based protein engineering, but the enzyme has been found to lose almost all activity upon polymer modification. As expected, uricase was completely inactivated upon attachment of the neutral initiator and no activity was detectable. The loss in activity was due to a combined decrease in $k_{cat}$ and increase in $K_M$. Surprisingly, growth of either pCBMA or pSMA did not recover the lost activity and in fact, caused complete inactivation of uricase. Modification of uricase with the positive initiator resulted in an enzyme with detectable activity, though the activity was still significantly less than the native enzyme. The $k_{cat}$ value was decreased and $K_M$ was increased in comparison to native uricase, however these changes were not as significant as for Uri-neutral initiator. Growth of pCBMA from uricase-positive initiator resulted in further loss of activity, but was still detectable. Growth of pSMA however caused complete inactivation of uricase. The large decrease in activity could be due to a combination of decreased flexibility (causing decreased $k_{cat}$), modification of Lys 10 in the active site (causing increased $K_M$), and increased hydrophilicity of the cavity when using the positive initiator (causing increased $K_M$). The thermal stabilities of uricase samples were determined next by measuring the residual activities over time at 75° C. Uri-neutral initiator stability was decreased in comparison to native uricase while Uri-positive initiator was higher than native uricase (FIG. 13B). pCBMA growth from Uri-positive initiator did not further improve its thermal stability.

Figure 13C:
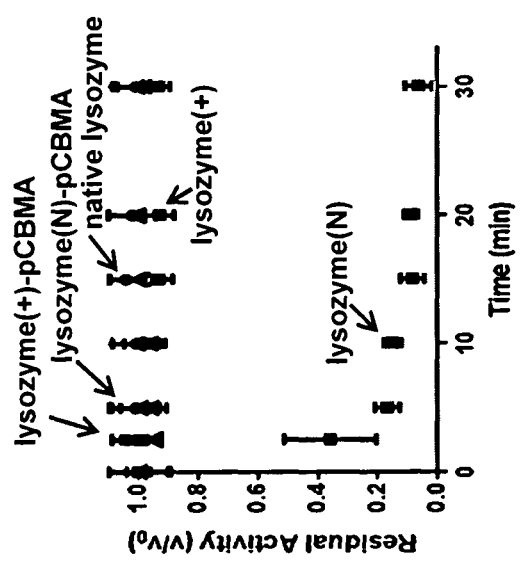

Acetylcholinesterase: Acetylcholinesterase (AChE) catalyzes the hydrolysis of acetylcholine to acetic acid and choline. The positively charged substrate binds to the anionic site to correctly position it for hydrolysis by the catalytic triad (Ser 200, Glu 327, His 440) (Axelsen et al., *Protein Sci.* 1994, 3(2):188-197; and Dvir et al., *Chem. Biol. Interact.* 2010, 187(1-3):10-22). AChE-initiators showed decreased activities in comparison to native AChE. AChE-neutral initiator and AChE-positive initiator had similar $k_{cat}$ values, but the $K_M$ for the AChE-positive initiator complex was about 2.4× higher, leading to a lower overall catalytic efficiency. A tertiary structure-based prediction of reactive amino groups was performed (Carmali et al., supra) on acetylcholinesterase (PDB: 1EEA) and Lys 325, located closely to the active site residue Glu 327, was determined to be fast-reacting. The decrease in substrate affinity of the AChE-positive initiator was therefore most likely due to modification of Lys 325, which would have disrupted the anionic nature of the substrate binding site. AChE-neutral initiator-pCBMA had further decreased activity in comparison to AChE-neutral initiator due largely to a decrease in kcat and the activity of AChE-neutral initiator-pSMA was undetectable. AChE-positive initiator-pCBMA had regained the activity lost upon attachment of the positive initiator and was the sample that had the highest activity of all of the modified AChE samples. Additionally, while the activity was undetectable for AChE-neutral initiator-pSMA, the growth of pSMA from AChE-positive initiator produced a conjugate with detectable activity. Thermal stabilities of acetylcholinesterase samples were determined next by measuring the residual activities over time at 50° C. (FIG. 13C). AChE-neutral initiator was irreversible inactivated within the first 2 minutes of incubation at 50° C. Some stability was regained after growth of pCBMA, but was still less than native. AChE-positive initiator showed increased thermal stabilities over AChE-neutral initiator, but was slightly less than native AChE. Conjugates of pCBMA and pSMA from AChE-positive initiators showed the highest thermal stabilities of all samples and AChE-positive initiator-pSMA had retained about 70% activity after 60 minutes of incubation at elevated temperatures.

Thus, in all cases, the protein-positive initiator samples examined had increased thermostability in comparison to the protein-neutral initiators. The stability curves of protein-positive initiators highly mimicked the thermostability of their native proteins, similar to the results for CT. The fact that these findings were independent of protein type further supported the idea that restoration of surface charge through engineered charged initiators can stabilize proteins through long-range electrostatic interactions.

Protein-polymer conjugate structure-function-dynamic relationships are important to understand in order to help guide future conjugate designs with optimal function. As demonstrated herein, the design of ATRP-initiators, a factor that is often overlooked in the design process, is of equal importance to polymer design. The charge of the ATRP-initiator should be similar to the charge of the targeted residue to be modified so that the protein surface charge is restored prior to ATRP.

TABLE 6A

Characterization and activities of lysozyme and its protein-initiator and protein-polymer complexes.

| Lysozyme | Number of initiators | Cleaved polymer $M_n$ (KDa); PDI | Conjugate $M_n$ (KDa) | Activity $\Delta A_{450} \times 10^{-4} (s^{-1})$ |
|---|---|---|---|---|
| Native | — | | | 32.3 ± 0.5 |
| (N) | 6.7 | | | 1.0 ± 0.1 |
| (+) | 4.6 | | | 23.7 ± 1.5 |
| (N)-pCBMA | 6.7 | 9.4; 1.38 | 77.0 | 10.2 ± 0.2 |
| (+)-pCBMA | 4.6 | 9.2; 1.34 | 56.3 | 28.5 ± 0.4 |
| (N)-pSMA | 6.7 | | 173.8 ± 19.5 | undetectable |
| (+)-pSMA | 4.6 | | 135.6 ± 21.3 | undetectable |

TABLE 6B

Characterization and activities of avidin and its protein-initiator and protein-polymer complexes.

| Avidin | Number of initiators | Cleaved polymer $M_n$ (KDa); PDI | Conjugate $M_n$ (KDa) | Activity biotin binding rate (s$^{-1}$) | HABA binding, $K_{assoc}$ (μM) |
|---|---|---|---|---|---|
| Native | — | | | 92.5 ± 14.1 | 2.13 ± 0.09 |
| (N) | 7.9 | | | 1.09 ± 0.07 | 2.10 ± 0.12 |
| (+) | 7.0 | | | 1.69 ± 0.04 | 2.11 ± 0.10 |
| (N)-pCBMA | 7.9 | 27.9; 1.82 | 237.4 | 0.23 ± 0.07 | 0.56 ± 0.01 |
| (+)-pCBMA | 7.0 | 32.0; 1.93 | 241.0 | 1.64 ± 0.08 | 0.71 ± 0.01 |

TABLE 6C

Characterization and activities of uricase and AChE and their protein-initiator and protein-polymer complexes.

| Uricase | Number of initiators | Cleaved polymer $M_n$ (KDa); PDI | Conjugate $M_n$ (KDa) | $k_{cat}$ (s$^{-1}$) | $K_M$ (μM) | $k_{cat}/K_M$ (μM$^{-1}$s$^{-1}$) |
|---|---|---|---|---|---|---|
| Native | — | | | 3.42 ± 0.05 | 12.9 ± 0.6 | 0.266 ± 0.013 |
| (N) | 25.3 | | | 0.18 ± 0.01 | 119.4 ± 9.7 | 0.002 ± 0.0006 |
| (+) | 19.8 | | | 2.14 ± 0.04 | 25.4 ± 1.4 | 0.084 ± 0.005 |
| (N)-pCBMA | 25.3 | 8.8; 1.41 | 257.6 | undetectable | undetectable | undetectable |
| (+)-pCBMA | 19.8 | 8.1; 1.36 | 195.4 | 0.03 ± 0.003 | 22.0 ± 7.6 | 0.001 ± 0.0005 |
| (N)-pSMA | 25.3 | | 166.2 ± 3.1 | undetectable | undetectable | undetectable |
| (+)-pSMA | 19.8 | | 185.9 ± 2.4 | undetectable | undetectable | undetectable |

| AChE | Number of initiators | | | $k_{cat}$ (s$^{-1}$) | $K_M$ (μM) | $k_{cat}/K_M$ (μM$^{-1}$s$^{-1}$) |
|---|---|---|---|---|---|---|
| Native | — | | | 120.5 ± 3.3 | 309 ± 21 | 0.390 ± 0.029 |
| (N) | 14.2 | | | 98.6 ± 1.9 | 206 ± 12 | 0.479 ± 0.029 |
| (+) | 10.2 | | | 119.1 ± 2.7 | 337 ± 19 | 0.353 ± 0.021 |
| (N)-pCBMA | 14.2 | 7.9; 1.35 | 184.0 | 2.9 ± 0.1 | 275 ± 19 | 0.010 ± 0.007 |
| (+)-pCBMA | 10.2 | 8.5; 1.34 | 158.5 | 115.0 ± 3.2 | 329 ± 22 | 0.349 ± 0.026 |
| (N)-pSMA | 19.2 | | 330.5 ± 0.7 | undetectable | undetectable | undetectable |
| (+)-pSMA | 18.4 | | 308.7 ± 9.2 | 2.3 ± 0.1 | 214 ± 14 | 0.011 ± 0.001 |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

What is claimed is:

1. A method for generating a protein-initiator conjugate, comprising contacting a protein with an controlled radical polymerization (CRP) initiator, wherein the CRP initiator comprises an amine-reactive group, one or more alkyl halide groups, and a positively charged group.

2. The method of claim 1, wherein the amine-reactive group comprises an active ester.

3. The method of claim 2, wherein the active ester comprises an N-hydroxysuccinimide ester, a nitrophenol ester, a pentafluorophenol ester, or an oxybenzotriaole ester.

4. The method of claim 1, wherein the alkyl halide comprises bromine.

5. The method of claim 1, wherein the positively charged group comprises a quaternary ammonium.

6. The method of claim 1, wherein the protein is an enzyme.

7. The method of claim 6, wherein the enzyme is an esterase, a lipase, an organophosphate hydrolase, an aminase, an oxidoreductase, a hydrogenase, or lysozyme.

8. A protein-initiator conjugate comprising a protein coupled to a controlled radical polymerization (CRP) initiator, wherein the CRP initiator comprises an amine-reactive group, one or more alkyl halide groups, and a positively charged group.

9. The protein-initiator conjugate of claim 8, wherein the amine-reactive group comprises an active ester.

10. The protein-initiator conjugate of claim 9, wherein the active ester comprises an N-hydroxysuccinimide ester, a nitrophenol ester, a pentafluorophenol ester, or an oxybenzotriaole ester.

11. The protein-initiator conjugate of claim 8, wherein the alkyl halide comprises bromine.

12. The protein-initiator conjugate of claim 8, wherein the positively charged group comprises a quaternary ammonium.

13. The protein-initiator conjugate of claim 8, wherein the protein is an enzyme.

14. The protein-initiator conjugate of claim 13, wherein the enzyme is an esterase, a lipase, an organophosphate hydrolase, an aminase, an oxidoreductase, a hydrogenase, or a lysozyme.

15. A method for generating a protein-polymer conjugate, the method comprising contacting a protein-initiator conjugate with a population of monomers in the presence of a transition metal catalyst or metal-free organic complex that can participate in a redox reaction, wherein the initiator comprises an amine-reactive group, one or more alkyl halide groups, and a positively charged group.

16. The method of claim 15, wherein the amine-reactive group comprises an active ester.

17. The method of claim 16, wherein the active ester comprises an N-hydroxysuccinimide ester, a nitrophenol ester, a pentafluorophenol ester, or an oxybenzotriaole ester.

18. The method of claim 15, wherein the alkyl halide comprises bromine.

19. The method of claim 15, wherein the positively charged group comprises a quaternary ammonium.

20. The method of claim 15, wherein the protein is an enzyme.

21. The method of claim 20, wherein the enzyme is an esterase, a lipase, an organophosphate hydrolase, an aminase, an oxidoreductase, a hydrogenase, or lysozyme.

22. The method of claim 15, wherein the monomer is selected from the group consisting of carboxybetaine methacrylate, (oligo(ethylene glycol) methacrylate), 2-dimethylaminoethyl methacrylate, sulfobetaine methacrylate, 2-(methylsulfinyl)ethyl acrylate, oligo(ethylene oxide) methyl ether methacrylate, and (hydroxyethyl)methacrylate.

23. The protein-initiator conjugate of claim 8, wherein the alkyl halide comprises chlorine.

* * * * *

SEQUENCE LISTING

<160> NUMBER OF SEQ ID NOS: 8

<210> SEQ ID NO 1
<211> LENGTH: 4
<212> TYPE: PRT
<213> ORGANISM: Artificial Sequence
<220> FEATURE:
<223> OTHER INFORMATION: synthetic polypeptide

<400> SEQUENCE: 1

```
Ala Ala Pro Phe
1
```

<210> SEQ ID NO 2
<211> LENGTH: 15
<212> TYPE: PRT
<213> ORGANISM: Bos taurus

<400> SEQUENCE: 2

```
Cys Gly Val Pro Ala Ile Gln Pro Val Leu Ser Gly Leu Ser Arg
1               5                   10                  15
```

<210> SEQ ID NO 3
<211> LENGTH: 21
<212> TYPE: PRT
<213> ORGANISM: Bos taurus

<400> SEQUENCE: 3

```
Ile Val Asn Gly Glu Glu Ala Val Pro Gly Ser Trp Pro Trp Gln Val
1               5                   10                  15

Ser Leu Gln Asp Lys
            20
```

<210> SEQ ID NO 4
<211> LENGTH: 43
<212> TYPE: PRT
<213> ORGANISM: Bos taurus

<400> SEQUENCE: 4

```
Thr Gly Phe His Phe Cys Gly Gly Ser Leu Ile Asn Glu Asn Trp Val
1               5                   10                  15

Val Thr Ala Ala His Cys Gly Val Thr Thr Ser Asp Val Val Val Ala
            20                  25                  30

Gly Glu Phe Asp Gln Gly Ser Ser Glu Lys
        35                  40
```

<210> SEQ ID NO 5
<211> LENGTH: 38
<212> TYPE: PRT
<213> ORGANISM: Bos taurus

<400> SEQUENCE: 5

```
Leu Ser Thr Ala Ala Ser Phe Ser Gln Thr Val Ser Ala Val Cys Leu
1               5                   10                  15
```

```
Pro Ser Ala Ser Asp Asp Phe Ala Ala Gly Thr Thr Cys Val Thr Thr
            20                  25                  30

Gly Trp Gly Leu Thr Arg
            35

<210> SEQ ID NO 6
<211> LENGTH: 16
<212> TYPE: PRT
<213> ORGANISM: Bos taurus

<400> SEQUENCE: 6

Leu Gln Gln Ala Ser Leu Pro Leu Leu Ser Asn Thr Asn Cys Lys Lys
1               5                   10                  15

<210> SEQ ID NO 7
<211> LENGTH: 5
<212> TYPE: PRT
<213> ORGANISM: Bos taurus

<400> SEQUENCE: 7

Tyr Trp Gly Thr Lys
1               5

<210> SEQ ID NO 8
<211> LENGTH: 25
<212> TYPE: PRT
<213> ORGANISM: Bos taurus

<400> SEQUENCE: 8

Asp Ala Met Ile Cys Ala Gly Ala Ser Gly Val Ser Ser Cys Met Gly
1               5                   10                  15

Asp Ser Gly Gly Pro Leu Val Cys Lys
            20                  25
```